United States Patent
Van Emelen et al.

(10) Patent No.: US 8,557,825 B2
(45) Date of Patent: Oct. 15, 2013

(54) SULFONYL-DERIVATIVES AS NOVEL INHIBITORS OF HISTONE DEACETYLASE

(75) Inventors: Kristof Van Emelen, Sint-Niklaas (BE); Janine Arts, GM Breda (NL); Leo-Jacobus Jozef Backx, Arendonk (BE); Hans Louis Jos De Winter, Schilde (BE); Sven Franciscus Anna Van Brandt, Nijlen (BE); Marc Gustaaf Celine Verdonck, Gierle (BE); Lieven Meerpoel, Beerse (BE); Isabelle Noëlle Constance Pilatte, Louviers (FR); Virginie Sophie Poncelet, Le Manier sur Seine (FR); Alexey Borisovich Dyatkin, Ambler, PA (US); Jimmy Arnold Viviene Van heusden, Oelegem (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 13/325,330

(22) Filed: Dec. 14, 2011

(65) Prior Publication Data

US 2012/0088754 A1    Apr. 12, 2012

Related U.S. Application Data

(60) Division of application No. 12/759,256, filed on Apr. 13, 2010, now Pat. No. 8,097,611, which is a division of application No. 11/926,759, filed on Oct. 29, 2007, now Pat. No. 7,704,998, which is a continuation of application No. 11/668,906, filed on Jan. 30, 2007, now Pat. No. 7,709,487, which is a division of application No. 10/507,708, filed as application No. PCT/EP03/02516 on Mar. 11, 2003, now Pat. No. 7,205,304.

(60) Provisional application No. 60/363,799, filed on Mar. 13, 2002, provisional application No. 60/420,989, filed on Oct. 24, 2002.

(51) Int. Cl.
*A61K 31/496* (2006.01)
*C07D 295/26* (2006.01)

(52) U.S. Cl.
USPC ..................... 514/255.02; 544/383

(58) Field of Classification Search
None
See application file for complete search history.

(56) References Cited

U.S. PATENT DOCUMENTS

| 6,294,538 B1 | 9/2001 | Mylari |
| 2005/0080258 A1 | 4/2005 | Davis et al. |
| 2005/0171347 A1 | 8/2005 | Van Emelen et al. |
| 2005/0222414 A1 | 10/2005 | Van Emelen et al. |

FOREIGN PATENT DOCUMENTS

| CA | 2305568 | 4/1999 |
| EP | 0827742 | 3/1998 |
| WO | WO 98/55449 | 12/1998 |
| WO | WO 01/38322 | 5/2001 |
| WO | WO 0151469 | 7/2001 |
| WO | WO 01/70675 | 9/2001 |

OTHER PUBLICATIONS

Marks, et al. "Histone Deacetylases and Cancer: Causes and Therapies", *Nature Reviews/Cancer*, vol. 1, pp. 194-202, Dec. 2001.
Finnin, et al. "Structures of a Histone Deacetylase Homologue Bound to the TSA and SAHA Inhibitors", *Nature*, vol. 401, pp. 188-193, Sep. 1999.
Mosmann, T., "Rapid Colorimetric Assay for Cellular Growth and Survival: Application to Proliferation and Cytotoxicity Assays", *Journal of Immunological Methods*, vol. 65: 55-63, Jun. 1983.
Finney, D.J., "Graded Responses", *Probit Analyses* $2^{nd}$ edition, Ch. 10, Cambridge University Press Cambridge, 1962.
Gorrod, et al., "The Metabolism of N-Ethyl-N-Methylaniline by Rabbit Liver Microsomes: The Measurement of Metabolites by Gas-Liquid Chromatography", *Xenobiotica*, vol. 5, No. 8, pp. 453-462, 1975.
Awada, A. et al., "The Pipeline of New Anticancer Agents for Breast Cancer Treatment in 2003", *Oncology Hematology*, (2003), pp. 45-63, vol. 48.
Awada, A. et al., Critical Reviews in Oncology/Hematology, 2003, vol. 48, pp. 45-63.
Chemotherapy of Cancer, (1981) $2^{nd}$ edition, pp. 362-365.

*Primary Examiner* — Kamal Saeed

(57) ABSTRACT

This invention comprises the novel compounds of formula (I)

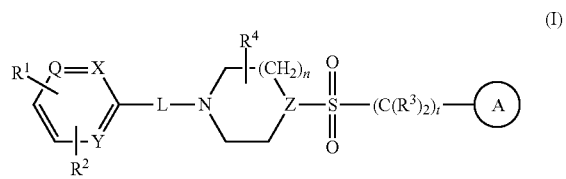

wherein n, m, t, $R^1$, $R^2$, $R^3$, $R^4$, L, Q, X, Y, Z and

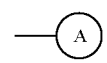

have defined meanings, having histone deacetylase inhibiting enzymatic activity; their preparation, compositions containing them and their use as a medicine.

9 Claims, No Drawings

SULFONYL-DERIVATIVES AS NOVEL INHIBITORS OF HISTONE DEACETYLASE

CROSS REFERENCE TO RELATED APPLICATIONS

This application is a divisional of U.S. application Ser. No. 12/759,256 filed Apr. 13, 2010 now U.S. Pat. No. 8,097,611 which is a divisional of U.S. application Ser. No. 11/926,759 filed on Oct. 29, 2007, now U.S. Pat. No. 7,704,998 which is a continuation of U.S. application Ser. No. 11/668,906 filed on Jan. 30, 2007, now U.S. Pat. No. 7,709,487 which is a divisional of U.S. application for Pat. Ser. No. 10/507,708, filed Sep. 13, 2004, now U.S. Pat. No. 7,205,304 which is the National Stage application under 35 U.S.C. §371 of PCT/EP03/02516, filed Mar. 11, 2003, now U.S. Pat. No. 7,205,304, which claims priority to U.S. Provisional Application Ser. No. 60/363,799, filed Mar. 13, 2002, and to U.S. Provisional Application Ser. No. 60/420,989, filed Oct. 24, 2002, the contents of all of which are incorporated herein by reference in their entirety.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

In all eukaryotic cells, genomic DNA in chromatine associates with histones to form nucleosomes. Each nucleosome consists of a protein octamer made up of two copies of each histones H2A, H2B, H3 and H4. DNA winds around this protein core, with the basic amino acids of the histones interacting with the negatively charged phosphate groups of the DNA. The most common posttranslational modification of these core histones is the reversible acetylation of the ε-amino groups of conserved, highly basic N-terminal lysine residues. The steady state of histone acetylation is established by the dynamic equilibrium between competing histone acetyltransferase(s) and histone deacetylase(s) herein referred to as "HDAC". Histone acetylation and deacetylation has long been linked to transcriptional control. The recent cloning of the genes encoding different histone acetyltransferases and histone deacetylases provided a possible explanation for the relationship between histone acetylation and transcriptional control. The reversible acetylation of histones can result in chromatin remodelling and as such act as a control mechanism for gene transcription. In general, hyperacetylation of histones facilitates gene expression, whereas histone deacetylation is correlated with transcriptional repression. Histone acetyltransferases were shown to act as transcriptional coactivators, whereas histone deacetylases were found to belong to transcriptional repression pathways.

The dynamic equilibrium between histone acetylation and deacetylation is essential for normal cell growth. Inhibition of histone deacetylase results in cell cycle arrest, cellular differentiation, apoptosis and reversal of the transformed phenotype. Therefore HDAC inhibitors can have great therapeutic potential in the treatment of cell proliferative diseases or conditions (Marks et al., Nature Reviews, Cancer 1: 194-202, 2001).

The study of inhibitors of histone deacetylases (HDAC) indicates that indeed these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 March, 1998).

Patent application WO01/38322 published on May 31, 2001 discloses amongst others inhibitors of histone deacetylase of general formula Cy-L$^1$-Ar—Y$^1$—C(O)—NH—Z, providing compositions and methods for treating cell proliferative diseases and conditions.

Patent application WO01/70675 published on 27 Sep. 2001 discloses inhibitors of histone deacetylase of formula Cy-S(O)$_2$—NH—Y$^3$—W and further provides compositions and methods for treating cell proliferative diseases and conditions.

The problem to be solved is to provide histone deacetylase inhibitors with high enzymatic activity and also show advantageous properties such as cellular activity and increased bioavailability, preferably oral bioavailability, and have little or no side effects.

The novel compounds of the present invention solve the above described problem. The compounds differ from the prior art in structure.

The compounds of the present invention show excellent in-vitro histone deacetylase inhibiting enzymatic activity. The present compounds have advantageous properties with regard to cellular activity and specific properties with regard to inhibition of cell cycle progression at both G1 and G2 checkpoints (p21 induction capacity). The compounds of the present invention show good metabolic stability and high bioavailability and more particular they show oral bioavailability. Moreover, the compounds of the present invention have a low affinity for the P450 enzymes, which reduces the risk of adverse drug-drug interaction allowing also for a wider safety margin.

This invention concerns compounds of formula (I)

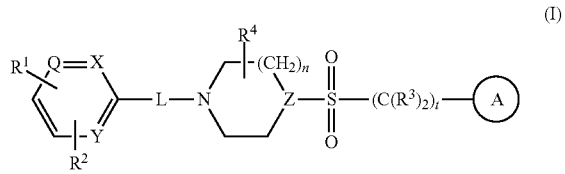

the N-oxide forms, the pharmaceutically acceptable addition salts and the stereo-chemically isomeric forms thereof, wherein n is 0, 1, 2 or 3 and when n is 0 then a direct bond is intended;

t is 0, 1, 2, 3 or 4 and when t is 0 then a direct bond is intended;

each Q is nitrogen or

each X is nitrogen or

each Y is nitrogen or

each Z is nitrogen or

R¹ is —C(O)NR⁷R⁸, —N(H)C(O)R⁹, —C(O)—C₁₋₆alkanediylSR⁹, —NR¹⁰C(O)N(OH)R⁹, —NR¹⁰C(O)C₁₋₆alkanediylSR⁹, —NR¹⁰C(O)C=N(OH)R⁹ or another Zn-chelating-group
  wherein R⁷ and R⁸ are each independently selected from hydrogen, hydroxy, C₁₋₆alkyl, hydroxyC₁₋₆alkyl, aminoC₁₋₆alkyl or aminoaryl;
  R⁹ is independently selected from hydrogen, C₁₋₆alkyl, C₁₋₆alkylcarbonyl, arylC₁₋₆alkyl, C₁₋₆alkylpyrazinyl, pyridinone, pyrrolidinone or methylimidazolyl;
  R¹⁰ is independently selected from hydrogen or C₁₋₆alkyl;
R² is hydrogen, halo, hydroxy, amino, nitro, C₁₋₆alkyl, C₁₋₆alkyloxy, trifluoromethyl, di(C₁₋₆alkyl)amino, hydroxyamino or naphtalenylsulfonylpyrazinyl;
-L- is a direct bond or a bivalent radical selected from C₁₋₆alkanediyl, amino, carbonyl or aminocarbonyl;
each R³ represents a hydrogen atom and one hydrogen atom can be replaced by aryl;
R⁴ is hydrogen, hydroxy, amino, hydroxyC₁₋₆alkyl, C₁₋₆alkyl, C₁₋₆alkyloxy, arylC₁₋₆alkyl, aminocarbonyl, hydroxycarbonyl, aminoC₁₋₆alkyl, aminocarbonylC₁₋₆alkyl, hydroxycarbonylC₁₋₆alkyl, hydroxyaminocarbonyl, C₁₋₆alkyloxycarbonyl, C₁₋₆alkylaminoC₁₋₆alkyl or di(C₁₋₆alkyl)aminoC₁₋₆alkyl;

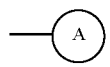

is a radical selected from

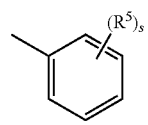 (a-1)

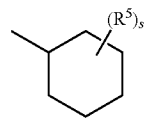 (a-2)

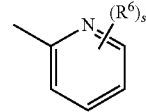 (a-3)

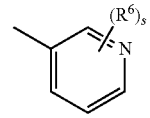 (a-4)

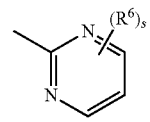 (a-5)

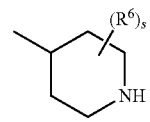 (a-6)

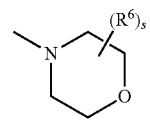 (a-7)

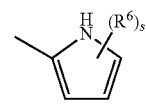 (a-8)

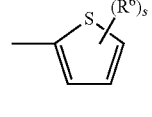 (a-9)

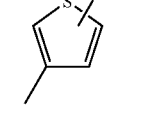 (a-10)

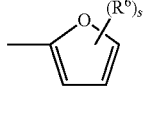 (a-11)

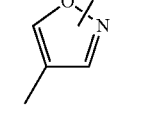 (a-12)

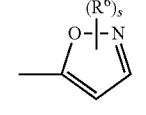 (a-13)

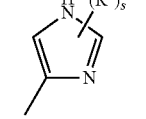 (a-14)

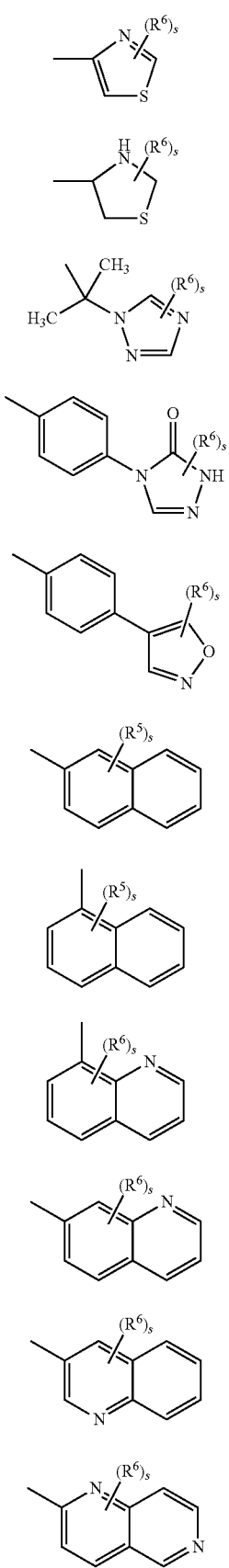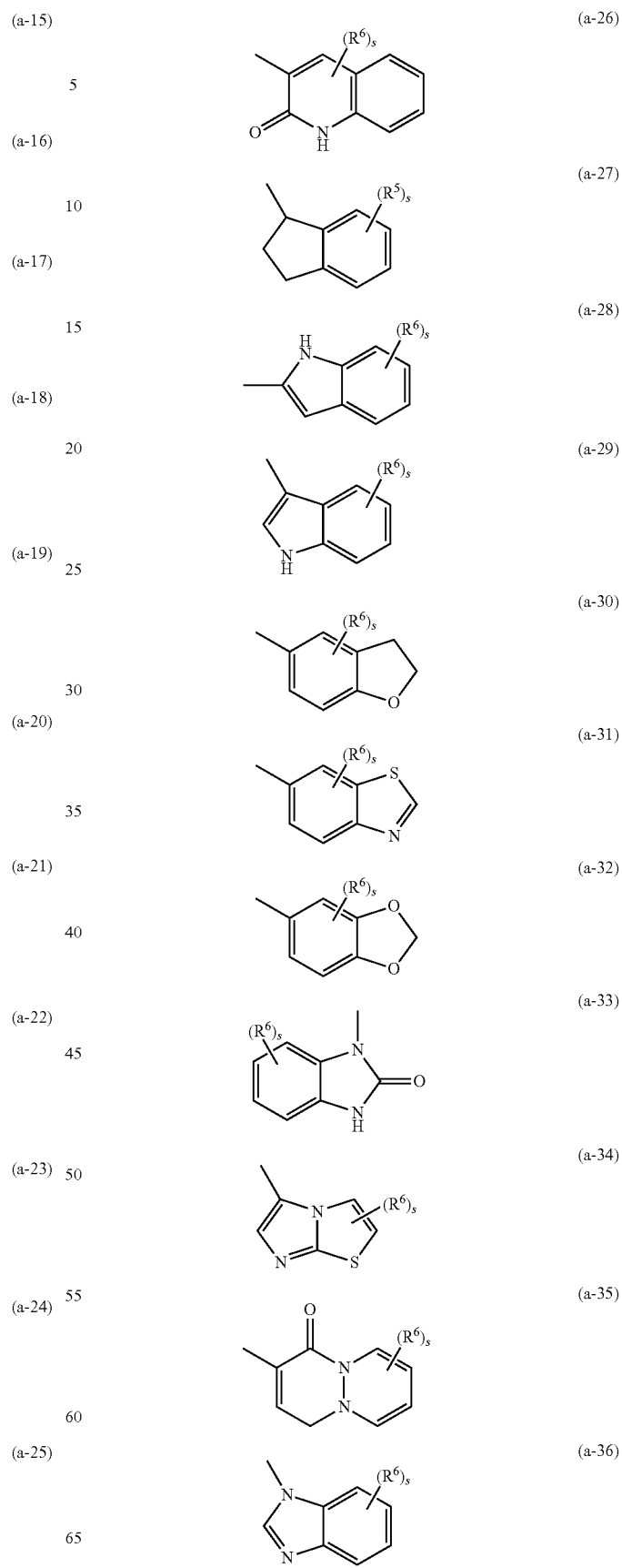

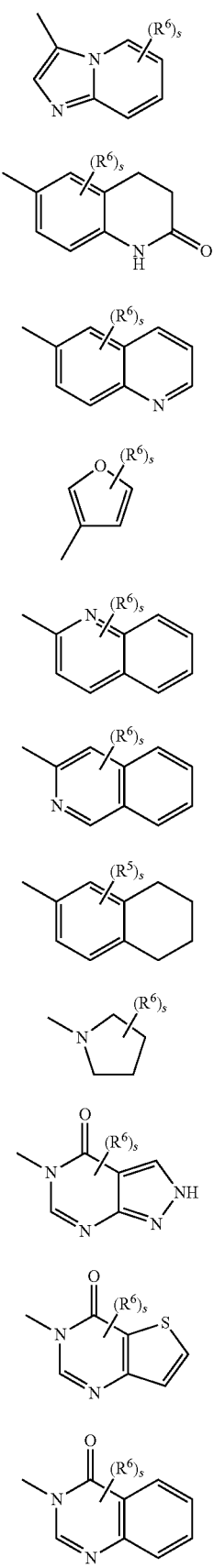
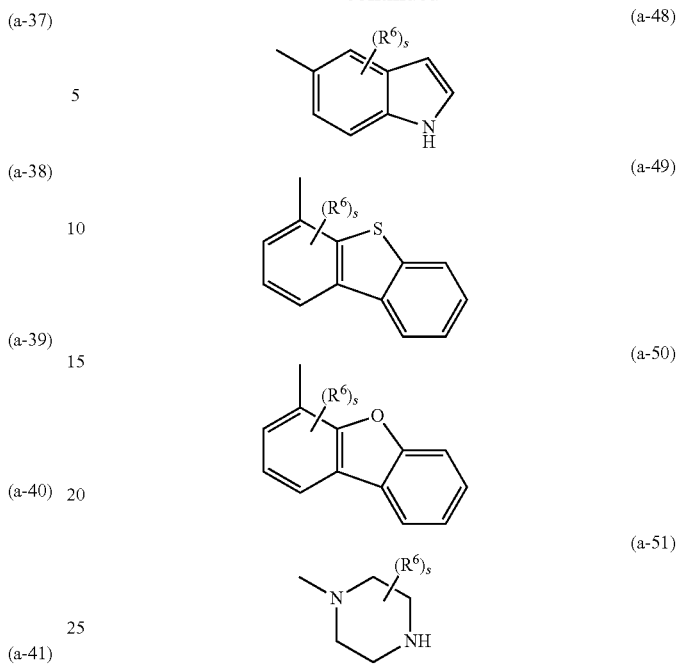

wherein each s is independently 0, 1, 2, 3, 4 or 5;
each $R^5$ and $R^6$ are independently selected from hydrogen; halo; hydroxy; amino; nitro; trihalo$C_{1-6}$alkyl; trihalo$C_{1-6}$alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino ($C_{1-6}$alkyl)amino $C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; amino sulfonylamino ($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl; C$_{1-6}$alkylpiperazinylC$_{1-6}$alkyl; C$_{1-6}$alkylpiperazinylC$_{1-6}$ alkylamino; C$_{1-6}$alkylpiperazinylC$_{1-6}$alkylaminoC$_{1-6}$ alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl) aminosulfonylpiperazinyl; di(C$_{1-6}$alkyl) aminosulfonylpiperazinyl C$_{1-6}$ alkyl; hydroxyC$_{1-6}$ alkylpiperazinyl; hydroxyC$_{1-6}$ alkylpiperazinylC$_{1-6}$alkyl; C$_{1-6}$alkyloxypiperidinyl; C$_{1-6}$alkyloxypiperidinylC$_{1-6}$ alkyl; piperidinylaminoC$_{1-6}$ alkylamino; piperidinylaminoC$_{1-6}$alkylaminoC$_{1-6}$alkyl; (C$_{1-6}$alkylpiperidinyl)(hydroxyC$_{1-6}$alkyl)aminoC$_{1-6}$alkylamino; (C$_{1-6}$alkylpiperidinyl)(hydroxyC$_{1-6}$alkyl)aminoC$_{1-6}$alkylaminoC$_{1-6}$alkyl; hydroxyC$_{1-6}$alkyloxyC$_{1-6}$ alkylpiperazinyl; hydroxyC$_{1-6}$ alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; hydroxyC$_{1-6}$ alkylaminoC$_{1-6}$alkyl; di(hydroxyC$_{1-6}$alkyl)aminoC$_{1-6}$ alkyl; pyrrolidinylC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; tetrahydropyrimidinylpiperazinyl; tetrahydropyrimidinylpiperazinylC$_{1-6}$alkyl; quinolinyl; indolyl; phenyl; phenyl substituted with one, two or three substituents independently selected from halo, amino, nitro, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkylsulfonyl, C$_{1-4}$alkyloxyC$_{1-4}$alkyloxy, C$_{1-4}$alkyloxycarbonyl, aminoC$_{1-4}$alkyloxy, di(C$_{1-4}$alkyl)amino C$_{1-4}$alkyloxy, di(C$_{1-4}$alkyl)amino, di(C$_{1-4}$alkyl)aminocarbonyl, di(C$_{1-4}$alkyl) aminoC$_{1-4}$alkyl, di(C$_{1-4}$alkyl)aminoC$_{1-4}$alkylaminoC$_{1-4}$alkyl, di(C$_{1-4}$alkyl)amino(C$_{1-4}$ alkyl)amino, di(C$_{1-4}$alkyl) amino(C$_{1-4}$alkyl)aminoC$_{1-4}$ alkyl, di(C$_{1-4}$alkyl)aminoC$_{1-4}$ alkyl(C$_{1-4}$alkyl)amino, di(C$_{1-4}$alkyl)aminoC$_{1-4}$alkyl(C$_{1-4}$ alkyl)aminoC$_{1-4}$alkyl, aminosulfonylamino(C$_{1-4}$alkyl) amino, amino sulfonylamino (C$_{1-4}$alkyl)aminoC$_{1-4}$alkyl, di(C$_{1-4}$alkyl)aminosulfonylamino(C$_{1-4}$alkyl)amino, di(C$_{1-4}$alkyl)aminosulfonylamino(C$_{1-4}$alkyl)aminoC$_{1-6}$ alkyl, cyano, piperidinylC$_{1-4}$ alkyloxy, pyrrolidinylC$_{1-4}$ alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$ alkyloxyC$_{1-4}$alkylpiperazinyl, hydroxyC$_{1-4}$alkyloxyC$_{1-4}$ alkylpiperazinylC$_{1-4}$ alkyl, (hydroxyC$_{1-4}$alkyl)(C$_{1-4}$alkyl)amino, (hydroxyC$_{1-4}$ alkyl)(C$_{1-4}$alkyl)aminoC$_{1-4}$alkyl, di(hydroxyC$_{1-4}$alkyl) amino, di(hydroxyC$_{1-4}$alkyl)aminoC$_{1-4}$alkyl, furanyl, furanyl substituted with —CH=CH—CH=CH—, pyrrolidinylC$_{1-4}$alkyl, pyrrolidinylC$_{1-4}$alkyloxy, morpholinyl, morpholinylC$_{1-4}$alkyloxy, morpholinylC$_{1-4}$alkyl, morpholinylC$_{1-4}$alkylamino, morpholinylC$_{1-4}$alkylaminoC$_{1-4}$ alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinylC$_{1-4}$alkyl, C$_{1-4}$alkylpiperazinylC$_{1-4}$alkylamino, C$_{1-4}$alkylpiperazinylC$_{1-4}$alkylaminoC$_{1-6}$alkyl, tetrahydropyrimidinylpiperazinyl, tetrahydropyrimidinylpiperazinylC$_{1-4}$alkyl, piperidinylaminoC$_{1-4}$alkylamino, piperidinylaminoC$_{1-4}$ alkylaminoC$_{1-4}$alkyl, (C$_{1-4}$ alkylpiperidinyl)(hydroxyC$_{1-4}$ alkyl)aminoC$_{1-4}$alkylamino, (C$_{1-4}$alkylpiperidinyl)(hydroxyC$_{1-4}$alkyl)aminoC$_{1-4}$alkylaminoC$_{1-4}$alkyl, pyridinylC$_{1-4}$alkyloxy, hydroxyC$_{1-4}$alkylamino, hydroxyC$_{1-4}$ alkylaminoC$_{1-4}$ alkyl, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino;

the central

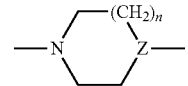

moiety may also be bridged (i.e. forming a bicyclic moiety) with a methylene, ethylene or propylene bridge;

each R$^5$ and R$^6$ can be placed on the nitrogen in replacement of the hydrogen;

aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; C$_{1-6}$alkyl includes C$_{1-4}$alkyl and the higher homologues thereof having 5 to 6 carbon atoms such as, for example, pentyl, 2-methyl-butyl, hexyl, 2-methylpentyl and the like; C$_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihaloC$_{1-6}$alkyl defines C$_{1-6}$alkyl containing three identical or different halo substituents for example trifluoromethyl; C$_{2-6}$alkenediyl defines bivalent straight and branched chain hydrocarbon radicals containing one double bond and having from 2 to 6 carbon atoms such as, for example, ethenediyl, 2-propenediyl, 3-butenediyl, 2-pentenediyl, 3-pentenediyl, 3-methyl-2-butenediyl, and the like; aryl defines phenyl, and phenyl substituted with one or more substituents each independently selected from halo, C$_{1-6}$alkyl, C$_{1-6}$alkyloxy or trifluoromethyl, cyano, hydroxycarbonyl; aminoaryl defines aryl substituted with amino; C$_{3-10}$cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

The term "another Zn-chelating group" refers to a group which is capable of interacting with a Zn-ion, which can be present at an enzymatic binding site.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source.

A first group of interesting compounds consists of those compounds of formula (I) wherein one or more of the following restrictions apply:
a) n is 1 or 2;
b) t is 0, 1 or 2;
c) each Z is nitrogen;
d) $R^{16}$ is hydrogen;
e) $R^2$ is hydrogen, nitro, $C_{1-6}$alkyloxy, trifluoromethyl, di($C_{1-6}$alkyl)amino, hydroxyamino or naphtalenylsulfonylpyrazinyl;
f) -L- is a direct bond or a bivalent radical selected from $C_{1-6}$alkanediyl, carbonyl or aminocarbonyl;
g) each $R^3$ represents a hydrogen atom;
h) $R^4$ is hydrogen, hydroxy$C_{1-6}$alkyl, aminocarbonyl, hydroxyaminocarbonyl or di($C_{1-6}$alkyl)amino$C_{1-6}$alkyl;
i)

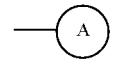

is a radical selected from (a-1), (a-7), (a-9), (a-10), (a-12), (a-14), (a-19), (a-20), (a-21), (a-22), (a-23), (a-30), (a-34), (a-49) or (a-50);
j) each s is independently 0, 1, 2 or 5;
k) each $R^5$ and $R^6$ are independently selected from hydrogen; halo; nitro; trihalo$C_{1-6}$alkyl; trihalo$C_{1-6}$alkyloxy; $C_{1-6}$alkyl; $C_{1-6}$alkyloxy; $C_{1-6}$alkylsulfonyl; (aryl)($C_{1-6}$alkyl)amino; arylsulfonyl; aryloxy; aryl$C_{2-6}$alkenediyl; di($C_{1-6}$alky)amino; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; oxazolyl; pyrrolyl; pyrazolyl; pyridinyl; pyridinyl substituted with $C_{1-6}$alkyloxy; quinolinyl; indolyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, hydroxy$C_{1-4}$alkylpiperazinyl$C_{1-4}$alkyl, hydroxy$C_{1-4}$alkyloxy$C_{1-4}$alkylpiperazinyl$C_{1-4}$alkyl, di(hydroxy$C_{1-4}$alkyl)amino$C_{1-4}$alkyl, pyrrolidinyl$C_{1-4}$alkyl, pyrrolidinyl$C_{1-4}$alkyloxy, morpholinyl$C_{1-4}$alkyloxy, morpholinyl$C_{1-4}$alkyl, $C_{1-4}$alkylpiperazinyl$C_{1-4}$alkyl, or the central

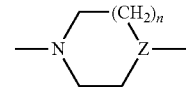

moiety may also be bridged (i.e. forming a bicyclic moiety) with a methylene bridge.

A second group of interesting compounds consists of those compounds of formula (I) wherein one or more of the following restrictions apply:
a) n is 1 or 2;
b) t is 0 or 2;

c) each Z is nitrogen;
d) R¹ is —C(O)NH(OH);
e) R² is hydrogen;
f) -L- is a direct bond;
g) each R³ represents a hydrogen atom;
h) R⁴ is hydrogen;
i)

is a radical selected from (a-1), (a-9), (a-19), (a-20), (a-21), (a-22), (a-23), (a-49) or (a-50);
j) each s is independently 0, 1, 2 or 5;
k) each R⁵ and R⁶ are independently selected from hydrogen; halo; trihaloC$_{1-6}$alkyl; trihaloC$_{1-6}$alkyloxy; C$_{1-6}$alkyl; C$_{1-6}$alkyloxy; arylC$_{2-6}$alkenediyl; di(C$_{1-6}$alky)amino; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl, hydroxyC$_{1-6}$alkylpiperazinylC$_{1-6}$alkyl, hydroxyC$_{1-6}$alkyloxyC$_{1-6}$alkylpiperazinylC$_{1-6}$alkyl, C$_{1-6}$alkyloxypiperidinylC$_{1-6}$alkyl, morpholinylC$_{1-6}$alkyl, hydroxyC$_{1-6}$alkyl(C$_{1-6}$alkyl)aminoC$_{1-6}$alkyl, or di(hydroxyC$_{1-6}$alkyl)aminoC$_{1-6}$alkyl; furanyl; oxazolyl; pyrazolyl; pyridinyl; pyridinyl substituted with C$_{1-6}$alkyloxy; quinolinyl; indolyl; phenyl; phenyl substituted with one, two or three substituents independently selected from halo, amino, C$_{1-6}$alkyl, C$_{1-6}$alkyloxy, hydroxyC$_{1-4}$alkyl, trifluoromethyl, trifluoromethyloxy, di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl(C$_{1-4}$alkyl)aminoC$_{1-4}$alkyl, hydroxyC$_{1-4}$alkylpiperazinylC$_{1-4}$alkyl, hydroxyC$_{1-4}$alkyloxyC$_{1-4}$alkylpiperazinylC$_{1-4}$alkyl, di(hydroxyC$_{1-4}$alkyl)aminoC$_{1-4}$alkyl, pyrrolidinylC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinylC$_{1-4}$alkyl, or the central

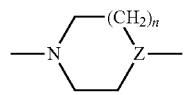

moiety may also be bridged (i.e. forming a bicyclic moiety) with a methylene bridge.

A third group of interesting compounds consists of those compounds of formula (I) wherein one or more of the following restrictions apply:
a) n is 1;
b) t is 0;
c) each Z is nitrogen;
d) R¹ is —C(O)NH(OH);
e) R² is hydrogen;
f) -L- is a direct bond;
g) each R³ represents a hydrogen atom;
h) R⁴ is hydrogen;
i)

is a radical selected from (a-1) or (a-20);

j) each s is independently 0 or 1;
k) each R⁵ and R⁶ are independently selected from hydrogen; thiophenyl; thiophenyl substituted with di(C$_{1-6}$alkyl)aminoC$_{1-6}$alkyl, or C$_{1-6}$alkylpiperazinylC$_{1-6}$alkyl; furanyl; phenyl; phenyl substituted with one substituents independently selected from di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl(C$_{1-4}$alkyl)aminoC$_{1-4}$alkyl, pyrrolidinylC$_{1-4}$alkyl, pyrrolidinylC$_{1-4}$alkyloxy or C$_{1-4}$alkylpiperazinylC$_{1-4}$alkyl.

A fourth group of interesting compounds consists of those compounds of formula (I) wherein R¹ is —C(O)NH(OH) and -L- is a direct bond.

A fifth group of interesting compounds consists of those compounds of formula (I) wherein R¹ is —C(O)NH(OH), R² is hydrogen and -L- is a direct bond.

A sixth group of interesting compounds consists of those compounds of formula (I) wherein one or more of the following restrictions apply;
a) t is 0;
b) R¹ is —C(O)NR²R⁸, —C(O)—C$_{1-6}$alkanediylSR⁹, —NR¹⁰C(O)N(OH)R⁹, —NR¹⁰C(O)C$_{1-6}$alkanediylSR⁹, —NR¹⁰C(O)C=N(OH)R⁹ or another Zn-chelating-group wherein R⁷ and R⁸ are each independently selected from hydrogen, hydroxy, hydroxyC$_{1-6}$alkyl, or aminoC$_{1-6}$alkyl;
c) R² is hydrogen, halo, hydroxy, amino, nitro, C$_{1-6}$alkyl, C$_{1-6}$alkyloxy, trifluoromethyl or di(C$_{1-6}$alkyl)amino;
d) -L- is a direct bond or a bivalent radical selected from C$_{1-6}$alkanediyl, amino or carbonyl;
e) R⁴ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;
f)

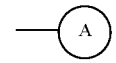

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);
g) each s is independently 0, 1, 2, 3 or 4;
h) R⁵ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoly; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;
i) R⁶ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy;

$C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl
j) the central

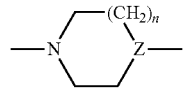

moiety may also be bridged (i.e. forming a bicyclic moiety) with an ethylene bridge.

A seventh group of interesting compounds consists of those compounds of formula (I) wherein one or more of the following restrictions apply:
a) $R^7$ and $R^8$ are each independently selected from hydrogen, hydroxy, hydroxy$C_{1-6}$alkyl, amino$C_{1-6}$alkyl or aminoaryl;
b) $R^2$ is hydrogen, halo, hydroxy, amino, nitro, $C_{1-6}$alkyl, $C_{1-6}$alkyloxy, trifluoromethyl, hydroxyamino or naphtalenylsulfonylpyrazinyl;
c) $R^4$ is hydrogen, hydroxy, amino, hydroxy$C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;
d)

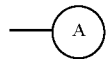

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);
e) each $R^5$ and $R^6$ are independently selected from hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkyloxy$C_{1-6}$alkyloxy; $C_{1-6}$alkylcarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; di($C_{1-6}$alkyl)amino$C_{1-6}$alkyloxy; di($C_{1-6}$alkyl)amino$C_{1-6}$alkylamino; arylsulfonyl; arylsulfonylamino; aryloxy; aryl$C_{2-6}$alkenediyl; di($C_{1-6}$alkyl)amino; cyano; thiophenyl; thiophenyl substituted with di($C_{1-6}$alkyl)amino$C_{1-6}$alkyl ($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl or di(hydroxy$C_{1-6}$alkyl)amino$C_{1-6}$alkyl; furanyl; imidazolyl; $C_{1-6}$alkyltriazolyl; tetrazolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; $C_{1-6}$alkylpiperazinyl$C_{1-6}$alkyloxy; $C_{1-6}$alkylpiperazinyl$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy or aryl; pyrimidinyl; quinolinyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkyloxy$C_{1-4}$alkyloxy, amino$C_{1-4}$alkyloxy, di($C_{1-4}$alkyl)amino$C_{1-4}$alkyloxy, di($C_{1-4}$alkyl)amino, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, pyrrolidinyl$C_{1-4}$alkyloxy, morpholinyl$C_{1-4}$alkyloxy, morpholinyl$C_{1-4}$alkyl, $C_{1-4}$alkylpiperazinyl$C_{1-4}$alkyloxy, $C_{1-4}$alkylpiperazinyl$C_{1-4}$alkyl, hydroxy$C_{1-4}$alkylamino, di(hydroxy$C_{1-4}$alkyl)amino, di($C_{1-4}$alkyl)amino$C_{1-4}$alkylamino, aminothiadiazolyl, aminosulfonylpiperazinyl$C_{1-4}$alkyloxy, or thiophenyl$C_{1-4}$alkylamino A group of preferred compounds consists of those compounds of formula (I) wherein
$R^7$ and $R^8$ are each independently selected from hydrogen, hydroxy, hydroxy$C_{1-6}$alkyl, amino$C_{1-6}$alkyl or aminoaryl;
$R^2$ is hydrogen, halo, hydroxy, amino, nitro, $C_{1-6}$alkyl, $C_{1-6}$alkyloxy, trifluoromethyl, hydroxyamino or naphtalenylsulfonylpyrazinyl;
$R^4$ is hydrogen, hydroxy, amino, hydroxy$C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;

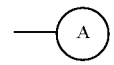

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);
each $R^5$ and $R^6$ are independently selected from hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkyloxy$C_{1-6}$alkyloxy; $C_{1-6}$alkylcarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; di($C_{1-6}$alkyl)amino$C_{1-6}$alkyloxy; di($C_{1-6}$alkyl)amino$C_{1-6}$alkylamino; arylsulfonyl; arylsulfonylamino; aryloxy; aryl$C_{2-6}$alkenediyl; di($C_{1-6}$alkyl)amino; cyano; thiophenyl; thiophenyl substituted with di($C_{1-6}$alkyl)amino$C_{1-6}$alkyl ($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl or di(hydroxy$C_{1-6}$alkyl)amino$C_{1-6}$alkyl; furanyl; imidazolyl; $C_{1-6}$alkyltriazolyl;

tetrazolyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; phenyl; phenyl substituted with one, two or three substituents independently selected from halo, amino, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino.

Another group of preferred compounds consists of those compounds of formula (I) wherein t is 0;
$R^1$ is —C(O)NR$^7$R$^8$, —C(O)—C$_{1-6}$alkanediylSR$^9$, —NR$^{10}$C(O)N(OH)R$^9$, —NR$^{10}$C(O)C$_{1-6}$alkanediylSR$^9$, —NR$^{10}$C(O)C=N(OH)R$^9$ or another Zn-chelating-group wherein R$^7$ and R$^8$ are each independently selected from hydrogen, hydroxy, hydroxyC$_{1-6}$alkyl, or aminoC$_{1-6}$alkyl;
$R^2$ is hydrogen, halo, hydroxy, amino, nitro, C$_{1-6}$alkyl, C$_{1-6}$alkyloxy, trifluoromethyl or di(C$_{1-6}$alkyl)amino;
-L- is a direct bond or a bivalent radical selected from C$_{1-6}$alkanediyl, amino or carbonyl;
$R^4$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

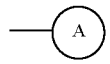

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);

each s is independently 0, 1, 2, 3 or 4;
$R^5$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoly; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;
$R^6$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently selected from halo, C$_{1-6}$alkyl, C$_{1-6}$alkyloxy or trifluoromethyl; or the central

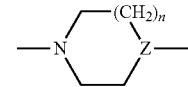

moiety may also be bridged (i.e. forming a bicyclic moiety) with an ethylene bridge.

An even further group of preferred compounds consists of those compounds of formula (I) wherein n is 1 or 2; t is 0, 1 or 2; each Z is nitrogen; $R^{10}$ is hydrogen; $R^2$ is hydrogen, nitro, C$_{1-6}$alkyloxy, trifluoromethyl, di(C$_{1-6}$alkyl)amino, hydroxyamino or naphtalenylsulfonylpyrazinyl; -L- is a direct bond or a bivalent radical selected from C$_{1-6}$alkanediyl, carbonyl or aminocarbonyl; each $R^3$ represents a hydrogen atom; $R^4$ is hydrogen, hydroxyC$_{1-6}$alkyl, aminocarbonyl, hydroxyaminocarbonyl or di(C$_{1-6}$alkyl)aminoC$_{1-6}$alkyl;

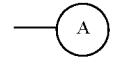

is a radical selected from (a-1), (a-7), (a-9), (a-10), (a-12), (a-14), (a-19), (a-20), (a-21), (a-22), (a-23), (a-30), (a-34), (a-49) or (a-50); each s is independently 0, 1, 2 or 5; each $R^5$ and $R^6$ are independently selected from hydrogen; halo; nitro; trihaloC$_{1-6}$alkyl; trihaloC$_{1-6}$alkyloxy; C$_{1-6}$alkyl; C$_{1-6}$alkyloxy; C$_{1-6}$alkylsulfonyl; (aryl)(C$_{1-6}$alkyl)amino; arylsulfonyl; aryloxy; arylC$_{2-6}$alkenediyl; di(C$_{1-6}$alky$_3$)amino; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl, hydroxyC$_{1-6}$alkylpiperazinylC$_{1-6}$alkyl, hydroxyC$_{1-6}$alkyloxyC$_{1-6}$alkylpiperazinylC$_{1-6}$alkyl, di(C$_{1-6}$alkyl)aminosulfonylpiperazinylC$_{1-6}$alkyl, C$_{1-6}$alkyloxypiperidinylC$_{1-6}$alkyl, morpholinylC$_{1-6}$alkyl, hydroxyC$_{1-6}$alkyl(C$_{1-6}$alkyl)aminoC$_{1-6}$alkyl, or di(hydroxyC$_{1-6}$alkyl)aminoC$_{1-6}$alkyl; furanyl; oxazolyl; pyrrolyl; pyrazolyl; pyridinyl; pyridinyl substituted with C$_{1-6}$alkyloxy; quinolinyl; indolyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, hydroxy$C_{1-4}$alkylpiperazinyl$C_{1-4}$alkyl, hydroxy$C_{1-4}$alkyloxy$C_{1-4}$alkylpiperazinyl$C_{1-4}$alkyl, di(hydroxy$C_{1-4}$alkyl)amino$C_{1-4}$alkyl, pyrrolidinyl$C_{1-4}$alkyl, pyrrolidinyl$C_{1-4}$alkyloxy, morpholinyl$C_{1-4}$alkyloxy, morpholinyl$C_{1-4}$alkyl, $C_{1-4}$alkylpiperazinyl$C_{1-4}$alkyl, or the central

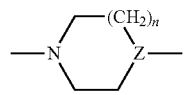

moiety may also be bridged (i.e. forming a bicyclic moiety) with a methylene bridge.

A group of more preferred compounds consists of those compounds of formula (I) wherein n is 1 or 2; t is 0 or 2; each Z is nitrogen; $R^1$ is —C(O)NH(OH); $R^2$ is hydrogen; -L- is a direct bond; each $R^3$ represents a hydrogen atom; $R^4$ is hydrogen;

is a radical selected from (a-1), (a-9), (a-19), (a-20), (a-21), (a-22), (a-23), (a-49) or (a-50); each s is independently 0, 1, 2 or 5; each $R^5$ and $R^6$ are independently selected from hydrogen; halo; trihalo$C_{1-6}$alkyl; trihalo$C_{1-6}$alkyloxy; $C_{1-6}$alkyl; $C_{1-6}$alkyloxy; aryl$C_{2-6}$alkenediyl; di($C_{1-6}$alky)amino; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; oxazolyl; pyrazolyl; pyridinyl; pyridinyl substituted with $C_{1-6}$alkyloxy; quinolinyl; indolyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino$C_{1-4}$alkyl, hydroxy$C_{1-4}$alkylpiperazinyl$C_{1-4}$alkyl, hydroxy$C_{1-4}$alkyloxy$C_{1-4}$alkylpiperazinyl$C_{1-4}$alkyl, di(hydroxy$C_{1-4}$alkyl)amino$C_{1-4}$alkyl, pyrrolidinyl$C_{1-4}$alkyl, pyrrolidinyl$C_{1-4}$alkyloxy, morpholinyl$C_{1-4}$alkyloxy, morpholinyl$C_{1-4}$alkyl, $C_{1-4}$alkylpiperazinyl$C_{1-4}$alkyl, or the central

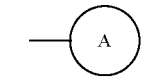

moiety may also be bridged (i.e. forming a bicyclic moiety) with a methylene bridge.

A group of even more preferred compounds consists of those compounds of formula (I) wherein n is 1; t is 0; each Z is nitrogen; $R^1$ is —C(O)NH(OH); $R^2$ is hydrogen; -L- is a direct bond; each $R^3$ represents a hydrogen atom; $R^4$ is hydrogen;

—A is a radical selected from (a-1) or (a-20); each s is independently 0 or 1; each $R^5$ and $R^6$ are independently selected from hydrogen; thiophenyl; thiophenyl substituted with di($C_{1-6}$alkyl)amino $C_{1-6}$alkyl, or $C_{1-6}$alkylpiperazinyl$C_{1-6}$alkyl; furanyl; phenyl; phenyl substituted with one substituents independently selected from di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino$C_{1-4}$alkyl, pyrrolidinyl$C_{1-4}$alkyl, pyrrolidinyl$C_{1-4}$alkyloxy or $C_{1-4}$alkylpiperazinyl$C_{1-4}$alkyl.

Most preferred compounds are compounds No. 6, No. 100, No. 104, No. 128, No. 144, No. 124, No. 154, No. 125, No. 157, No. 156, No. 159, No. 163, No. 164, No. 168, No. 169, No. 127, No. 171, No. 170, No. 172 and No. 173.

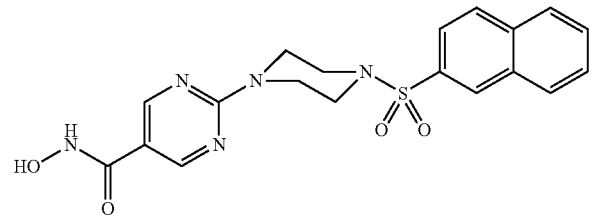

Co. No. 6

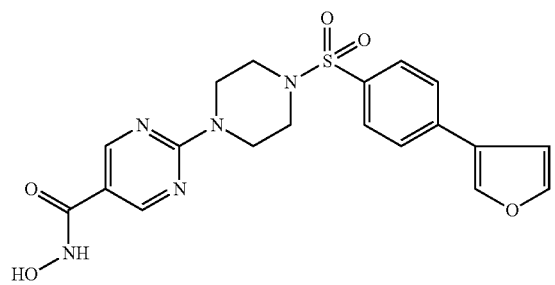

Co. No. 100

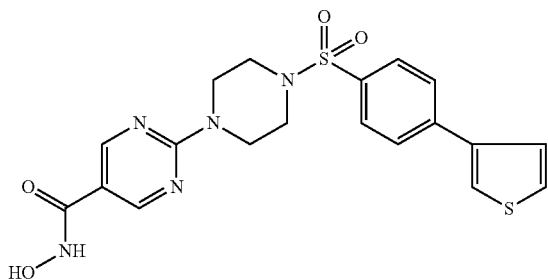
Co. No. 104
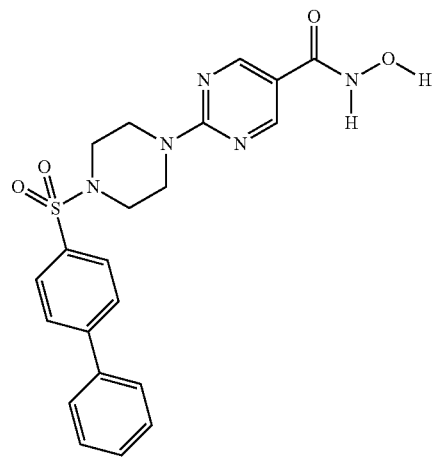
Co. No. 128
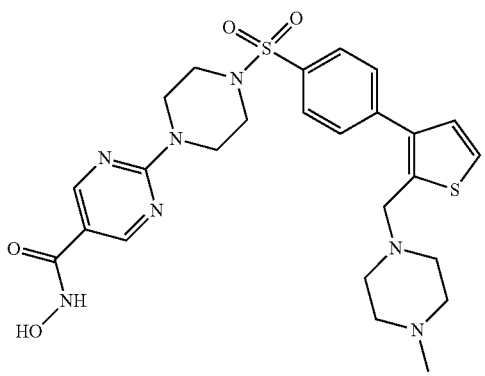
•0.65 H₂O•C₂HF₃O₂; Co. No. 144
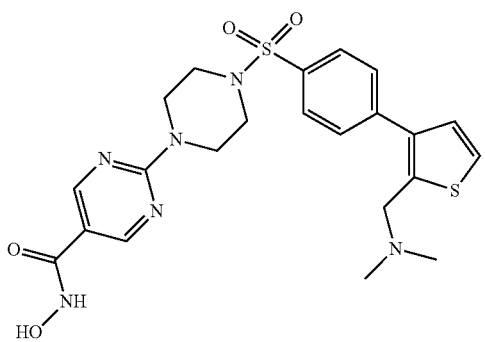
•C₂HF₃O₂; Co. No. 124

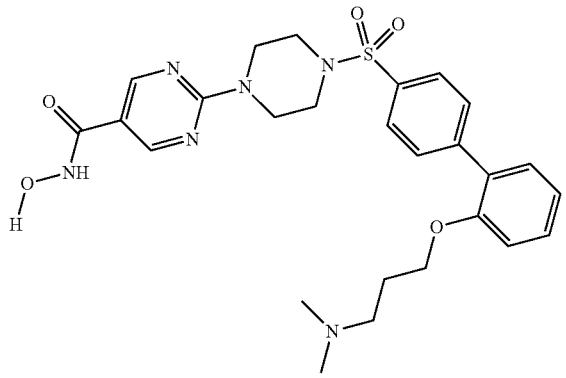
•0.6 H$_2$O•C$_2$HF$_3$O$_2$; Co. No. 154
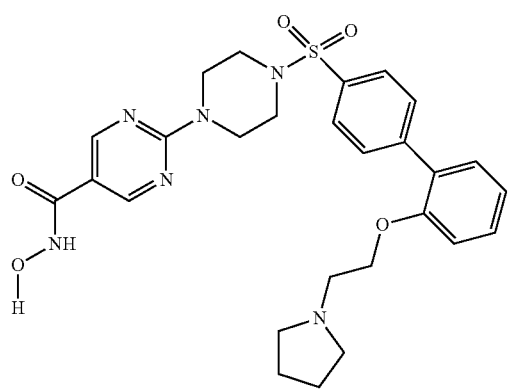
•0.2 H$_2$O•C$_2$HF$_3$O$_2$; Co. No. 125
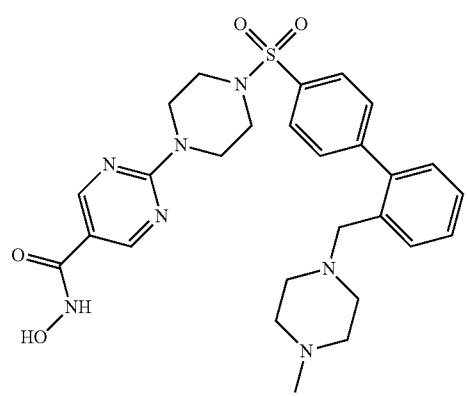
•0.5 H$_2$O •1.2 C$_2$HF$_3$O$_2$; Co. No. 157

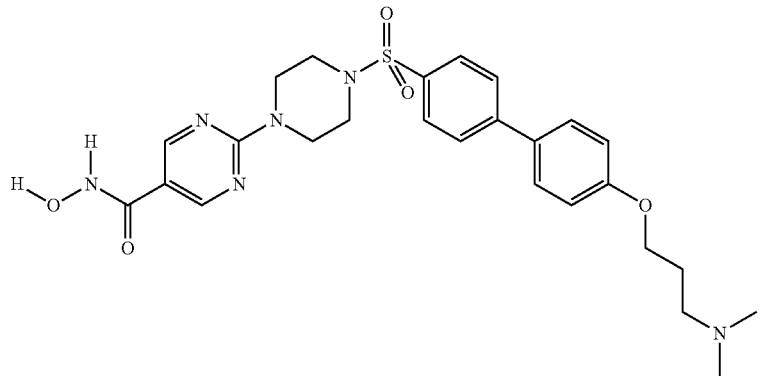
•0.3 H₂O •1.2 C₂HF₃O₂; Co. No. 156
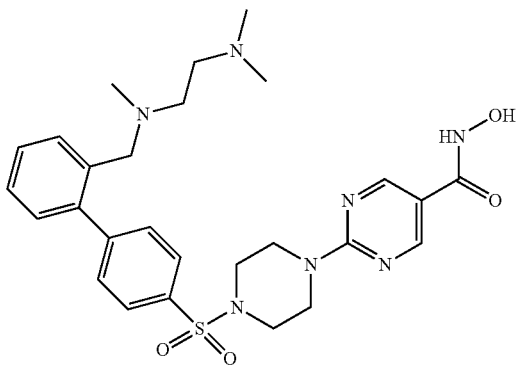
•0.3 H₂O •1.5 C₂HF₃O₂; Co. No. 159
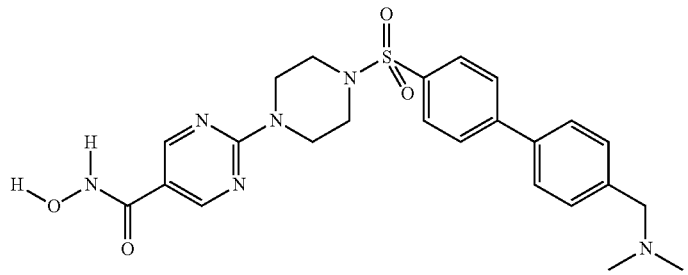
•0.6 H₂O •C₂HF₃O₂; Co. No. 163
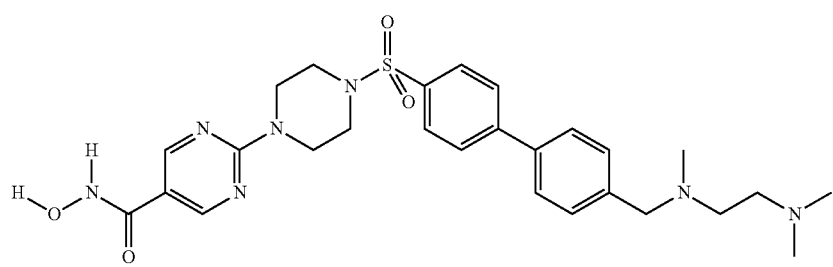
•0.7 H₂O •1.5 C₂HF₃O₂; Co. No. 164

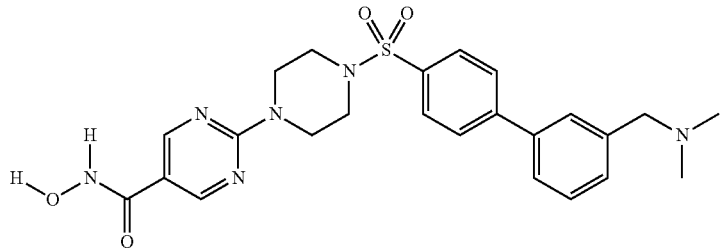
•C₂HF₃O₂; Co. No. 168
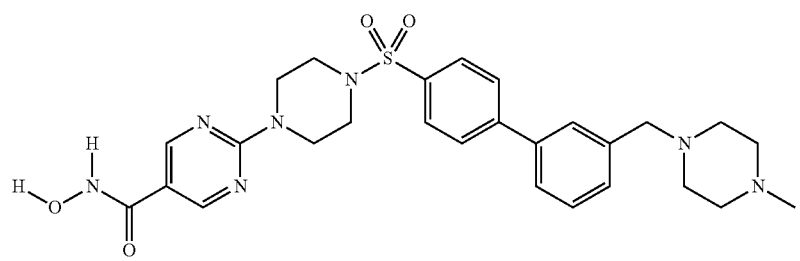
•1.1 C₂HF₃O₂; Co. No. 169
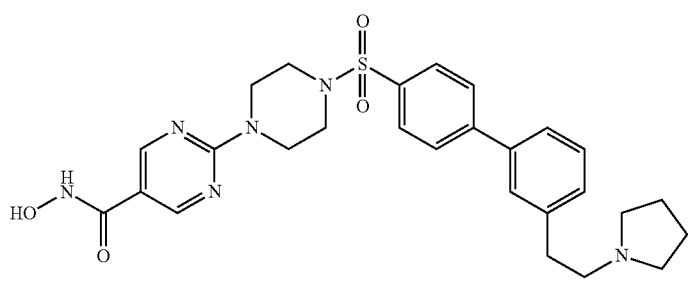
•1.16 C₂HF₃O₂; Co. No. 127
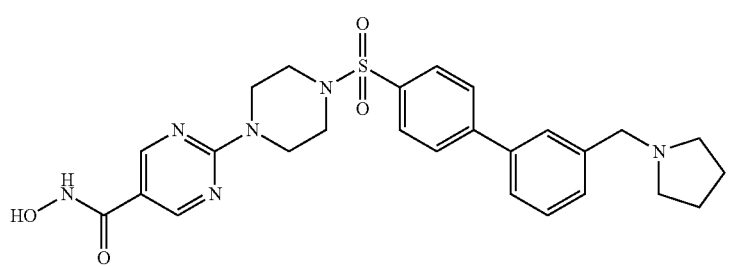
•1.03 C₂HF₃O₂; Co. No. 171
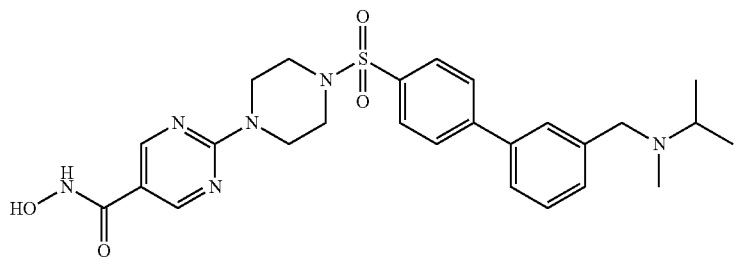
•0.94 C₂HF₃O₂; Co. No. 170

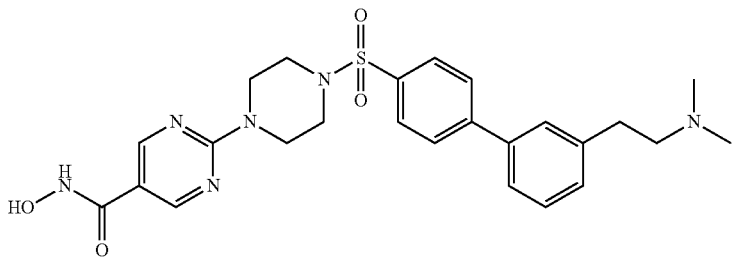

•1.18 C$_2$HF$_3$O$_2$; Co. No. 172

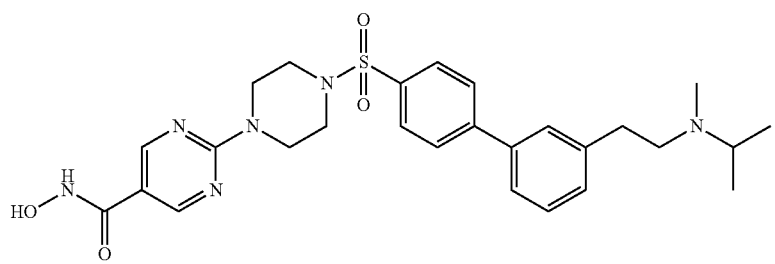

•1.17 C$_2$HF$_3$O$_2$; Co. No. 173

Most preferred compound is compound No 6.

Compound 6

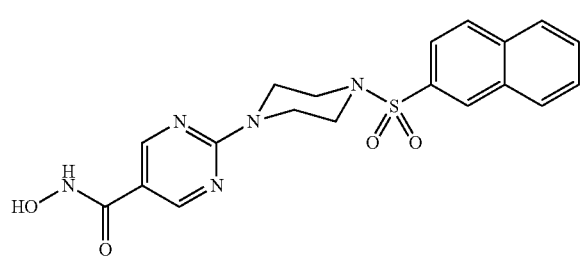

The compounds of formula (I) and their pharmaceutically acceptable salts and N-oxides and stereochemically isomeric forms thereof may be prepared in conventional manner. A number of general synthesis routes are encompassed as examples:

1a) Hydroxamic acids of formula (I) wherein R$^1$ is —C(O)NH(OH), said compounds being referred to as compounds of formula (I-a), may be prepared by reacting an intermediate of formula (II) with an appropriate acid, such as for example, trifluoro acetic acid. Said reaction is performed in an appropriate solvent, such as, for example, methanol.

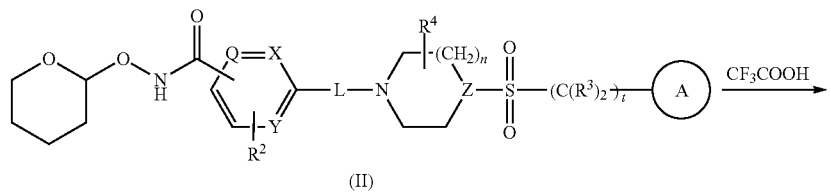

(II)

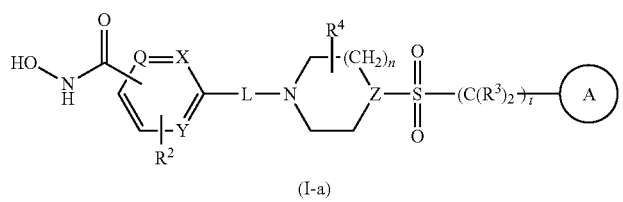

(I-a)

1b) intermediates of formula (II) may be prepared by reacting an intermediate of formula (III) with an intermediate of formula (IV) in the presence of appropriate reagents such as N-(ethylcarbonimidoyl)-N,N-dimethyl-1,3-propanediamine, monohydrochloride (EDC) and 1-hydroxy-1H-benzotriazole (HOBT). The reaction may be performed in a suitable solvent such as a mixture of DCM and THF.

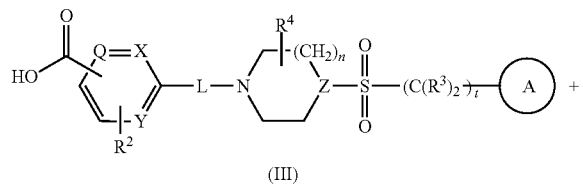

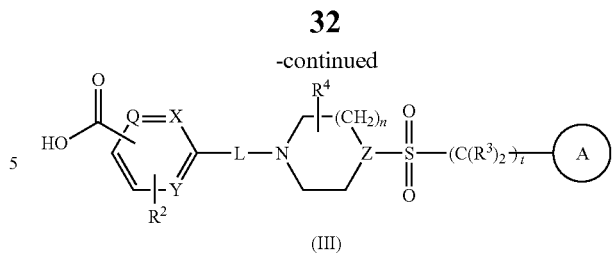

2) Hydroxamic acids of formula (I) wherein $R^1$ is —C(O)NH(OH), said compounds being referred to as compounds of formula (I-a), may also be prepared by catalytic hydrogenation of an intermediate of formula (VI) with hydrogen in the presence of a catalyst, such as, for example, palladium on carbon (10%). Said reaction is performed in an appropriate solvent, such as, for example, dimethylformamide (DMF) or THF. Alternatively these compounds may also be prepared by reacting an intermediate of formula (VI) with cyclohexadiene in the presence of a catalyst, such as, for example palladium on carbon (10%). Said reaction is performed in an appropriate solvent, such as, for example, 1-propanol.

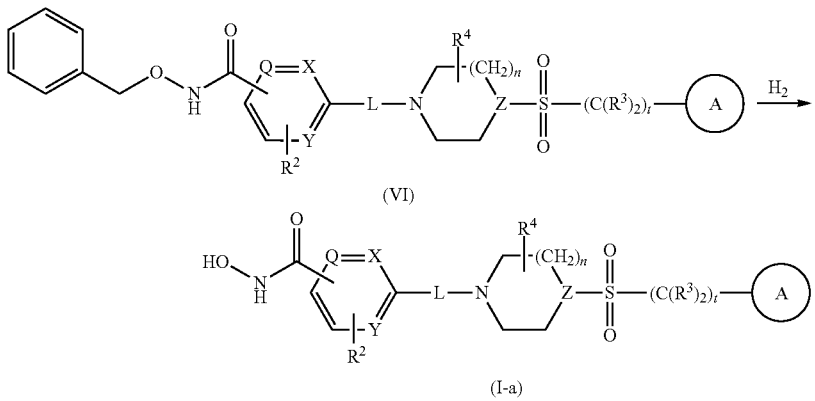

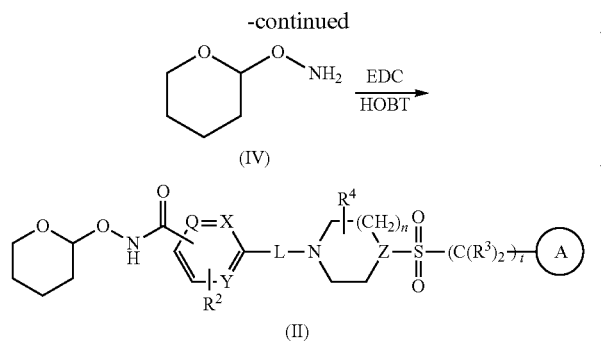

1c) intermediates of formula (III) may be prepared by reacting an intermediate of formula (V) with an appropriate base such as NaOH in the presence of a suitable solvent such as ethanol.

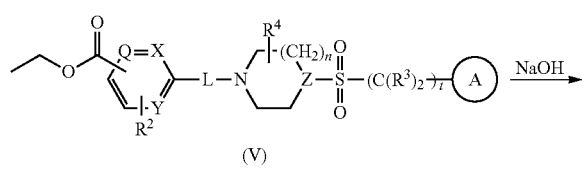

3) Compounds of formula (I) wherein $R^1$ is

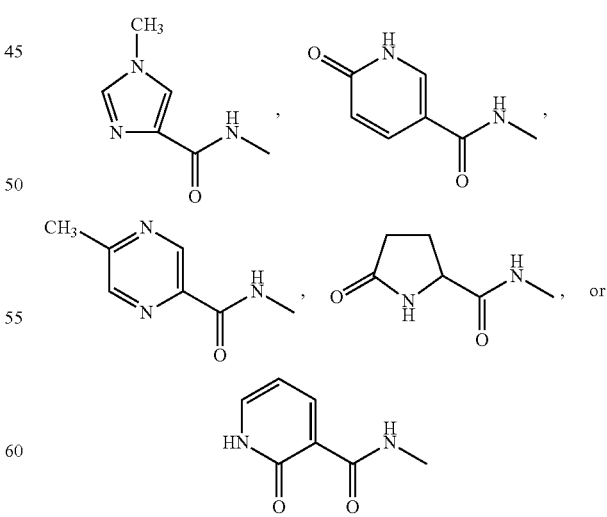

said compounds being referred to as compounds of formula (I-b), may be prepared by reacting an intermediate of formula (VII) with an intermediate of formula (VIII)

wherein R' is

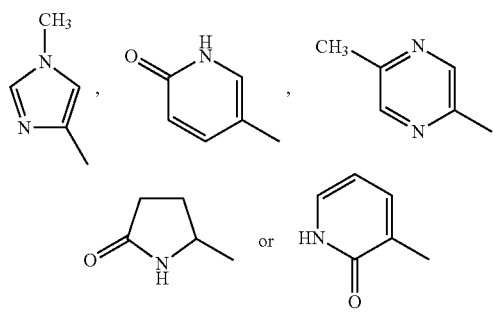

in the presence of N-(ethylcarbonimidoyl)-N,N-dimethyl-1,
3-propanediamine, monohydrochloride (EDC) and hydroxybenzotriazole (HOBT). Said reaction is performed in an appropriate solvent, such as, for example, a mixture of dichloromethane (DCM) and THF.

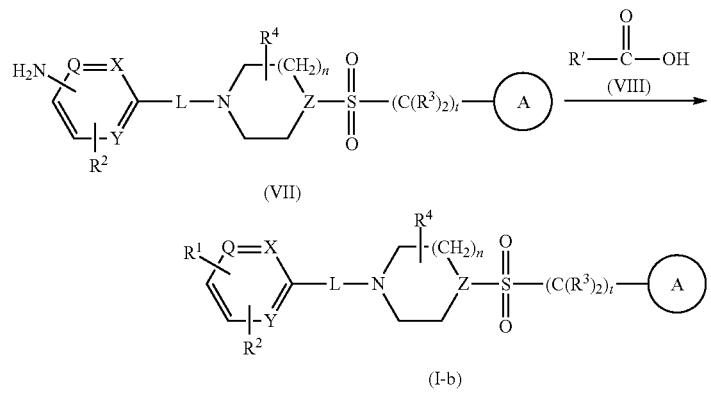

The compounds of formula (I) can also conveniently be prepared using solid phase synthesis techniques. In general, solid phase synthesis involves reacting an intermediate in a synthesis with a polymer support. This polymer-supported intermediate can then be carried on through a number of synthesis steps. After each step, filtering the resin and washing it numerous times with various solvents remove impurities. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry is described in for example "The Combinatorial Index" (B. Bunin, Academic Press) and Novabiochem's 1999 Catalogue & Peptide Synthesis Handbook (Novabiochem AG, Switzerland) both incorporated herein by reference.

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:

a) the sensitisation of tumours to radiotherapy by administering the compound according to the invention before, during or after irradiation of the tumour for treating cancer;
b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;
c) inhibiting smooth muscle cell proliferation including vascular proliferative disorders, atherosclerosis and restenosis;
d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia greata, scleroderma, exanthema, eczema, dermatomyositis, acne, diabetes, systemic lupus erythematosus, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating a cardiac dysfunction;
h) inhibiting immunosuppressive conditions such as the treatment of HIV infections;
i) treating renal dysfunction;
j) suppressing endocrine disorders;
k) inhibiting dysfunction of gluconeogenesis;
l) treating a neuropathology for example Parkinson's disease or a neuropathology that results in a cognitive disorder, for example, Alzheimer's disease or polyglutamine related neuronal diseases;
m) inhibiting a neuromuscular pathology, for example, amylotrophic lateral sclerosis;
n) treating spinal muscular atrophy;
o) treating other pathologic conditions amenable to treatment by potentiating expression of a gene;
p) enhancing gene therapy.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

- platinum coordination compounds for example cisplatin, carboplatin or oxalyplatin;
- taxane compounds for example paclitaxel or docetaxel;
- topoisomerase I inhibitors such as camptothecin compounds for example irinotecan or topotecan;
- topoisomerase II inhibitors such as anti-tumour podophyllotoxin derivatives for example etoposide or teniposide;
- anti-tumour vinca alkaloids for example vinblastine, vincristine or vinorelbine;
- anti-tumour nucleoside derivatives for example 5-fluorouracil, gemcitabine or capecitabine;
- alkylating agents such as nitrogen mustard or nitrosourea for example cyclophosphamide, chlorambucil, carmustine or lomustine;
- anti-tumour anthracycline derivatives for example daunorubicin, doxorubicin, idarubicin or mitoxantrone;
- HER2 antibodies for example trastuzumab;
- estrogen receptor antagonists or selective estrogen receptor modulators for example tamoxifen, toremifene, droloxifene, faslodex or raloxifene;
- aromatase inhibitors such as exemestane, anastrozole, letrazole and vorozole;
- differentiating agents such as retinoids, vitamin D and retinoic acid metabolism blocking agents (RAMBA) for example accutane;
- DNA methyl transferase inhibitors for example azacytidine;
- kinase inhibitors for example flavoperidol, imatinib mesylate or gefitinib;
- farnesyltransferase inhibitors; or
- other HDAC inhibitors.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumor vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affiniity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis)

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:
- short-chain fatty acids for example butyrate, 4-phenylbutyrate or valproic acid;
- hydroxamic acids for example suberoylanilide hydroxamic acid (SAHA), biaryl hydroxamate A-161906, bicyclic aryl-N-hydroxycarboxamides, pyroxamide, CG-1521, PXD-101, sulfonamide hydroxamic acid, LAQ-824, trichostatin A (TSA), oxamflatin, scriptaid, m-carboxy cinnamic acid bishydroxamic acid, or trapoxin-hydroxamic acid analogue;
- cyclic tetrapeptides for example trapoxin, apidicin or depsipeptide;
- benzamides for example MS-275 or CI-994, or depudecin.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination according to the invention of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumor podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumor vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumor nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumor anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

Trastuzumab is advantageously administered in a dosage of 1 to 5 mg per square meter ($mg/m^2$) of body surface area, particularly 2 to 4 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

EXPERIMENTAL PART

The following examples are provided for purposes of illustration.

Hereinafter "AMMC" means 3-[2-(N,N-diethyl-N-methylamino)ethyl]-7-methoxy-4-methylcoumarin, "BFC" means benzyloxy-trifluoromethyl coumarin, "BINAP" means 2,2'-bis(diphenylphosphino)-1,1'-binaphtyl, "Boc" means tertiary butoxycarbonyl, "BuLi" means n-butyl lithium, "BTEAC" means benzyltriethylammonium chloride, "BSA" means bovine serum albumine, "DCM" means dichloromethane, "DIC" means diisopropylcarbodiimide, "DIEA" means diisopropylethylamine, "DIPE" means diisopropylether, "DMAP" means dimethylaminopyridine, "DMF" means dimethylformamide, "DMSO" means dimethylsulfoxide, 'EDC' means N'-(ethylcarbonimidoyl)-N,N-dimethyl-1,3-propanediamine, monohydrochloride, "EDTA" means etylenediaminetetraacetic acid, "EtOAc" means ethyl acetate, "Fmoc" means fluorenylmethoxycarbonyl, "Hepes" means 4-(-2-hydroxyethyl)-1-piperazine-ethanesulfonic acid, "HOAc" means acetic acid, "MeOH" means methanol, "MTT" means 3-(4,5-dimethylthiazol-2-yl)-2,5-diphenyl-2H-tetrazolium bromide, "NMP" means N-methylpyrrolidinone, "PBS" means phosphate buffered saline, "PyBop" means benzotriazole-1-yl-oxy-tris-pyrrolidino-phosphonium hexafluorophosphate, "PyBrOP" means bromo-tris-pyrrolidino-phosphonium hexafluorophosphate, "TEA" means triethylamine, "TFA" means trifluoroacetic acid, "TIS" means triisopropylsilane, "THF" means tetrahydrofuran, "THP" means tetrahydropyranyl and "TMSOTf" means trimethylsilyl triflate. Extrelut™ is a product of Merck KgaA, Darmstadt, Germany, and is a short column comprising diatomaceous earth. Flashtube™ is a product of Trikonex and is a polyethylene tube packed with 8.0 g of silica containing a fluorescence indicator.

A. PREPARATION OF THE INTERMEDIATES

Example A1 a) A mixture of 4-(hexahydro-1H-1,4-diazepin-1-yl)-benzoic acid, ethyl ester hydrochloride (1:2) (0.01 mol) and 2-naphthalenesulfonyl chloride (0.011 mol) in DCM p.a. (150 ml) was stirred at room temperature. NaHCO$_3$ (saturated aqueous solution, 50 ml) was added and the reaction mixture was stirred for 4 hours at room temperature. The layers were separated. The organic layer was dried, filtered and the solvent evaporated. The residue was triturated under 2-propanol, filtered off and dried, yielding 4.5 g (quantitative yield) of 4-[hexahydro-4-(2-naphthalenylsulfonyl)-1H-1,4-diazepin-1-yl]-benzoic acid, ethyl ester (interm. 1).

b) A mixture of interm. 1 (0.0091 mol) in HCl 35% (10 ml) and 1,4-dioxane (30 ml) was stirred and refluxed for 24 hours, then cooled and the resulting precipitate was filtered off, washed with dioxane, and dried. A part (0.9 g) of the residue (3.9 g, 96%) was recrystallized from ethanol with a small amount of DMF, filtered off and dried, yielding 0.43 g of 4-[hexahydro-4-(2-naphthalenylsulfonyl)-1H-1,4-diazepin-1-yl]-benzoic acid (interm. 2).

c) A mixture of interm. 2 (0.0067 mol), O-(phenylmethyl)-hydroxylamine, hydrochloride (2 equiv, 0.0134 mol), 4-methylmorpholine (4 equiv, 0.027 mol) and DMAP (0.5 g) in DCM p.a. (200 ml) was stirred at room temperature. DIC (2 equiv, 0.0134 mol) was added and the reaction mixture was stirred for 2 hours at room temperature. The solvent was evaporated. The residue was triturated under ethanol, filtered off and dried. The residue was purified over silica gel on a glass filter (eluent: DCM/MeOH 99/1). The desired fractions were collected and the solvent was evaporated. The residue was triturated under DCM (30 ml), filtered off and dried, yielding 1.9 g (55%) of 4-[hexahydro-4-(2-naphthalenylsulfonyl)-1H-1,4-diazepin-1-yl]-N-(phenylmethoxy)-benzamide (interm. 3).

Example A2 a) A mixture of 4-(4-carboxyphenyl)-1-piperazinecarboxylic acid, 1-(1,1-dimethylethyl) ester (0.032 mol), O-(phenylmethyl)-hydroxylamine hydrochloride (0.064 mol), DMAP (0.03 mol) in DCM p.a. (250 ml) and TEA (14 ml) was stirred at room temperature. DIC (0.064 mol) was added. The reaction mixture was stirred at room temperature for 8 hours, then washed with water, HCl (0.5N) and water. The separated organic layer was dried (MgSO$_4$), filtered and the solvent was evaporated. The residue was purified by column chromatography over silica gel (eluent: DCM/MeOH 98/2). The desired fractions were collected and the solvent was evaporated, yielding 13.7 g of 4-[4-[[(phenylmethoxy)amino]carbonyl]phenyl]-1-piperazinecarboxylic acid, 1,1-dimethylethyl ester (interm. 4).

b) A mixture of interm. 4 (0.0137 mol) in TFA (57 ml) and DCM (300 ml) was stirred at room temperature for 2 hours. The solvent was evaporated. The residue was taken up in water/DCM and alkalized with NH$_4$OH. The separated aqueous layer was saturated with NaCl and extracted with DCM. The combined organic layer was dried (MgSO$_4$), filtered and the solvent was evaporated. The residue was suspended in DIPE. The precipitate was filtered off and dried, yielding 1.6 g (37.6%) of N-(phenylmethoxy)-4-(1-piperazinyl)-benzamide (interm. 5).

c) A mixture of interm. 5 (0.011 mol) in DCM (150 ml) and TEA (1.75 ml) was stirred at room temperature. 2-Naphthalenesulfonyl chloride (0.013 mol) was dissolved in DCM (10 ml) and added drop wise to the reaction mixture. The reaction mixture was stirred at room temperature for 30 minutes, and then washed with water. The separated organic layer was dried (MgSO$_4$), filtered and the solvent was evaporated. The residue was suspended in DIPE. The precipitate was filtered off and dried, yielding 3.6 g of 4-[4-(2-naphthalenylsulfonyl)-1-piperazinyl]-N-(phenylmethoxy)-benzamide (interm. 6).

Example A3

A mixture of 1-(2-naphtalenylsulfonyl)-4-(4-nitrophenyl)-piperazine (7.5 mmol) in THF (150 ml) was hydrogenated at 50° C. with Pd/C 10% (1 g) as a catalyst in the presence of thiophene solution (0.5 ml). After uptake of H$_2$ (3 equiv.), the catalyst was filtered off and the filtrate was evaporated. The residue was crystallized from 2-propanol. The formed precipitate was filtered off, washed with 2-propanol and dried (55° C., vacuum), yielding 2.39 g (87%) of 1-(4-aminophenyl)-4-(2-naphthalenylsulfonyl)-piperazine (interm. 7).

Example A4 a) NaH 60% (0.0217 mol) was added portionwise at room temperature to a solution of 1-(2-naphtalenesulfonyl)-piperazine (0.011 mol) in THF (50 ml) under N$_2$ flow. The mixture was stirred at room temperature for 1 hour, then cooled to 0° C. A solution of 2-(methylsulfonyl)-5-pyrimidinecarboxylic acid, ethyl ester (0.014 mol) in THF (30 ml) was added quickly. The mixture was stirred at room temperature for 2 hours, poured out into water and extracted with EtOAc. The organic layer was separated, dried (MgSO$_4$), filtered, and the solvent was evaporated. The residue was taken up in diethyl ether. The precipitate was filtered off and dried, yielding 3.92 g (84%) of 2-[4-(2-naphthalenylsulfonyl)-1-piperazinyl]-5-pyrimidinecarboxylic acid, ethyl ester (interm. 8), melting point>260° C.

b) A mixture of interm. 8 (0.0011 mol) and potassium hydroxide (4.7 mmol) in ethanol (5 ml) was stirred and refluxed for 24 hours, then cooled, poured out into ice water and acidified with HCl 6N. The mixture was partly evaporated and cooled. The precipitate was filtered, washed with water and dried, yielding 0.47 g (100%) of 2-[4-(2-naphthalenylsulfonyl)-1-piperazinyl]-5-pyrimidinecarboxylic acid (interm. 9), melting point>260° C.

c) TEA (0.0011 mol), EDC (0.0011 mol), 1-hydroxybenzotriazole (1.1 mmol) and O-(tetrahydro-2H-pyran-2-yl)-hydroxylamine (0.0011 mol) were added at room temperature to a solution of interm. 9 (8 mol) in DCM/THF (50/50) (20 ml) under N$_2$ flow. The mixture was stirred for 24 hours, then poured out into ice water and extracted with EtOAc. The organic layer was separated, dried (MgSO$_4$), filtered and the solvent was evaporated. The residue (0.56 g) was purified by column chromatography over silica gel (eluent: DCM 100 to DCM/MeOH 90/10; 5 μm). The pure fractions were collected and the solvent was evaporated. The residue (0.417 g) was purified by column chromatography over silica gel (eluent: DCM/MeOH/NH$_4$OH 92/8/1; 15-40 μm). The pure fractions were collected and the solvent was evaporated, yielding 0.293 g (69%) of 2-[4-(2-naphthalenylsulfonyl)-1-piperazinyl]-N-[(tetrahydro-2H-pyran-2-yl)oxy]-5-pyrimidinecarboxamide (interm. 10), melting point 198° C.

Example A5 a) Preparation of

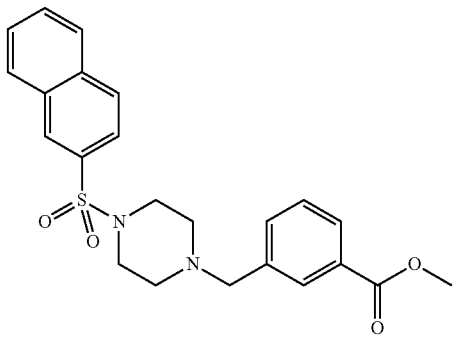

intermediate 11

A mixture of 1-(2-naphthalenylsulfonyl)-piperazine (1 equiv; 37 mmol), 3-(bromomethyl)-benzoic acid, methyl ester (0.00037 mol) and morpholinomethyl polystyrene 2% DVB (0.2 g, Novabiochem 01-64-0171, 200-400 mesh loading 3.2-3.8 mmol/g) in DMF, p.a. (5 ml) was stirred overnight (20 hours) at 100° C. The reaction mixture was filtered. The resin was washed with DMF. The solvent was evaporated at 80° C. under a gentle stream of N$_2$. The residue was purified by column chromatography (eluent: CH$_2$Cl$_2$/EtOAc 1/1). The product fractions were collected, yielding 0.044 g of interm. 11.

b) Preparation of

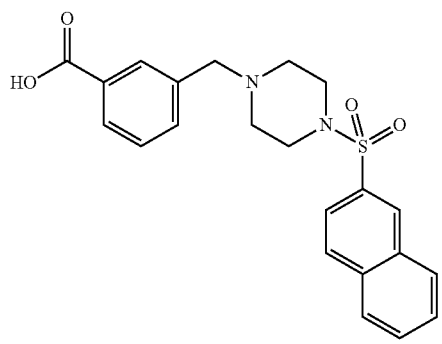

intermediate 12

A mixture of interm. 11 (1 mmol) in THF p.a. (3 ml) and NaOH 1N (1 ml) was stirred overnight at 60° C. HCl 1N (1 ml) was added. DCM (10 ml) was added and the reaction mixture was filtered through Extrelut™ NT (supplier: Merck). The filtrate (organic layer) was evaporated, yielding 0.036 g of interm. 12.

c) Preparation of

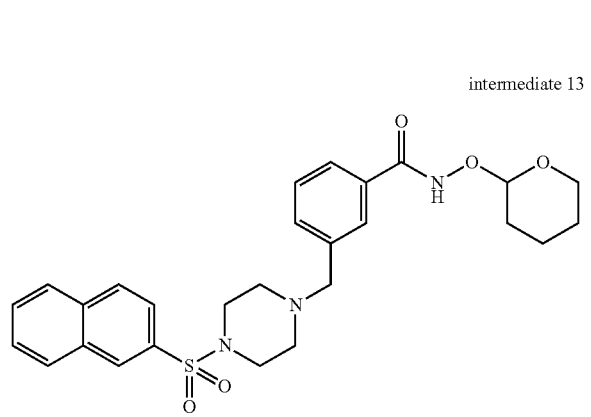 [SMILES: O=C(NOC1CCCCO1)c1cccc(CN2CCN(S(=O)(=O)c3ccc4ccccc4c3)CC2)c1]
intermediate 13

Interm. 12 (0.088 mmol) was dissolved in THF/DCM 50/50 (6 ml). EDC (1.1 equiv) was added, then TEA (1.2 equiv), then 1-hydroxy-1H-benzotriazole (1.1 equiv), then O-(tetrahydro-2H-pyran-2-yl)-hydroxylamine (1.3 equiv). The reaction mixture was stirred overnight at room temperature. Water (2 ml) was added and the reaction mixture was stirred for 15 min. DCM (10 ml) was added and the mixture was dried over Extrelut™ NT (supplier: Merck). The organic layer was separated, and the solvent was evaporated at 50° C. under a stream of $N_2$. The residue was purified by flash column chromatography on Flashtube™ 2008 (supplier Trikonex) (eluent: EtOAc). The product fractions were collected (cut off) and then eluted with DCM/MeOH 90/10). The product fractions were collected and the solvent was evaporated at 50° C. under a stream of $N_2$, yielding 0.025 g of interm. 13.

Example A6 a) Preparation of

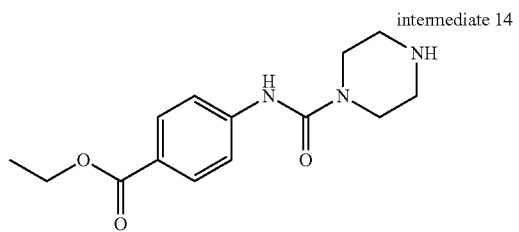 [SMILES: CCOC(=O)c1ccc(NC(=O)N2CCNCC2)cc1]
intermediate 14

A mixture of 4-[[[4-(phenylmethyl)-1-piperazinyl]carbonyl]amino]-benzoic acid, ethyl ester (9.6 mmol) in ethanol (100 ml) was hydrogenated at room temperature with Pd/C 10% (1 g) as a catalyst. After uptake of $H_2$ (1 equiv), the catalyst was filtered off over dicalite and the filtrate was evaporated, yielding 3 g of interm. 14.

b) Preparation of

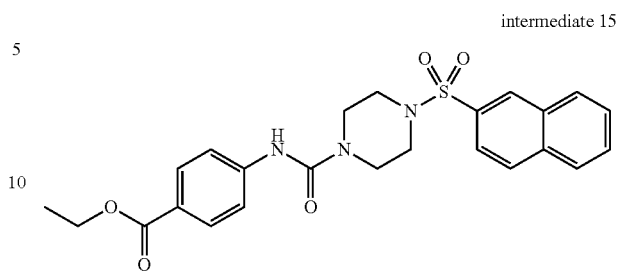
intermediate 15

A mixture of interm. 14 (9.6 mmol) and TEA (0.012 mol) in DCM (100 ml) was stirred at room temperature. 2-Naphthalenesulfonyl chloride (9.6 mmol) was added portionwise at room temperature. The reaction mixture was stirred for 30 min at room temperature, then washed with water, dried (MgSO$_4$), filtered and the solvent was evaporated. The residue was crystallized from DIPE/CH$_3$CN, filtered off and dried, yielding 3.02 g (67.4%) of interm. 15, melting point 182° C.

c) Preparation of

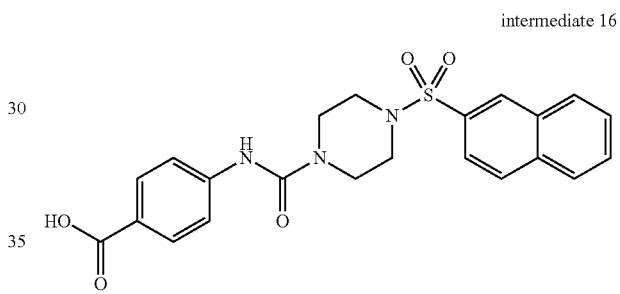
intermediate 16

A mixture of interm. 15 (2 mmol) in NaOH 1N (30 ml), THF (80 ml) and MeOH (20 ml) was stirred for 20 hours at room temperature. The mixture was neutralized with HCl 1N (30 ml). The mixture was diluted with water (100 ml), and then extracted three times with DCM. The organic layer was separated, dried (MgSO$_4$), filtered and the solvent was evaporated, yielding 0.9 g (95.7%) of interm. 16, melting point 242° C.

d) Preparation of

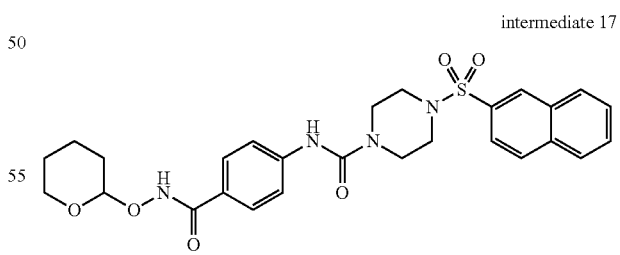
intermediate 17

A mixture of interm. 16 (0.23 mmol), O-(tetrahydro-2H-pyran-2-yl)-hydroxylamine (0.25 mmol), 1-hydroxy-1H-benzotriazole (0.00025 mol) and TEA (0.00030 mol) in DCM, p.a. (10 ml) was stirred at room temperature. EDC (0.00025 mol) was added and the reaction mixture was stirred over the weekend at room temperature. The reaction mixture was washed with water, dried (MgSO$_4$), filtered and the solvent was evaporated, yielding interm. 17.

Example A7 a) Preparation of

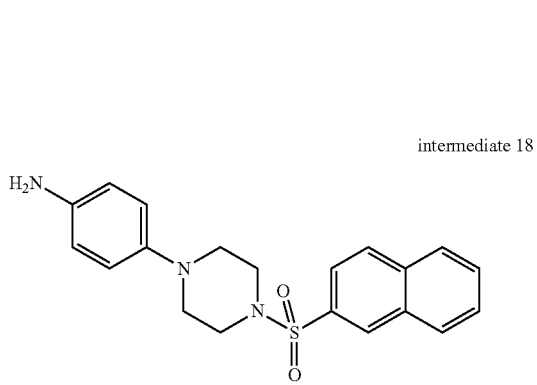 [SMILES: Nc1ccc(N2CCN(S(=O)(=O)c3ccc4ccccc4c3)CC2)cc1]

intermediate 18

A mixture of 1-(2-naphthalenylsulfonyl)-4-(4-nitrophenyl)-piperazine (7.5 m mol) in THF (150 ml) was hydrogenated at 50° C. with Pd/C 10% (1 g) as a catalyst in the presence of thiophene solution (0.5 ml). After uptake of $H_2$ (3 equiv.), the catalyst was filtered off and the filtrate was evaporated. The residue was crystallized from 2-propanol. The formed precipitate was filtered off, washed with 2-propanol and dried (55° C., vacuum), yielding 2.39 g (87%) of interm. 18.

b) Preparation of

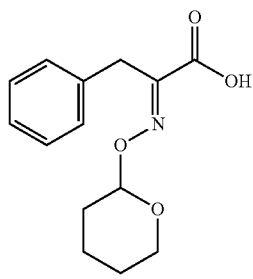

intermediate 19

O-(tetrahydro-2H-pyran-2-yl)-hydroxylamine (8.5 mmol) was added at room temperature to a mixture of α-oxo-benzenepropanoic acid (7.8 mmol) in pyridine (12 ml) and ethanol (23 ml). The mixture was stirred at room temperature for 1 hour. The solvent was evaporated till dryness. The residue (2.6 g) was purified by column chromatography over silica gel (eluent: DCM/MeOH/$NH_4OH$ 85/15/1 70/30/3; 15-40 µm). The pure fractions were collected and the solvent was evaporated, yielding 1.7 g (83%) of interm. 19.

c) Preparation of

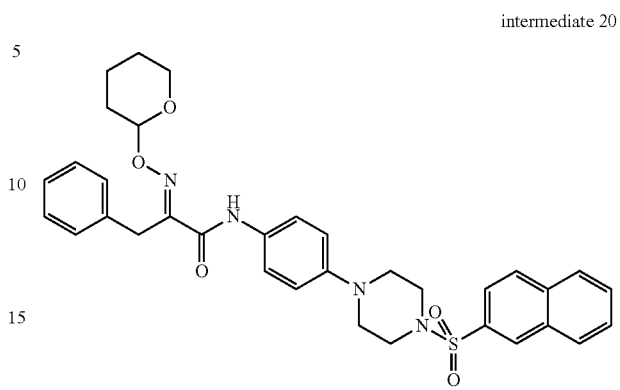

intermediate 20

EDC (1.3 mol) was added at room temperature to a mixture of interm. 18 (1.1 mmol), (interm. 19) (1.3 mmol) and 1-hydroxybenzotriazole hydrate (1.3 mmol) in DCM/THF (8 ml) under $N_2$ flow. The mixture was stirred at room temperature overnight. $K_2CO_3$ 10% was added. The mixture was extracted with DCM. The organic layer was separated, dried ($MgSO_4$), filtered, and the solvent was evaporated till dryness. The residue (0.9 g) was purified by column chromatography over silica gel (eluent: cyclohexane/EtOAc 65/35; 15-35 µm). The pure fractions were collected and the solvent was evaporated. The residue (0.35 g, 52%) was crystallized from $CH_3CN$. The precipitate was filtered off and dried, yielding 0.3 g (45%) of interm. 20, melting point 213° C.

Example A8 a) Preparation of

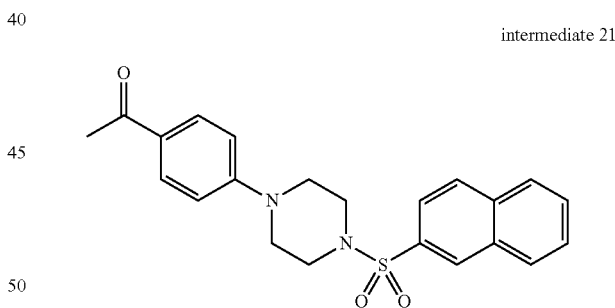

intermediate 21

A mixture of 1-(2-naphthalenesulfonyl)-piperazine (7.2 mmol), 1-(4-fluorophenyl)-ethanone (11 mmol) and $Na_2CO_3$ (11 mmol) in dimethylacetamide (5 ml) was stirred at 140° C. for 24 hours. 1-(4-fluorophenyl)-ethanone (4 mmol) was added. The mixture was stirred at 140° C. for 48 hours, then cooled, poured out into ice water and extracted with EtOAc. The organic layer was washed with water, dried ($MgSO_4$), filtered and the solvent was evaporated. The residue (3.5 g) was purified by column chromatography over silica gel (eluent: cyclohexane/EtOAc 65/35; 15-35 µm). The pure fractions were collected and the solvent was evaporated. The residue (0.95 g, 34%)was crystallized from acetonitrile. The precipitate was filtered off and dried, yielding 0.8 g of interm. 21, melting point 218° C.

b) Preparation of

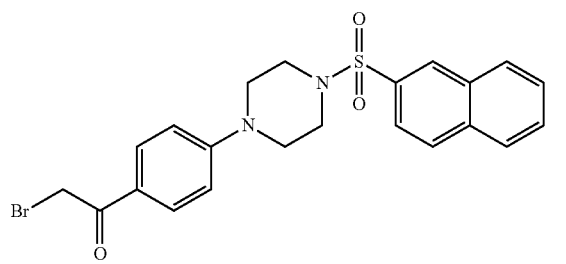
intermediate 22

A solution of interm. 21 (2.2 mmol) in trichloromethane (15 ml) was added at room temperature to a mixture of CuBr$_2$ (3.7 mmol) in EtOAc (25 ml). The mixture was stirred at 50° C. for 12 hours, then cooled to room temperature, poured out into water and extracted with EtOAc. The organic layer was separated, dried (MgSO$_4$), filtered, and the solvent was evaporated, yielding 1 g (96%) of interm. 22.

Example A9 a) Preparation of

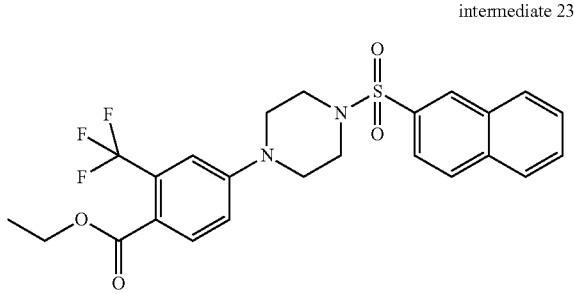 [SMILES: CCOC(=O)c1ccc(N2CCN(S(=O)(=O)c3ccc4ccccc4c3)CC2)cc1C(F)(F)F]
intermediate 23

A mixture of 1-(2-naphthalenylsulfonyl)-piperazine (3.6 mmol), 4-fluoro-2-(trifluoromethyl)-benzoic acid, ethyl ester (7.2 mmol) and Na$_2$CO$_3$ (7.2 mmol) in dimethylacetamide (10 ml) was stirred at 140° C. for 20 hours, then cooled to room temperature, poured out into ice water and extracted with EtOAc. The organic layer was washed with water, dried (MgSO$_4$), filtered and the solvent was evaporated. The residue (2.93 g) was purified by column chromatography over silica gel (eluent: cyclohexane/EtOAc 75/35; 15-40 μm). The pure fractions were collected and the solvent was evaporated. The residue (1.8 g) was crystallized from diethyl ether. The precipitate was filtered off and dried, yielding 1.265 g of interm. 23 (71%), melting point 122° C.

b) Preparation of

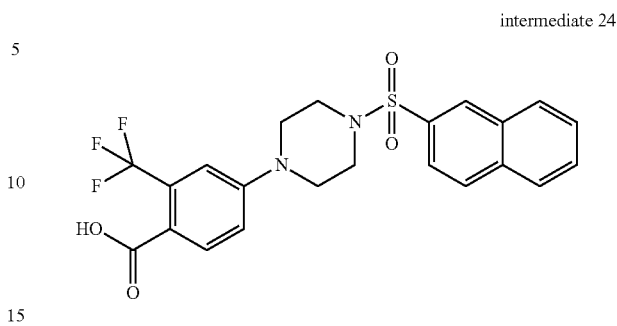
intermediate 24

A mixture of interm. 23 (3.4 mmol) and KOH (0.017 mol) in ethanol (15 ml) was stirred and refluxed for 24 hours, poured out into ice water and acidified with HC13N. The precipitate was filtered, washed with water/diethyl ether and dried, yielding 1.255 g (80%) of interm. 24, melting point 194° C.

c) Preparation of

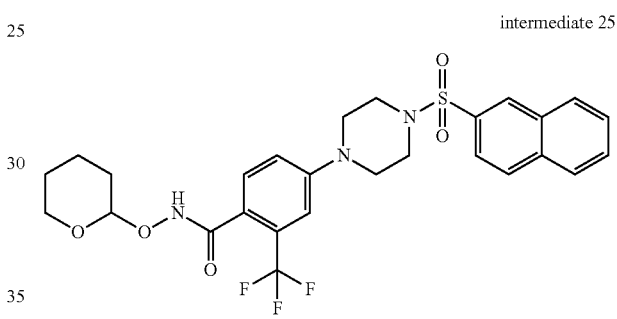
intermediate 25

TEA (1.4 mmol), EDC (1.4 mmol), 1-hydroxybenzotriazole hydrate (1.4 mmol) then O-(tetrahydro-2H-pyran-2-yl)-hydroxylamine (1.4 mmol) were added at 12° C. to a solution of (interm. 24) (1 mmol) in DCM/THF 50/50 (20 ml) under N$_2$ flow. The mixture was stirred at room temperature for 24 hours, poured out into ice water and extracted with DCM. The organic layer was separated, dried (MgSO$_4$), filtered and the solvent was evaporated. The residue was crystallized from DCM/diethyl ether. The precipitate was filtered off and dried, yielding 0.48 g (79%) of interm. 25, melting point 192° C.

Example A10 a) Preparation of

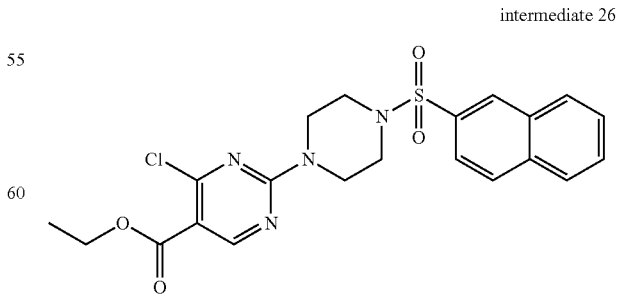
intermediate 26

NaH 60% (15 mmol) was added portionwise at room temperature to a mixture of 1-(2-naphthalenylsulfonyl)-piperazine (7.5 mmol) in THF (35 ml). The mixture was stirred at room temperature for 1 hour and 30 minutes under N₂ flow. A solution of 4-chloro-2-(methylsulfonyl)-5-pyrimidinecarboxylic acid, ethyl ester (9.8 mmol) in THF (35 ml) was added dropwise. The mixture was stirred at room temperature for 3 hours and 30 minutes, poured out into ice water and extracted with EtOAc. The organic layer was separated, dried (MgSO₄), filtered and the solvent was evaporated. The residue (4.6 g) was purified by column chromatography over silica gel (eluent: cyclohexane/EtOAc 80/20 to 20/80; 15-40 μm). Three fractions were collected and the solvent was evaporated. One of these fractions is used in the next step, yielding 0.48 g (14%) of interm. 26, melting point 123° C.

b) Preparation of intermediate 27

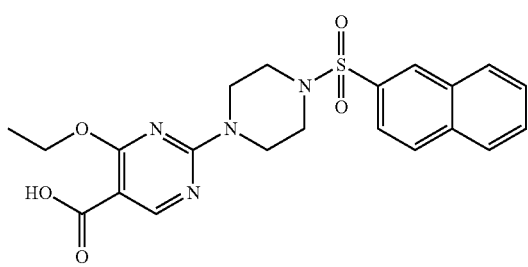

A mixture of interm. 26 (0.8 mmol) and KOH (4.2 mmol) in ethanol (10 ml) was stirred and refluxed for 24 hours, then cooled to room temperature, poured out into ice water and acidified with HCl 6N. The precipitate was filtered, washed with water/diethyl ether and dried, yielding 0.33 g (93%) of interm. 27, melting point 244° C.

c) Preparation of intermediate 28

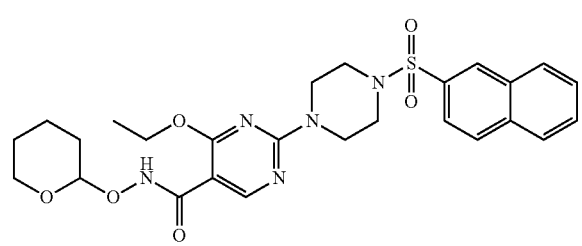

TEA (0.8 mmol), 1-hydroxybenzotriazole hydrate (0.8 mmol), EDC (0.8 mmol) then O-(tetrahydro-2H-pyran-2-yl)-hydroxylamine (0.8 mmol) were added at room temperature to a solution of (interm. 27) (0.6 mmol) in DCM/THF (10 ml) under N₂ flow. The mixture was stirred at room temperature for 24 hours, poured out into ice water and extracted with DCM. The organic layer was separated, dried (MgSO₄), filtered and the solvent was evaporated. The residue (0.47 g) was purified by column chromatography over silica gel (eluent: DCM/MeOH/NH₄OH 98/2/0.1; 15-40 μm). The pure fractions were collected and the solvent was evaporated, yielding 0.18 g (53%) of interm. 28, melting point 80° C.

Example A11 a) Preparation of intermediate 29

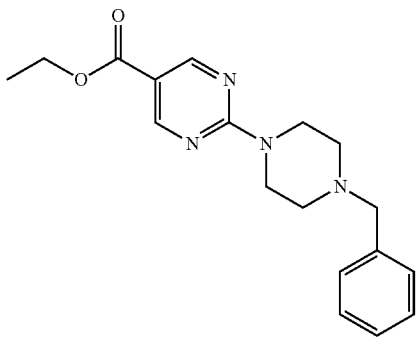

1-(Phenylmethyl)-piperazine (0.125 mol) was dissolved in acetonitrile (200 ml). K₂CO₃ (0.34 mol) was added. A solution of 2-(methylsulfonyl)-5-pyrimidinecarboxylic acid, ethyl ester (0.161 mol) in acetonitrile (200 ml) was added dropwise. The mixture was stirred at room temperature for 2 hours, then diluted with DCM (1000 ml) and washed with water. The organic layer was separated, dried (MgSO₄), filtered and the solvent was evaporated. The residue was purified by column chromatography over silicagel (DCM/MeOH 98/2). The pure fractions were collected and the solvent was evaporated. The residue was dried under vacuum at 50° C., yielding 33.6 g (82.5%) of interm. 29.

b) Preparation of intermediate 30

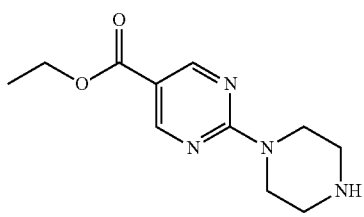

A mixture of interm. 29 (0.03 mol) in ethanol (250 ml) was hydrogenated at 50° C. with Pd/C 10% (2 g) as a catalyst. After uptake of H₂ (1 equiv), the catalyst was filtered off over dicalite and the filtrate was evaporated on Rotovap. The residue was purified by column chromatography over silica gel (eluent: DCM/(MeOH/NH₃) 90/10). The product fractions were collected and the solvent was evaporated, yielding 6.8 g (>96%) of interm. 30.

c) Preparation of intermediate 31

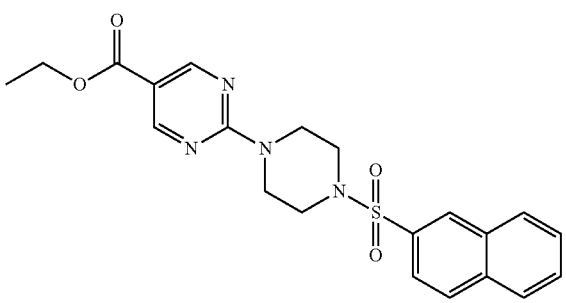

TEA (0.038 mol) was added to a solution of interm. 30 (0.029 mol) in DCM (150 ml). 2-Naphthalenesulfonyl chloride (0.032 mol) was added and the reaction mixture was stirred overnight at room temperature. Then the mixture was washed with water. The organic layer was separated, washed with water, dried (MgSO$_4$), filtered and the solvent was evaporated. The residue was crystallized from CH$_3$CN, filtered off and dried in vacuo, yielding 7.4 g (>60%) of interm. 31, melting point>260° C.

d) Preparation of intermediate 32

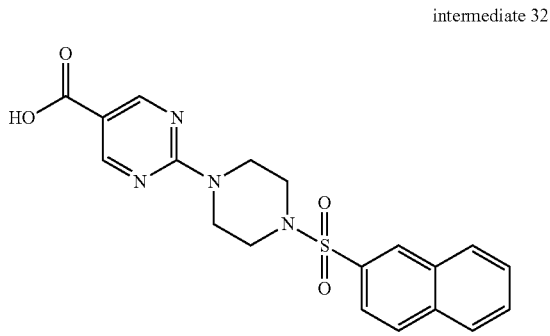 [SMILES: O=C(O)c1cnc(N2CCN(S(=O)(=O)c3ccc4ccccc4c3)CC2)nc1]

A mixture of interm. 31 (0.017 mol) in THF (250 ml), NaOH 1N (250 ml) and MeOH (50 ml) was stirred for 5 hours at room temperature. HCl 1N (250 ml) was added and the mixture was stirred for 45 min at room temperature. The precipitate was filtered off and dried (vacuum, 60° C., overnight), yielding 6.0 g (89%) of interm. 32, melting point>260° C.

e) Preparation of intermediate 33

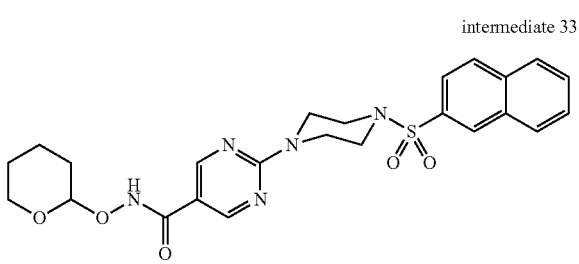 [SMILES: O=C(NOC1CCCCO1)c1cnc(N2CCN(S(=O)(=O)c3ccc4ccccc4c3)CC2)nc1]

Interm. 32 (0.015 mol) was stirred in DCM/THF 50/50 (650 ml). EDC (0.018 mol) was added. TEA (0.020 mol) was added. 1-Hydroxy-1H-benzotriazole (0.018 mol) was added, followed by O-(tetrahydro-2H-pyran-2-yl)-hydroxylamine (0.018 mol). The reaction mixture was stirred for 6 hours at room temperature, and then washed twice with water and DCM was added. The organic layer was separated, dried (MgSO$_4$), filtered and the solvent was evaporated. The residue was suspended in boiling CH$_3$CN, then stirred overnight at room temperature. The resulting precipitate was filtered off, washed with CH$_3$CN, and dried (vacuum; 50° C.), yielding 6.1 g (82%) of interm. 33, melting point 198° C.

Example A12 a) Preparation of intermediate 34

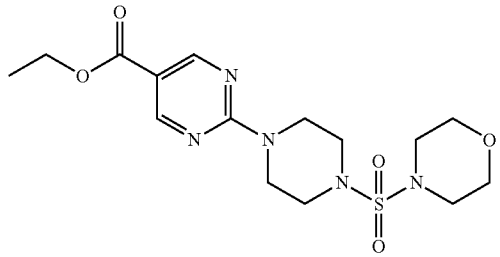

NaH (6.5 mmol) was added at room temperature to a solution of 4-(1-piperazinylsulfonyl)-morpholine (3.2 mmol) in THF (15 ml) under N$_2$ flow. The mixture was stirred for 1 hour, then cooled to 0° C. A solution of 2-(methylsulfonyl)-5-pyrimidinecarboxylic acid, ethyl ester (4.2 mmol) in THF (9 ml) was added. The mixture was stirred for 2 hours, poured out into ice water. The precipitate was filtered off and dried. The residue (0.665 g) was taken up in diethyl ether. The precipitate was filtered off and dried. The filtrate was evaporated and combined with the precipitate, yielding 0.408 g of interm. 34.

b) Preparation of intermediate 35

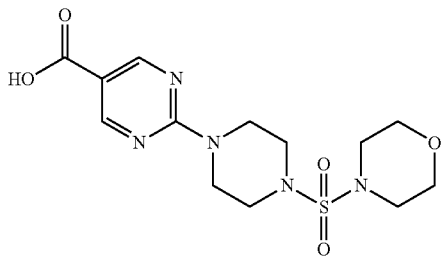

A mixture of interm. 34 (1 mmol) and LiOH H$_2$O (3.1 mmol) in THF (6 ml) and water (6 ml) was stirred and refluxed for 24 hours, then cooled. The solvent was evaporated. The mixture was acidified with HCl 3N. EtOAc was added. The mixture was filtered over celite. The organic layer was extracted with EtOAc. The organic layer was separated, dried (MgSO$_4$), filtered and the solvent was evaporated, yielding 0.139 g of interm. 35.

c) Preparation of intermediate 36

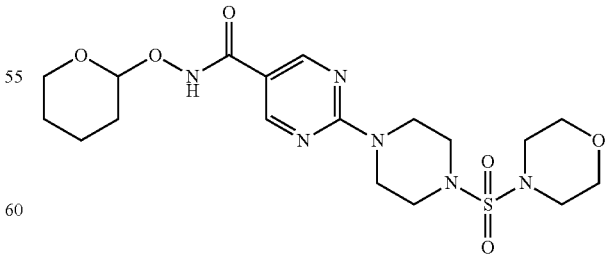

1-Hydroxybenzotriazole hydrate (0.5 mmol) and EDC (0.5 mmol) were added at 10° C. to a solution of interm. 35 (0.3 mmol) and TEA (0.5 mmol) in THF/DCM (6 ml) under N$_2$ flow. The mixture was stirred for 1 hour. O-(tetrahydro-2H-pyran-2-yl)-hydroxylamine (0.5 mmol) was added. The mixture was stirred at room temperature overnight. Ice and water were added. The mixture was extracted with DCM. The organic layer was separated, dried (MgSO₄), filtered, and the solvent was evaporated. The residue (0.259 g) was purified by column chromatography over silica gel (eluent: CH₂Cl₂/iPrOH/NH₄OH 98/2/0.2; 10 μm). The pure fractions were collected and the solvent was evaporated, yielding 0.024 g of interm 36.

Example A13 a) Preparation of

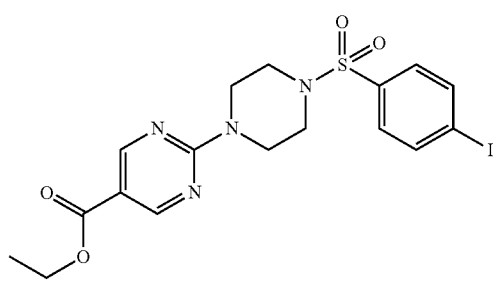

intermediate 37

Interm. 30 (114 mmol) was stirred in 800 ml DCM, TEA (180 mmol) was added, 4-iodo-benzenesulfonyl chloride (149 mmol) was added in portions. The reaction mixture was stirred overnight at room temperature. DCM (1000 ml) and water (300 ml) were added. The organic layer was extracted, separated and dried (MgSO4), filtered and the solvent was evaporated. The product (crude) was suspended in boiling acetonitrile, allowed to reach room temperature and filtered. The product was dried in vacuum at 50° C., yielding 51.4 g (89.5%) of interm. 37.

b) Preparation of

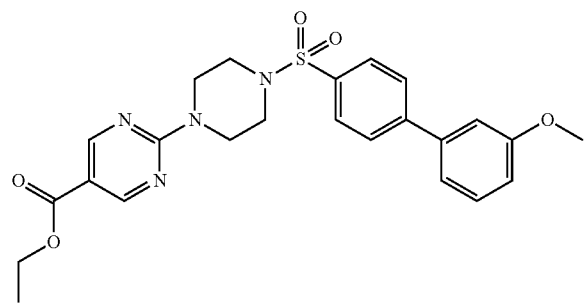

intermediate 38

A solution of interm. 37 (0.1 mmol) and cesium carbonate (0.15 mmol) in DMF (2 ml) was added to a solution of (3-methoxyphenyl)-boronic acid (0.149 mmol) in DMF (1 ml). The reaction mixture was shaked under N₂ for 2 min. Palladium(II) acetate (0.02 mmol) and 1,3-bis(diphenylphosphino)propane (0.02 mmol) were added. The reaction mixture was shaked at 80° C. for 4 h and then allowed to reach room temperature. The solvent was evaporated under vacuum at 80° C. The residue was dissolved in DCM (20 ml) and MeOH (2 ml) and then washed with 3 ml 10% Na₂CO₃ in water. The reaction mixture was dried over Extrelut™ NT (supplier: Merck) and concentrated at 50° C. with N₂-blow.

The product was purified by column chromatography over silicagel. The pure fractions were collected and the solvent was evaporated and dried at 50° C. under N₂-blow, yielding interm. 38.

c) Preparation of

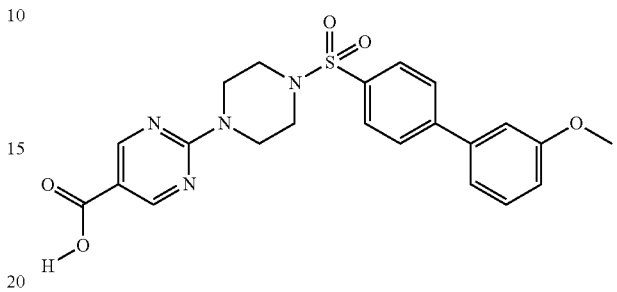

intermediate 39

Interm. 38 (0.0352 mmol) was dissolved in THF (4 ml) and MeOH (1 ml). NaOH (1.5 mmol) was added. The mixture was stirred overnight at room temperature. A mixture of HCl (1.5 ml) and 10 to 20 ml THF were added. The reaction mixture was dried Extrelut™ NT (supplier: Merck). The solvent was evaporated (60° C., N₂-blow). Toluene was added. The solvent was evaporated under vacuum at 70° C. Toluene was added again. The solvent was evaporated at 80° C. under vacuum, yielding 16 mg (100%) of interm. 39.

d) Preparation of

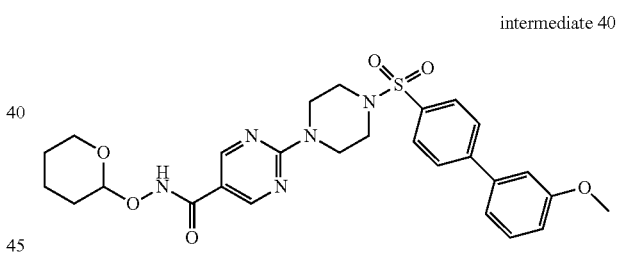

intermediate 40

A solution of 1-hydroxybenzotriazole (0.1 mmol), EDC (0.1 mmol) and TEA (0.12 mmol) in DCM (3 ml) and THF (4 ml) was added to (interm. 39) (0.1 mmol). The reaction mixture was stirred for 5 min at room temperature. O-(tetrahydro-2H-pyran-2-yl)-hydroxylamine (0.1 mmol) was added. The reaction mixture was stirred overnight at room temperature. Water (3 ml) and DCM (10 ml) were added. The reaction mixture was dried. The reaction mixture was concentrated under N₂ at 60° C. The residue was dissolved in DCM (5 ml) and shaked gently for 4 hours with 150 mg methylisocyanate-polystyrene 2% DVB 200-400 mesh loading 1.4-1.8 mmol/g (Supplier: Novabiochem 01-64-0169) to scavenge the excess of O-(tetrahydro-2H-pyran-2-yl)-hydroxylamine The mixture was filtered, the resin was washed twice with DCM (2 ml). The mixture was concentrated at 40° C. under N₂ and then purified by column chromatography (eluent 50% EtOAc/DCM). The pure fractions were collected and the solvent was evaporated, yielding interm. 40.

Example A14

Preparation of

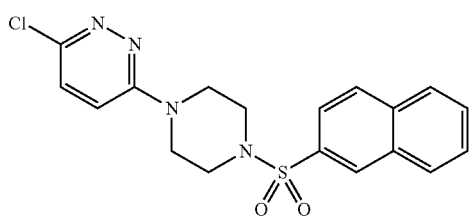

intermediate 41

A mixture of 3,6-dichloro-pyridazine (0.0034 mol) and 1-(2-naphthalenylsulfonyl)-piperazine (0.0034 mol) in DMF (2 ml) was stirred at 110° C. for 4 hours, then cooled to room temperature and poured out into EtOAc/H$_2$O. The mixture was filtered off. The filtrate was extracted. The organic layer was washed with water, dried (MgSO$_4$), filtered and the solvent was evaporated. The residue (0.85 g) was purified by column chromatography over silica gel (20-45 μm) (eluent: cyclohexane/EtOAc 90/10). The pure fractions were collected and the solvent was evaporated (0.56 g, 42%). This fraction was crystallized from diethyl ether. The precipitate was filtered off and dried, yielding 0.178 g (14%) of intermediate 41, melting point 213° C.

Example A15 a) Preparation of

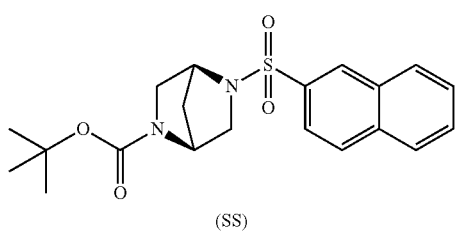

intermediate 42

(SS)

A solution of 2-naphtalenesulfonyl chloride (0.0066 mol) in DCM (15 ml) was added dropwise at 0° C. to a mixture of 2,5-diazabicyclo[2.2.1]heptane-2-carboxylic acid, 1,1-dimethylethyl ester, (1S,4S) (0.0051 mol) and TEA (0.0098 mol) in DCM (15 ml). The mixture was stirred at room temperature for 12 hours, poured out into ice water and extracted with DCM. The organic layer was washed with potassium carbonate 10%, dried (MgSO$_4$), filtered and the solvent was evaporated. The residue was crystallized from diethyl ether. The precipitate was filtered off and dried, yielding 2.05 g (85%) of intermediate 42 (S,S), melting point 129° C.

b) Preparation of

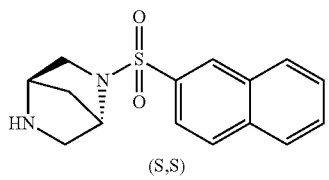

intermediate 43

(S,S)

A mixture of intermediate 42 (S,S) (0.0049 mol) in HCl 6N (20 ml) and THF (5 ml) was stirred at 80° C. for 12 hours, then cooled to room temperature, poured out into ice water, basified with NH$_4$OH and extracted with DCM. The organic layer was separated, dried (MgSO$_4$), filtered, and the solvent was evaporated. The residue (1.4 g) was crystallized from diethyl ether. The precipitate was filtered off and dried, yielding 0.5 g (36%) of intermediate 43 (S,S), melting point 159° C.

c) Preparation of

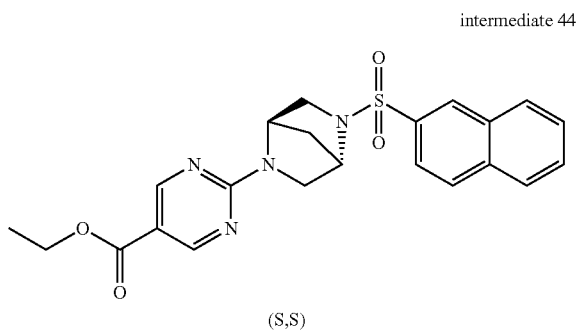 [SMILES: CCOC(=O)c1cnc(N2C[C@@H]3C[C@@H]2CN3S(=O)(=O)c2ccc3ccccc3c2)nc1 ; "(S,S)"]

intermediate 44

(S,S)

Sodium hydride 60% (0.0051 mol) was added at 0° C. to a mixture of intermediate 43 (S,S) (0.0034 mol) in THF (20 ml) under N$_2$ flow. The mixture was stirred for 1 hour. A solution of 2-(methylsulfonyl)-5-pyrimidinecarboxylic acid, ethyl ester (0.0045 mol) in THF (10 ml) was added dropwise at 0° C. The mixture was stirred at room temperature for 2 hours and poured out into ice water. EtOAc was added. The mixture was filtered, washed with diethyl ether and dried, yielding 0.4 g of intermediate 44 (S,S), melting point 212° C. The filtrate was extracted. The organic layer was washed with water, dried (MgSO$_4$), filtered and the solvent was evaporated. The residue (1.7 g) was purified by column chromatography over silica gel (15-35 μm) (eluent: cyclohexane/EtOAc 60/40). The pure fractions were collected and the solvent was evaporated yielding 1 g (66%) of intermediate 44 (S,S)

d) Preparation of

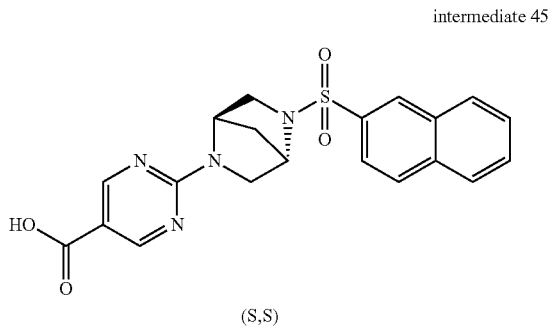

intermediate 45

(S,S)

sodium salt

A mixture of intermediate 44 (S,S) (0.0021 mol) and sodium hydroxide (0.0042 mol) in EtOH (40 ml) was stirred and refluxed for 12 hours, then cooled. The precipitate was filtered, washed with diethyl ether and dried, yielding 0.56 g (62%) of intermediate 45 Na (S,S).

e) Preparation of intermediate 46

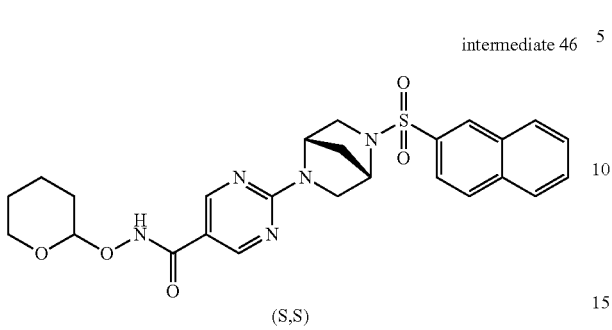

(S,S)

EDC (0.0017 mol) and DCM (20 ml) were added at room temperature to a mixture of intermediate 45 (0.0013 mol), O-(tetrahydro-2H-pyran-2-yl)-hydroxylamine (0.0017 mol) and 1-hydroxybenzotriazole (0.0017 mol) in THF (20 ml). The mixture was stirred at room temperature for 12 hours, poured out into water and extracted with DCM. The organic layer was separated, dried ($MgSO_4$), filtered, and the solvent was evaporated. The residue (0.8 g) was purified by column chromatography over silica gel (15-40 μm) (eluent: DCM/MeOH 90.5/0.5). The pure fractions were collected and the solvent was evaporated. The residue (0.43 g, 66%) was crystallized from diethyl ether/DIPE. The precipitate was filtered off and dried, yielding 0.36 g of intermediate 46 (S,S), melting point 176° C.

Example A16 a) Preparation of intermediate 47

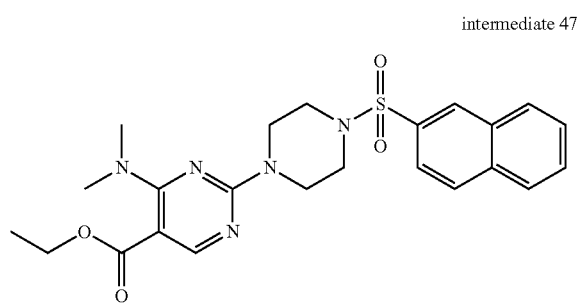 [SMILES: CCOC(=O)c1cnc(N2CCN(S(=O)(=O)c3ccc4ccccc4c3)CC2)nc1N(C)C]

A mixture of intermediate 26 (0.001 mol), N-methylmethanamine, hydrochloride (0.0015 mol) and potassium carbonate (0.003 mol) in acetonitrile (10 ml) was stirred at 80° C. for 24 hours, then cooled, poured out into ice water and extracted with DCM. The organic layer was separated, dried ($MgSO_4$), filtered, and the solvent was evaporated. The residue (0.45 g) was crystallized from DIPE. The precipitate was filtered off and dried, yielding 0.254 g (53%) of intermediate 47, melting point 117° C.

b) Preparation of intermediate 48

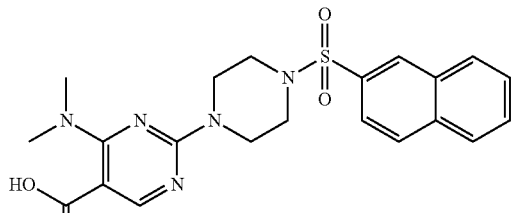

A mixture of intermediate 47 (0.0008 mol) and sodium hydroxide (0.0019 mol) in EtOH (10 ml) was stirred and refluxed for 24 hours, then cooled to room temperature, poured out into ice water, acidified with HCl 3N and extracted with EtOAc. The organic layer was separated, dried ($MgSO_4$), filtered, and the solvent was evaporated, yielding 0.25 g (67%) of intermediate 48. This product was used directly in the next reaction step.

c) Preparation of intermediate 49

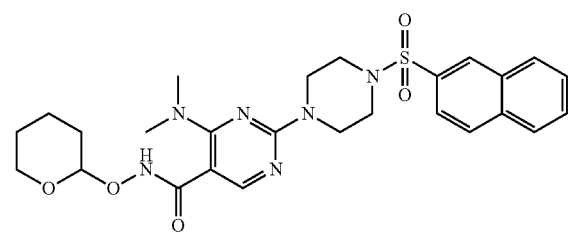

1-hydroxybenzotriazole (0.0007 mol) and EDC (0.0007 mol) were added at room temperature to a solution of intermediate 48 (0.0005 mol) and TEA (0.0007 mol) in THF/DCM (6 ml). The mixture was stirred for 30 minutes. O-(tetrahydro-2H-pyran-2-yl)-hydroxylamine (0.0007 mol) was added. The mixture was stirred at room temperature for 24 hours, poured out into ice water. The mixture was extracted with EtOAc. The organic layer was separated, dried ($MgSO_4$), filtered, and the solvent was evaporated. The residue (0.48 g) was purified by column chromatography over silica gel (10 μm) (eluent: DCM/MeOH 98/2). The pure fractions were collected and the solvent was evaporated. The residue (0.127 g) was crystallized from diethyl ether. The precipitate was filtered off and dried, yielding 0.12 g (40%) of intermediate 49, melting point 118° C.

Example A17 a) Preparation of intermediate 50

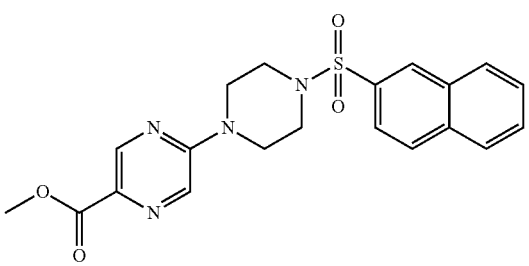

Sodium hydride (0.0181 mol) was added at room temperature to a solution of 1-(2-naphthalenylsulfonyl)-piperazine (0.009 mol) in THF (15 ml) under N₂ flow. The mixture was stirred for 1 hour, then cooled to 0° C. A solution of 5-chloropyrazinecarboxylic acid, methyl ester (0.0136 mol) in THF (5 ml) was added. The mixture was stirred at 90° C. overnight, then cooled and poured out into ice water. The precipitate was filtered, washed with water, then with diethyl ether and dried, yielding 3.3 g (89%) of intermediate 50, melting point 216° C.

b) Preparation of intermediate 51

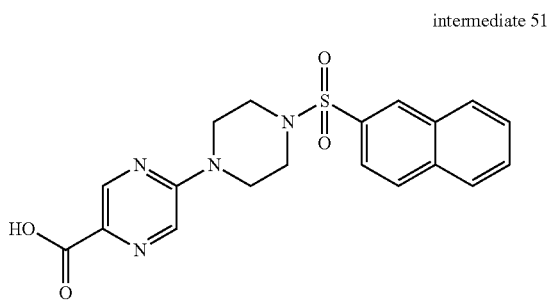 [SMILES: O=C(O)c1cnc(N2CCN(S(=O)(=O)c3ccc4ccccc4c3)CC2)cn1]

A mixture of intermediate 50 (0.0079 mol) and potassium hydroxide (0.039 mol) in MeOH (50 ml) was stirred and refluxed overnight, then cooled, poured out into ice water and acidified with HCl 3N. The precipitate was filtered, washed with water and dried, yielding 2.88 g (92%) of intermediate 51, melting point 273° C.

c) Preparation of intermediate 52

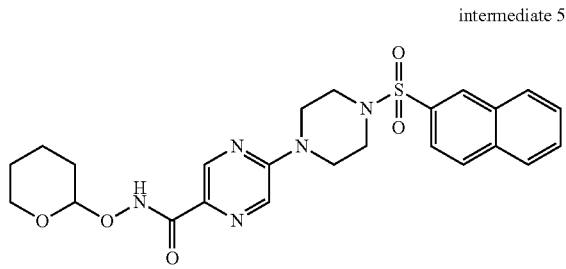

EDC (0.0092 mol) and 1-hydroxybenzotriazole (0.0092 mol) were added at room temperature to a solution of intermediate 51 (0.007 mol) and TEA (0.0092 mol) in THF/DCM (96 ml) under N₂ flow. The mixture was stirred for 1 hour. O-(tetrahydro-2H-pyran-2-yl)-hydroxylamine (0.0092 mol) was added. The mixture was stirred at room temperature for 2 days, poured out into ice water and extracted with DCM. The organic layer was separated, dried (MgSO₄), filtered, and the solvent was evaporated. The residue (4.2 g) was purified by column chromatography over silica gel (15-40 μm) (eluent: DCM/MeOH/NH₄OH 98/2/0.1). Two fractions were collected and the solvent was evaporated, yielding 2 g F1 and 1.2 g F2. F1 was crystallized from diethyl ether. The precipitate was filtered off and dried, yielding 1.84 g of intermediate 52, melting point 201° C. F2 was crystallized from diethyl ether/DCM/MeOH. The precipitate was filtered off and dried, yielding 1.2 g (24%) of intermediate 52. Total yielding 2.576 g (77%) of intermediate 52.

Example A18 a) Preparation of intermediate 53

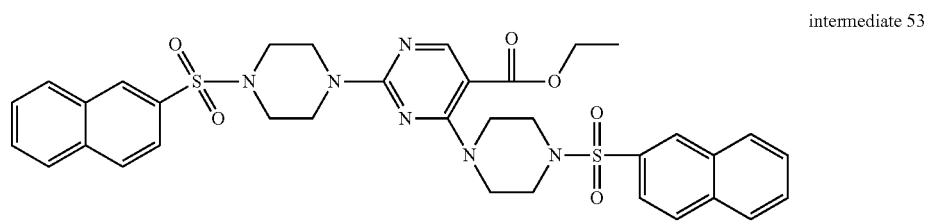 [SMILES: CCOC(=O)c1cnc(N2CCN(S(=O)(=O)c3ccc4ccccc4c3)CC2)nc1N1CCN(S(=O)(=O)c2ccc3ccccc3c2)CC1]

Sodium hydride 60% (0.0052 mol) was added at room temperature to a solution of 1-(2-naphthalenylsulfonyl)-piperazine (0.0026 mol) in THF (10 ml) under N₂ flow. The mixture was stirred at room temperature for 1 hour, then cooled to 0° C. A solution of 4-chloro-2-(methylsulfonyl)-5-pyrimidinecarboxylic acid, ethyl ester (0.0008 mol) in THF (5 ml) was added quickly. The mixture was stirred at 0° C. for 3 hours, poured out into ice water and extracted with EtOAc. The organic layer was separated, dried (MgSO₄), filtered, and the solvent was evaporated. The residue (0.86 g) was purified by column chromatography over silicagel (10 μm) (eluent: cyclohexane/EtOAc 80/20). The pure fractions were collected and the solvent was evaporated. The residue (0.29 g) was taken up in diethyl ether. The precipitate was filtered off and dried, yielding 0.264 g (43%) of intermediate 53, melting point 124° C.

b) Preparation of

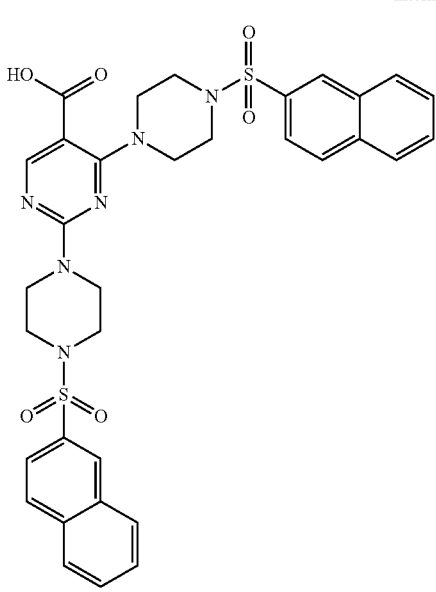

intermediate 54

A mixture of intermediate 53 (0.0003 mol) and potassium hydroxide (0.0012 mol) in EtOH (8 ml) was stirred and refluxed for 24 hours, then cooled. The solvent was evaporated. The residue was taken up in ice water, acidified with HCl 3N and extracted with EtOAc. The organic layer was separated, dried (MgSO$_4$), filtered, and the solvent was evaporated, yielding (0.14 g) of intermediate 54. This fraction was used directly in the next reaction step.

c) Preparation of

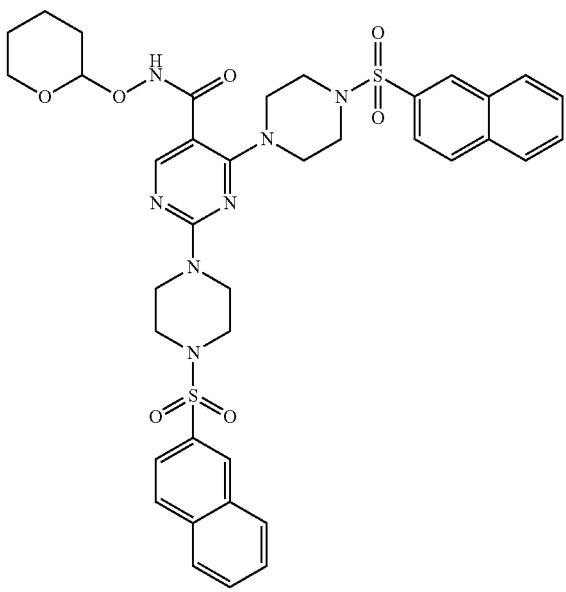

intermediate 55

1-hydroxybenzotriazole (0.0002 mol) and EDC (0.0002 mol) were added at room temperature to a solution of intermediate 54 (0.0002 mol) and TEA (0.0002 mol) in THF/DCM (6 ml) under N$_2$ flow. The mixture was stirred at room temperature for 1 hour. O-(tetrahydro-2H-pyran-2-yl)-hydroxylamine (0.0002 mol) was added. The mixture was stirred at room temperature overnight, poured out into ice water and extracted with DCM. The organic layer was separated, dried (MgSO$_4$), filtered, and the solvent was evaporated. The residue (0.16 g) was purified by column chromatography over silicagel (10 μm) (eluent: DCM 100 then DCM/MeOH 99/1). The pure fractions were collected and the solvent was evaporated, yielding 0.023 g of intermediate 55.

Example A19 a) Preparation of

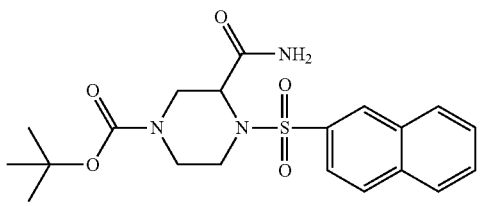

intermediate 56

A solution of 2-naphtalenesulfonyl chloride (0.0022 mol) in DCM (5 ml) was added dropwise at 0° C. to a mixture of 3-(aminocarbonyl)-1-piperazinecarboxylic acid, 1,1-dimethylethyl ester (0.0022 mol) and TEA (0.0044 mol) in DCM (5 ml). The mixture was stirred at room temperature for 20 hours, poured out into ice water and extracted with DCM. The organic layer was separated, dried (MgSO$_4$), filtered and the solvent was evaporated. The residue (0.9 g) was crystallized from DCM/methyl alcohol/diethyl ether. The precipitate was filtered off and dried, yielding 0.7 g (76%) of intermediate 56, melting point 200° C.

b) Preparation of

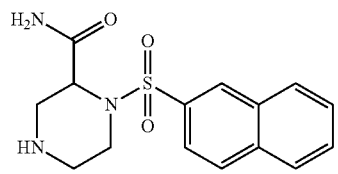

intermediate 57

Trifluoroacetic acid (2 ml) was added to a solution of intermediate 56 (0.0015 mol) in DCM (20 ml) and stirred at room temperature for 7 h. The mixture was poured out into ice water, basified by NH$_4$OH and extracted with DCM. The organic layer was separated, dried (MgSO$_4$), filtered, and the solvent was evaporated yielding 0.44 g (90%) of intermediate 57, melting point 148° C.

c) Preparation of

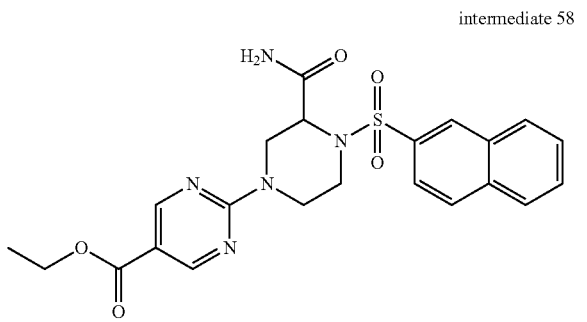 [SMILES: CCOC(=O)c1cnc(N2CCN(S(=O)(=O)c3ccc4ccccc4c3)C(C(N)=O)C2)nc1]

intermediate 58

A solution of 2-(methylsulfonyl)-5-pyrimidinecarboxylic acid, ethyl ester (0.0164 mol) in acetonitrile (30 ml) was added at 10° C. to a solution of intermediate 57 (0.0164 mol) and potassium carbonate (0.019 mol) in acetonitrile (30 ml). The mixture was stirred at room temperature for 4 hours, poured out into ice water and extracted with EtOAc. The organic layer was separated, dried ($MgSO_4$), filtered, and the solvent was evaporated. The residue (8.4 g) was purified by column chromatography over silica gel (15-40 μm) (eluent: DCM/MeOH/$NH_4OH$ 97/3/0.1). Two fractions were collected and the solvent was evaporated, yielding 1.49 g F1 and 2.41 g F2. F1 was crystallized from diethyl ether. The precipitate was filtered off and dried, yielding 1.42 g (19%) of intermediate 58, melting point 171° C. F2 was crystallized from diethyl ether/MeOH. The precipitate was filtered off and dried, yielding 1.405 g (18%) of intermediate 58. Total yielding 2.8 g (37%) of intermediate 58.

d) Preparation of intermediate 59

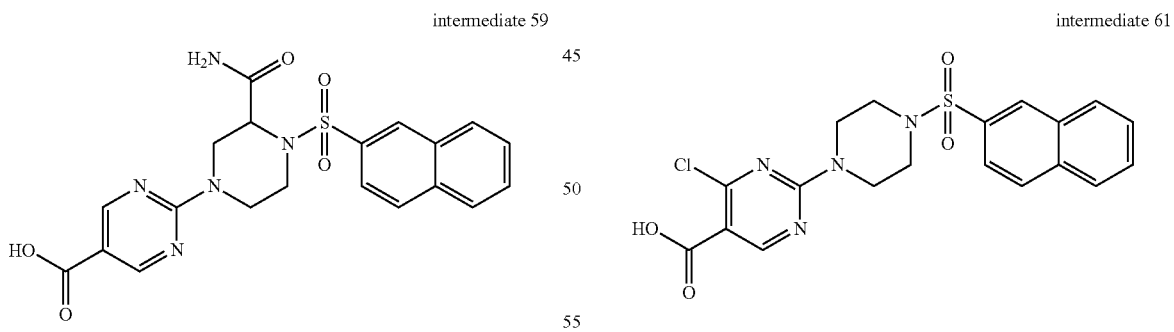

A mixture of intermediate 58 (0.0059 mol) and lithium hydroxide, monohydrate (0.0095 mol) in THF (50 ml) and water (50 ml) was stirred at room temperature for 5 hours, poured out into ice water and acidified with HC13N. The precipitate was filtered, washed with water and dried with diethyl ether under a vacuo, yielding 1.96 g (76%) of intermediate 59, melting point 277° C. This fraction was used directly in the next reaction step.

e) Preparation of

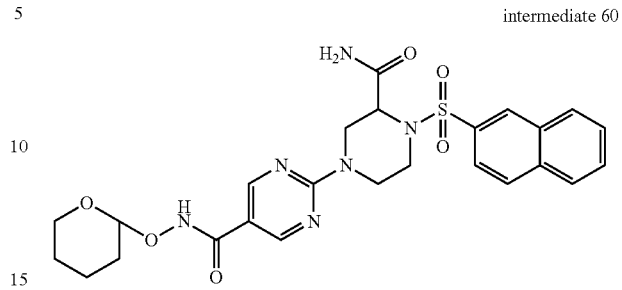

intermediate 60

EDC (0.0058 mol) and 1-hydroxybenzotriazole (0.0058 mol) were added at 10° C. to a solution of intermediate 59 (0.0044 mol) and TEA (0.0058 mol) in THF/DCM (40 ml) under $N_2$ flow. The mixture was stirred for 1 hour. O-(tetrahydro-2H-pyran-2-yl)-hydroxylamine (0.0058 mol) was added. The mixture was stirred from 10° C. to room temperature overnight, poured out into ice water and extracted with DCM. The organic layer was separated, dried ($MgSO_4$), filtered, and the solvent was evaporated. The residue (2.95 g) was purified by column chromatography over silica gel (15-40 μm) (eluent: DCM/MeOH/$NH_4OH$ 97/3/0.1). The pure fractions were collected and the solvent was evaporated. The residue (1.6 g) was crystallized from diethyl ether. The precipitate was filtered off and dried, yielding 1.355 g (57%) of intermediate 60, melting point 160° C.

Example A20 a) Preparation of intermediate 61

A mixture of intermediate 26 (0.0043 mol) and lithium hydroxide, monohydrate (0.013 mol) in THF (60 ml) and water (60 ml) was stirred at room temperature for 24 hours, poured out into ice water, acidified with HC13N and extracted with EtOAc. The organic layer was separated, dried ($MgSO_4$), filtered, and the solvent was evaporated. The residue (2.37 g) was crystallized from diethyl ether. The precipitate was filtered off and dried, yielding 1.76 g (94%) of intermediate 61.

b) Preparation of intermediate 62

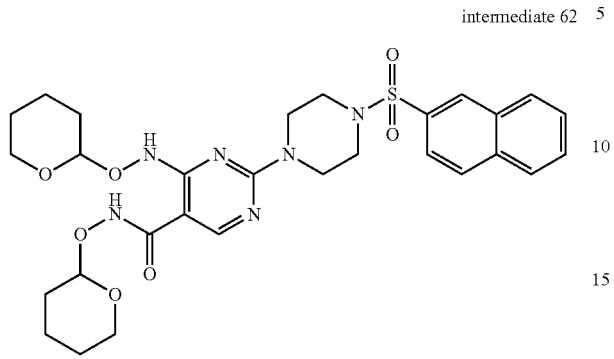

EDC (0.0007 mol) and 1-hydroxybenzotriazole (0.0007 mol) were added at room temperature to a solution of intermediate 61 (0.0005 mol) and TEA (0.0007 mol) in THF/DCM (6 ml). The mixture was stirred for 30 minutes. O-(tetrahydro-2H-pyran-2-yl)-hydroxylamine (0.0007 mol) was added. The mixture was stirred at room temperature for 24 hours. O-(tetrahydro-2H-pyran-2-yl)-hydroxylamine (0.0007 mol) was added again. The mixture was stirred overnight, poured out into ice water and extracted with DCM. The organic layer was separated, dried (MgSO$_4$), filtered, and the solvent was evaporated. The residue (0.47 g) was purified by column chromatography over silica (10 μm) (eluent: DCM 100 then DCM/MeOH 99/1). The pure fractions were collected and the solvent was evaporated. The residue (0.25 g, 82%) was crystallized from diethyl ether. The precipitate was filtered off and dried, yielding 0.215 g (70%) of intermediate 62, melting point 122° C.

Example A21 a) Preparation of intermediate 63

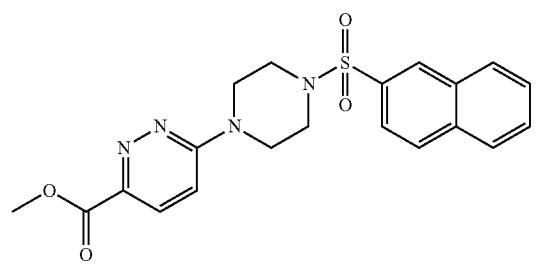

A mixture of intermediate 41 (0.0013 mol), Pd(OAc)$_2$ (0.0006 mol), 1,3-propanediylbis[diphenyl-phosphine] (0.0006 mol) and acetic acid, potassium salt (0.0026 mol) in MeOH (35 ml) was stirred at 100° C. for 5 hours under a 5 bar pressure of CO and poured out into ice water. DCM was added. The mixture was filtered over celite. The organic layer was separated, dried (MgSO$_4$), filtered, and the solvent was evaporated. The residue (2.06 g) was purified by column chromatography over silica gel (15-40 μm) (eluent: DCM/MeOH/NH$_4$OH 97/3/0.1). The pure fractions were collected and the solvent was evaporated, yielding 0.40 g (74%) of intermediate 63.

b) Preparation of intermediate 64

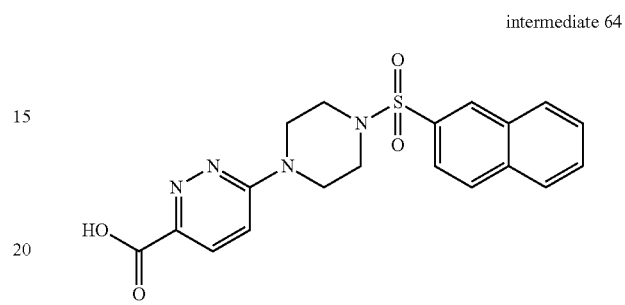

A mixture of intermediate 63 (0.0014 mol) and potassium hydroxide (0.0059 mol) in MeOH (15 ml) was stirred at 60° C. for 5 hours, then cooled to room temperature, poured out into ice water and acidified with HCl 3N. The precipitate was filtered, washed with water/diethyl ether and dried, yielding 0.47 g (80%) of intermediate 64, melting point 238° C. This product was used directly in the next reaction step.

c) Preparation of intermediate 65

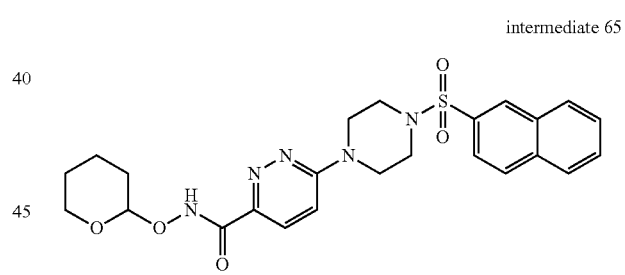

A solution of EDC (0.0015 mol) and 1-hydroxybenzotriazole (0.0015 mol) was added at room temperature to a solution of intermediate 64 (0.0012 mol) and TEA (0.0015 mol) in THF/DCM (50/50) (16 ml) under N$_2$ flow. The mixture was stirred for 30 minutes. O-(tetrahydro-2H-pyran-2-yl)-hydroxylamine (0.0015 mol) was added. The mixture was stirred at room temperature for 24 hours, poured out into ice water and extracted with DCM. The organic layer was separated, dried (MgSO$_4$), filtered, and the solvent was evaporated. The residue (1 g) was purified by column chromatography over silica gel (15-40 μm) (eluent: DCM/MeOH/NH$_4$OH 98/2/0.1). The pure fractions were collected and the solvent was evaporated. The residue (0.36 g) was crystallized from diethyl ether. The precipitate was filtered off and dried, yielding 0.275 g (46%) of intermediate 65, melting point 211° C.

Example A22 a) Preparation of intermediate 66

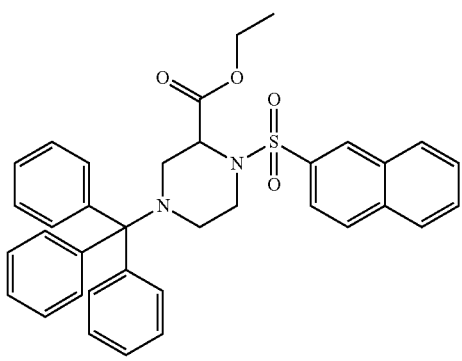

A solution of 2-naphthalenesulfonyl chloride (0.028 mol) in DCM (40 ml) was added dropwise at 0° C. to a mixture of 4-(triphenylmethyl)-2-piperazinecarboxylic acid, ethyl ester (0.025 mol) and TEA (0.038 mol) in DCM (70 ml) under $N_2$ flow. The mixture was stirred at room temperature for 12 hours, poured out into ice water and extracted with DCM. The organic layer was washed with water, dried ($MgSO_4$), filtered and the solvent was evaporated. The residue (15 g) was crystallized from acetonitrile. The precipitate was filtered off and dried, yielding 6 g of intermediate 66, melting point 145° C. The mother layer was evaporated and was crystallized from CH3CN/diethyl ether. The precipitate was filtered off and dried. Yielding: 2.2 g of intermediate 66. The mother layer was evaporated. Yielding: 4.5 g of intermediate 66.

b) Preparation of intermediate 67

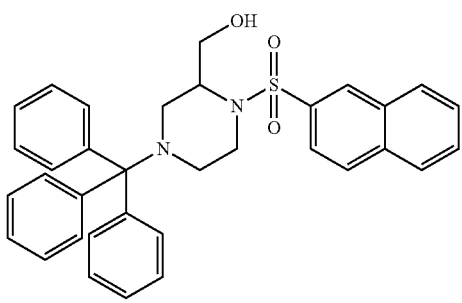

Intermediate 66 (0.0102 mol) was added portionwise at 0° C. to a suspension of $LiAlH_4$ (0.0203 mol) in THF (60 ml) under $N_2$ flow. Then THF (200 ml) was added. The mixture was stirred from 0° C. to room temperature for 2 hours. EtOAc, then water were added. The mixture was filtered over celite. Celite was washed with MeOH. The organic layer was separated, dried ($MgSO_4$), filtered, and the solvent was evaporated, yielding 5.3 g (95%) of intermediate 67. Part of this fraction (0.15 g) was crystallized from diethyl ether/DIPE. The precipitate was filtered off and dried, yielding 0.049 g of intermediate 67, melting point 277° C.

c) Preparation of intermediate 68

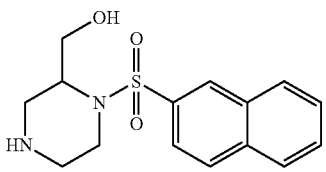

A mixture of intermediate 67 (0.0091 mol) in HCl 3N (3 ml) and 2-propanone (100 ml) was stirred at room temperature for 3 hours. The solvent was evaporated. Water was added. The mixture was extracted twice with diethyl ether. The organic layer was separated, dried ($MgSO_4$), filtered, and the solvent was evaporated, yielding 1.4 g (50%) intermediate 68. Part of this fraction (0.2 g) was crystallized from DIPE. The precipitate was filtered off and dried, yielding 0.08 g of intermediate 68, melting point 130° C.

d) Preparation of intermediate 69

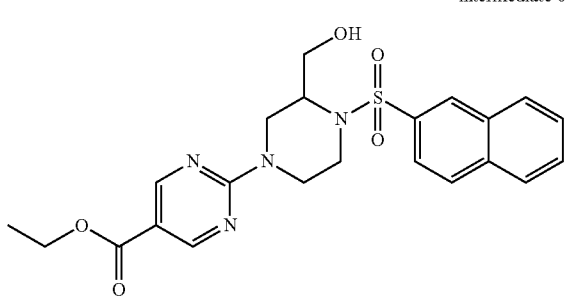

A mixture of intermediate 68 (0.0036 mol), 2-(methylsulfonyl)-5-pyrimidinecarboxylic acid, ethyl ester (0.0047 mol) and potassium carbonate (0.0072 mol) in acetonitrile (80 ml) was stirred at room temperature overnight, poured out into water and extracted with EtOAc. The organic layer was separated, dried ($MgSO_4$), filtered, and the solvent was evaporated. The residue (1.5 g) was purified by column chromatography over silica gel (15-40 µm) (eluent: DCM/MeOH/$NH_4OH$ 97/3/0.1). The fractions were collected and the solvent was evaporated. Yielding 0.91 g of intermediate 69. Part of this fraction (0.59 g) was crystallized from $CH_3CN$/DIPE. The precipitate was filtered off and dried, yielding 0.3 g of intermediate 69, melting point 151° C.

e) Preparation of intermediate 70

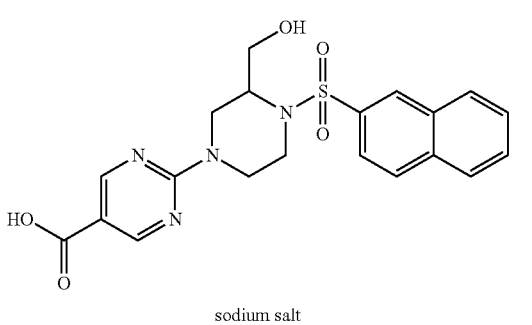

sodium salt

A mixture of intermediate 69 (0.0011 mol) and sodium hydroxide (0.0022 mol) in EtOH (30 ml) was stirred at 80° C. for 12 hours, then cooled to room temperature. The precipitate was filtered, washed with EtOH, then with diethyl ether and dried, yielding 0.36 g (72%) of intermediate 70. Na, melting point>260° C.

f) Preparation of intermediate 71

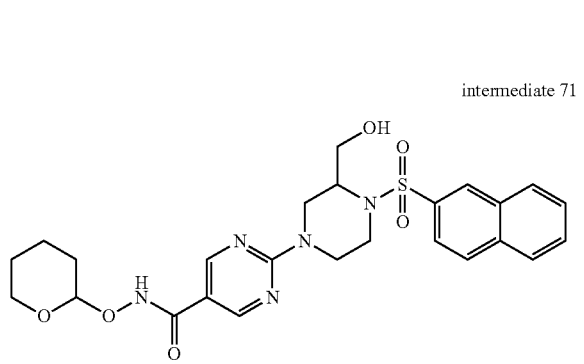 [SMILES: O=C(NOC1CCCCO1)c1cnc(N2CCN(S(=O)(=O)c3ccc4ccccc4c3)C(CO)C2)nc1]

1-hydroxybenzotriazole (0.001 mol) then EDC (0.001 mol) were added at room temperature to a mixture of intermediate 70 (0.0007 mol) and O-(tetrahydro-2H-pyran-2-yl)-hydroxylamine (0.001 mol) in DCM (20 ml) and THF (20 ml). The mixture was stirred at room temperature for 12 hours, poured out into water and extracted with DCM. The organic layer was separated, dried (MgSO$_4$), filtered, and the solvent was evaporated. The residue (0.4 g) was crystallized from CH$_3$CN/diethyl ether. The precipitate was filtered off and dried, yielding 0.17 g (41%) of intermediate 71, melting point 194° C.

Example A23 a) Preparation of intermediate 72

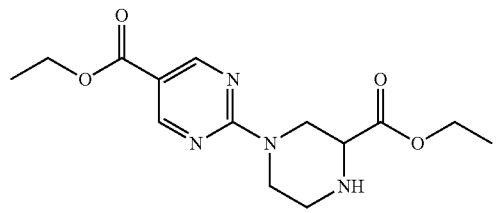

A mixture of 2-piperazinecarboxylic acid, ethyl ester (0.0108 mol), 2-(methylsulfonyl)-5-pyrimidinecarboxylic acid, ethyl ester (0.012 mol) and potassium carbonate (0.0215 mol) in acetonitrile (20 ml) was stirred at 80° C. for 24 hours, then cooled to room temperature, poured out into ice water and extracted with DCM. The organic layer was separated, dried (MgSO$_4$), filtered, and the solvent was evaporated, yielding 2.65 g of intermediate 72. This product was used directly in the next reaction step.

b) Preparation of intermediate 73

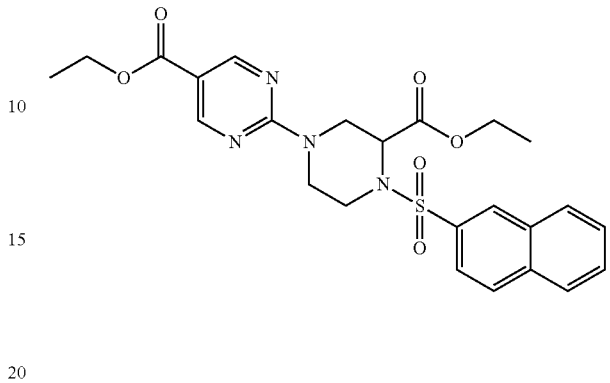

A solution of 2-naphthalenesulfonyl chloride (0.0095 mol) in DCM (30 ml) was added at 10° C. to a solution of intermediate 72 (0.0086 mol) and TEA (0.0172 mol) in DCM (30 ml). The mixture was stirred at room temperature for 6 hours, poured out into ice water and extracted with DCM. The organic layer was separated, dried (MgSO$_4$), filtered, and the solvent was evaporated. The residue (6.04 g) was purified by column chromatography over silica gel (eluent: cyclohexane/EtOAc 80/20; 15-40 nm). The pure fractions were collected and the solvent was evaporated. The residue (0.69 g, 16%) was crystallized from diethyl ether/DCM. The precipitate was filtered off and dried, yielding 0.45 g (10%) of intermediate 73, melting point 148° C.

c) Preparation of intermediate 74

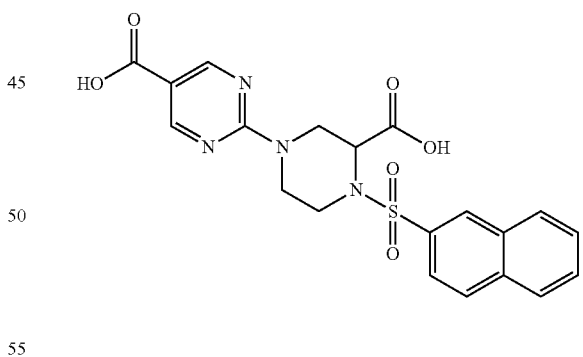

A mixture of intermediate 73 (0.0011 mol) and lithium hydroxide monohydrate (0.0044 mol) in THF (5 ml) and water (5 ml) was stirred at room temperature for 27 hours, poured out into ice water, acidified with HCl 3N and extracted with EtOAc. The organic layer was separated, dried (MgSO$_4$), filtered, and the solvent was evaporated. The residue (0.62 g) was crystallized from diethyl ether. The precipitate was filtered off and dried, yielding 0.26 g (54%) of intermediate 74, melting point 247° C.

d) Preparation of

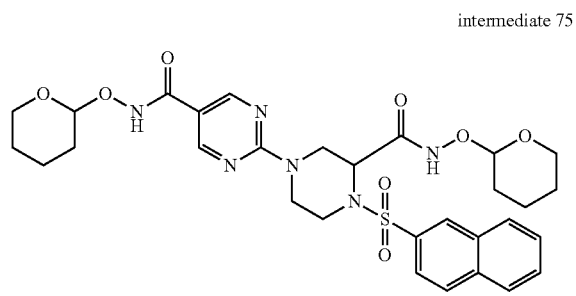 [SMILES: O=C(NOC1CCCCO1)c1cnc(N2CCN(S(=O)(=O)c3ccc4ccccc4c3)C(C(=O)NOC3CCCCO3)C2)nc1]

intermediate 75

EDC (0.0027 mol) then 1-hydroxybenzotriazole (0.0027 mol) were added at room temperature to a solution of intermediate 74 (0.001 mol) in TEA (0.0027 mol) and THF/DCM (16 ml) under $N_2$ flow. The mixture was stirred at room temperature for 48 hours, poured out into ice water and extracted with DCM. The organic layer was separated, dried (MgSO$_4$), filtered, and the solvent was evaporated. The residue (2.22 g) was purified by column chromatography over silica gel (15-40 μm) (eluent: DCM/MeOH/NH$_4$OH 97/3/0.1). The pure fractions were collected and the solvent was evaporated, yielding 0.242 g of intermediate 75.

Example A24 a) Preparation of

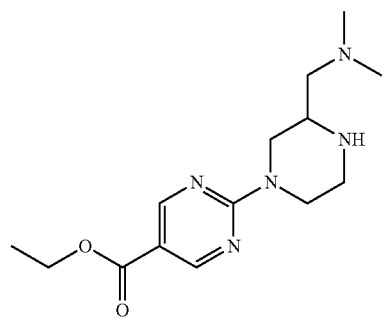

intermediate 76

A solution of 2-(methylsulfonyl)-5-pyrimidinecarboxylic acid, ethyl ester (0.0048 mol) in acetonitrile (20 ml) was added at 10° C. to a solution of N,N-dimethyl-2-piperazinemethanamine (0.01 mol) and potassium carbonate (0.02 mol) in acetonitrile (20 ml) under $N_2$ flow. The mixture was stirred at room temperature for 4 hours, poured out into ice water and extracted with DCM. The organic layer was separated, dried (MgSO$_4$), filtered, and the solvent was evaporated. The residue (2.25 g) was purified by column chromatography over silica gel (15-40 μm) (eluent: DCM/MeOH/NH$_4$OH 96/4/0.5). The pure fractions were collected and the solvent was evaporated, yielding 1.34 g (91%) of intermediate 76.

b) Preparation of

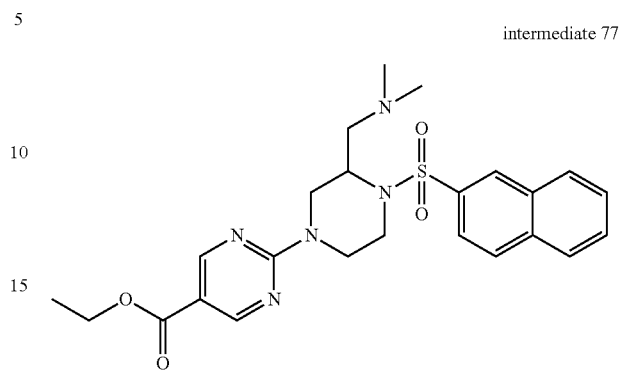

intermediate 77

A solution of 2-naphthalenesulfonyl chloride (0.0027 mol) in DCM (5 ml) was added dropwise at 10° C. to a solution of intermediate 76 (0.0018 mol) and TEA (0.0037 mol) in DCM (10 ml) under $N_2$ flow. The mixture was stirred at room temperature for 5 hours, poured out into ice water and extracted with DCM. The organic layer was separated, dried (MgSO$_4$), filtered, and the solvent was evaporated. The residue (1.22 g) was purified by column chromatography over silica gel (15-40 μm) (eluent: DCM/MeOH/NH$_4$OH 98/2/0.1). The pure fractions were collected and the solvent was evaporated. The residue (1.1 g) was crystallized from diethyl ether. The precipitate was filtered off and dried, yielding 0.74 g (84%) of intermediate 77, melting point 138° C.

c) Preparation of

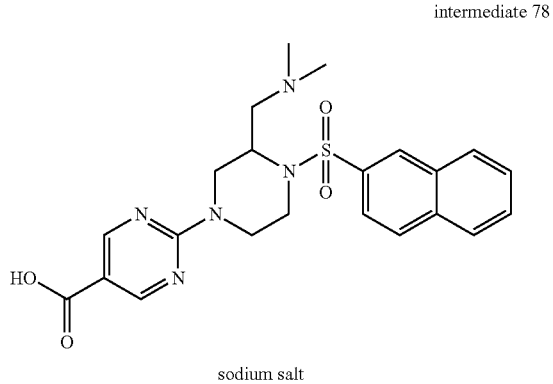 [SMILES: CN(C)CC1CN(c2ncc(C(=O)O)cn2)CCN1S(=O)(=O)c1ccc2ccccc2c1]

intermediate 78 sodium salt

A mixture of intermediate 77 (0.0014 mol) and sodium hydroxide (0.0057 mol) in EtOH (20 ml) was stirred and refluxed for 6 hours, then cooled to room temperature. The precipitate was filtered, washed with diethyl ether and dried, yielding 0.56 g (84%) of intermediate 78. Na. This product was used directly in the next reaction step.

d) Preparation of

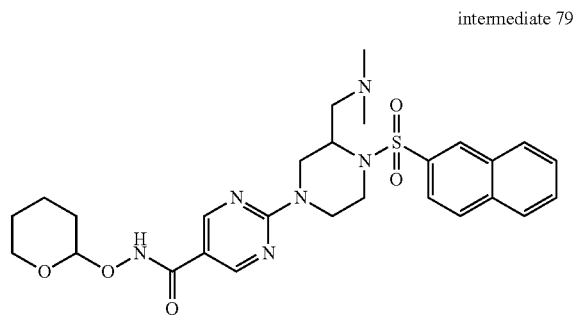 [SMILES: CN(C)CC1CN(c2ncc(C(=O)NOC3CCCCO3)cn2)CCN1S(=O)(=O)c1ccc2ccccc2c1]
intermediate 79 b) Preparation of

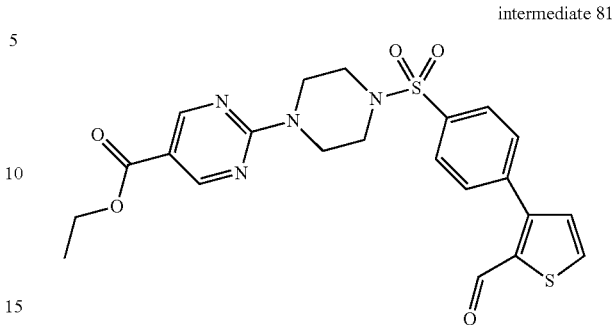
intermediate 81

EDC (0.0015 mol) and 1-hydroxybenzotriazole (0.0015 mol) were added at room temperature to a solution of intermediate 78 (0.0012 mol) in THF (5 ml) and DCM (5 ml) under $N_2$ flow. The mixture was stirred for 45 minutes. O-(tetrahydro-2H-pyran-2-yl)-hydroxylamine (0.0015 mol) was added. The mixture was stirred at room temperature overnight, poured out into ice water and extracted with DCM. The organic layer was separated, dried ($MgSO_4$), filtered, and the solvent was evaporated. The residue (0.62 g) was purified by column chromatography over silica gel (15-40 μm) (eluent: DCM/MeOH/$NH_4OH$ 94/6/0.1). The pure fractions were collected and the solvent was evaporated, yielding 0.55 g (77%) of intermediate 79, melting point 100° C.

Example A25 a) Preparation of

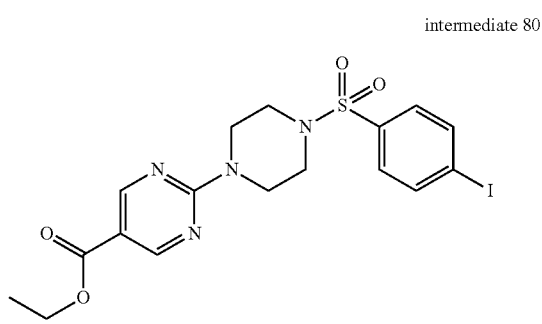 [SMILES: CCOC(=O)c1cnc(N2CCN(S(=O)(=O)c3ccc(I)cc3)CC2)nc1]
intermediate 80

A mixture of intermediate 30 (0.066 mol) in TEA (0.1 mol) and DCM (500 ml) was stirred at room temperature, then a solution of 4-iodo-benzenesulfonyl chloride (0.079 mol) in DCM (50 ml) was added dropwise at room temperature and the reaction mixture was stirred for 2 hours at room temperature. The mixture was washed with water, dried ($MgSO_4$) and the solvent was evaporated. The residue was suspended in $CH_3CN$, the resulting precipitate was filtered off, then washed with $CH_3CN$ and dried, yielding 27 g (81.4%) of intermediate 80, melting point 257° C.

Intermediate 80 (0.0995 mol) was suspended in DMF (250 ml) and the mixture was stirred for 5 minutes under $N_2$-atm. Cesium carbonate (0.0184 mol), then (2-formyl-3-thienyl)-boronic acid (0.0149 mol) was added and the reaction mixture was stirred for 5 minutes under $N_2$-atmosphere. Finally, dichlorobis(triphenylphosphine)-palladium (0.00199 mol) was added and the reaction mixture was stirred and refluxed at 80-100° C. for 3.5 hours under $N_2$-atm. The mixture was allowed to reach room temperature and the solvent was evaporated (vac.). The residue was suspended in acetonitrile and the resulting precipitate was filtered off, then purified by column chromatography over silica gel (eluent: DCM/MeOH from 100/0 to 98/2). The product fractions were collected, the solvent was evaporated and the residue was filtered off, then dried (vac.), yielding 4.250 g (87.8%) of intermediate 81.

c) Preparation of

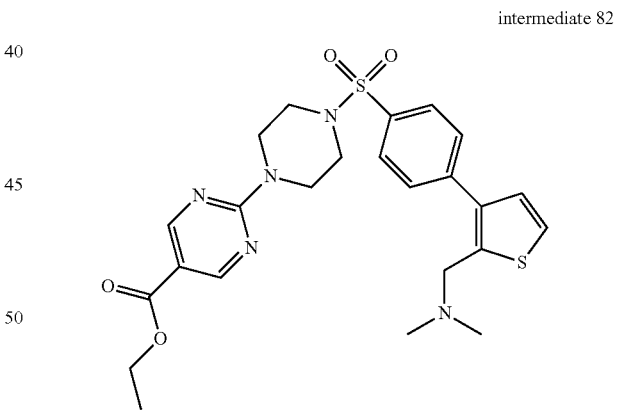
intermediate 82

A mixture of N-methyl-methanamine (0.011 mol) and intermediate 81 (0.0021 mol) in EtOH (100 ml) was hydrogenated overnight at 50° C. with Pd/C 10% (1 g) as a catalyst in the presence of thiophene solution (1 ml). After uptake of $H_2$ (1 equiv.), the reaction mixture was filtered over dicalite and the solvent was evaporated. The residue was purified by column chromatography over silica gel (gradient eluent: DCM/MeOH from 100/0 to 97/3). The product fractions were collected and the solvent was evaporated, yielding 0.54 g (51%) of intermediate 82.

d) Preparation of

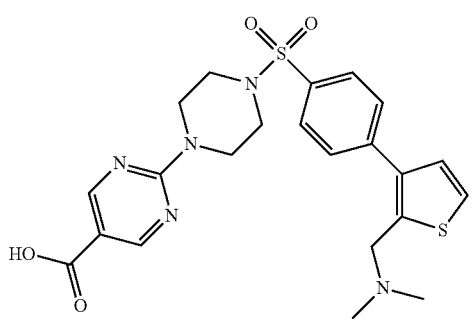
intermediate 83

A mixture of intermediate 82 (0.001 mol) and sodium hydroxide (0.010 mol) in THF (10 ml) was stirred for 4 days at room temperature, then HCl 1N (10 ml) was added and the reaction mixture was stirred for 10 min. The resulting precipitate was filtered off and dried under vacuum at 50° C. for 5 hours, yielding 0.47 g (92%) of intermediate 83 e) Preparation of

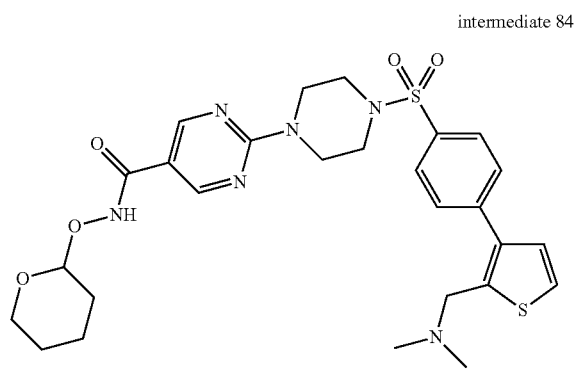 [SMILES: CN(C)Cc1sccc1-c1ccc(S(=O)(=O)N2CCN(c3ncc(C(=O)NOC4CCCCO4)cn3)CC2)cc1]
intermediate 84

Intermediate 83 (0.0009639 mol) was stirred in DCM (20 ml) and THF (20 ml), then N'-(ethylcarbonimidoyl)-N,N-dimethyl-1,3-propanediamine, monohydrochloride (0.001253 mol), 1-hydroxy-1H-benzotriazole (0.001253 mol) and O-(tetrahydro-2H-pyran-2-yl)-hydroxylamine (0.001253 mol) were added consecutively and the reaction mixture was stirred for 2 days at room temperature. Water was added and the organic layer was separated, dried (MgSO$_4$) and the solvent was evaporated. The residue was purified by column chromatography over silica gel (gradient eluent: DCM/MeOH from 100/0 to 97/3). The product fractions were collected and the solvent was evaporated, yielding 0.5 g (88.41%) of intermediate 84.

Example A26 a) Preparation of

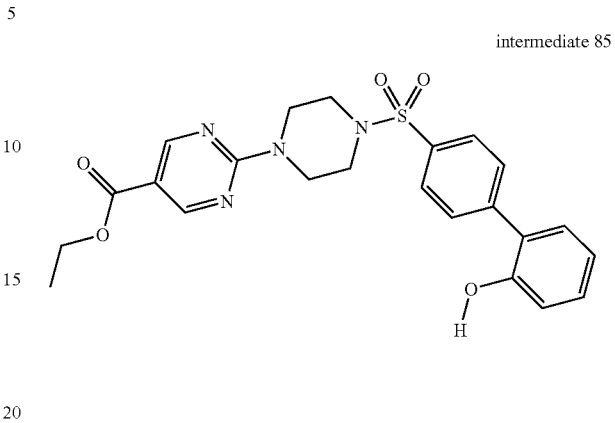
intermediate 85

A mixture of intermediate 80 (0.015 mol) in DMF (700 ml) was stirred for 15 min. under N$_2$-atmosphere, then cesium carbonate (0.023 mol) was added and the mixture was stirred for 5 min. under N$_2$-atm. 2-(4,4,5,5-tetramethyl-1,3,2-dioxaborolan-2-yl)-phenol (0.023 mol), then dichlorobis(triphenylphosphine)-palladium (0.00030 mol) was added and the reaction mixture was stirred for 4 hours at 80° C. under N$_2$-atm. The mixture was filtered over dicalite and this dicalite was washed with DCM and DMF. The organic layer was separated and concentrated. DCM was added and the mixture was washed with a 10% sodium carbonate solution, then the organic layer was separated, dried (MgSO$_4$), filtered and the solvent was evaporated. The residue was purified by column chromatography over silica gel (eluent: DCM/MeOH 97/3). The product fractions were collected and the solvent was evaporated, yielding 5.6 g (79%) of intermediate 85.

b) Preparation of

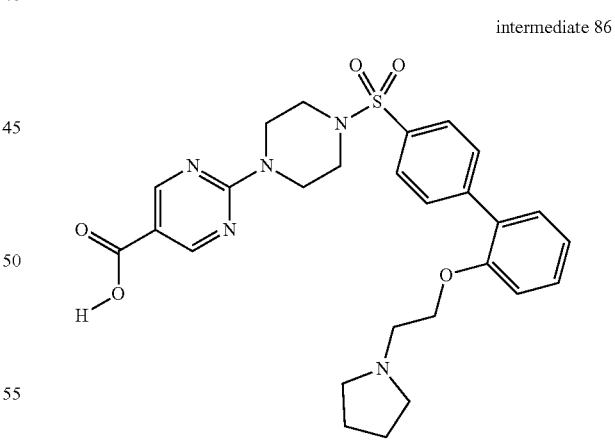
intermediate 86

The first part of this procedure was done 10 times: a mixture of 1-(2-chloroethyl)-pyrrolidine, hydrochloride (0.0006 mol) and intermediate 85 (0.0002 mol) in THF (4 ml) and sodium hydroxide (2 ml) was reacted in a microwave at 150° C. for 2 hours. Then, the 10 reaction mixtures were combined, diluted with water and acidified with HCl (1N) to pH: 4.5-5.5. The resulting precipitate was filtered off and dried (vac.), yielding 2 g of intermediate 86.

c) Preparation of

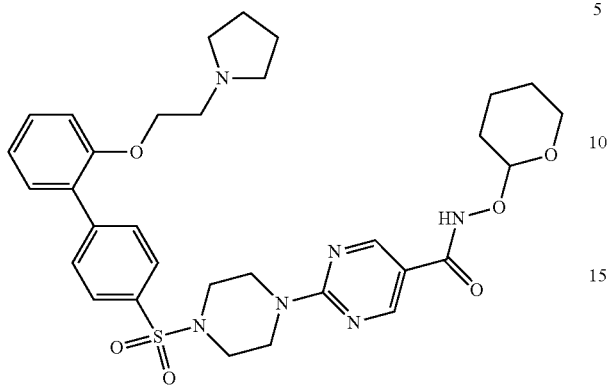

intermediate 87

Intermediate 86 (0.00372 mol) was stirred in DCM (50 ml) and THF (50 ml). TEA (0.03594 mol), then N'-(ethylcarbonimidoyl)-N,N-dimethyl-1,3-propanediamine, monohydrochloride (0.00372 mol), then 1-hydroxy-1H-benzotriazole (0.004836 mol) and finally O-(tetrahydro-2H-pyran-2-yl)-hydroxylamine (0.004836 mol) were added. The reaction mixture was stirred at room temperature for 1 day, then the mixture was dissolved in DCM and washed with water. The organic layer was separated, dried (MgSO$_4$), filtered and the solvent was evaporated. The residue was purified by column chromatography over silica gel (Biotage, 40M, gradient eluent: DCM/(MeOH/NH$_3$) from 100/0 to 93/7). The product fractions were collected and the solvent was evaporated, yielding 0.770 g of intermediate 87.

Example A27 a) Preparation of

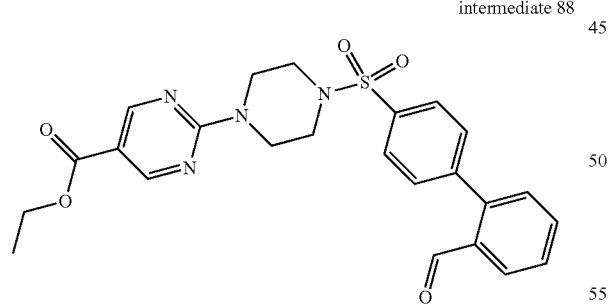

intermediate 88

Intermediate 80 (0.020 mol) was stirred in EtOH (500 ml), then stirred for 20 minutes under N$_2$-atm. at room temperature. (2-formylphenyl)-boronic acid (0.030 mol), then cesium carbonate (0.030 mol) and finally dichlorobis(triphenylphosphine)-palladium (0.00040 mol) was added. The reaction mixture was stirred and refluxed for 6 hours under N$_2$-atmosphere, then the solvent was evaporated. The residue was dissolved in DCM and washed with water. The organic layer was separated, dried (MgSO$_4$), filtered and the solvent was evaporated. The residue was purified by column chromatography over silica gel (gradient eluent: DCM/MeOH from 100/0 to 98/2). The product fractions were collected and the solvent was evaporated, yielding 5.1 g (53%) of intermediate 88.

b) Preparation of

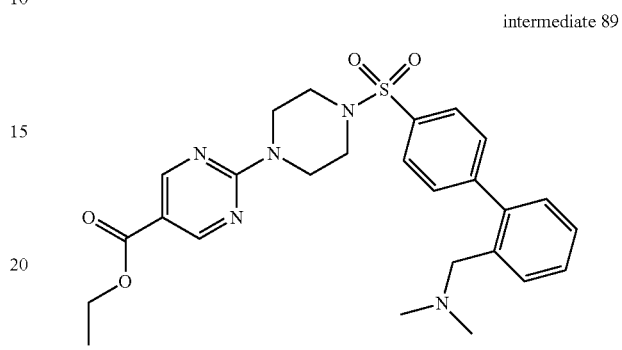

intermediate 89

A mixture of intermediate 88 (0.00208 mol) and N-methyl-methanamine (0.0222 mol) in MeOH (100 ml) was hydrogenated at room temperature for 1 day with Pd/C 10% (0.5 g) as a catalyst in the presence of thiophene solution (1 ml). After uptake of H$_2$ (1 equiv.), the reaction mixture was filtered over dicalite and the filtrate was evaporated. The residue was purified by column chromatography over silica gel (gradient eluent: DCM/MeOH from 100/0 to 90/10). The product fractions were collected and the solvent was evaporated. The residue was crystallised from acetonitrile, the resulting precipitate was filtered off, washed and dried (vac.), yielding 0.710 g (66.9%) of intermediate 89.

c) Preparation of

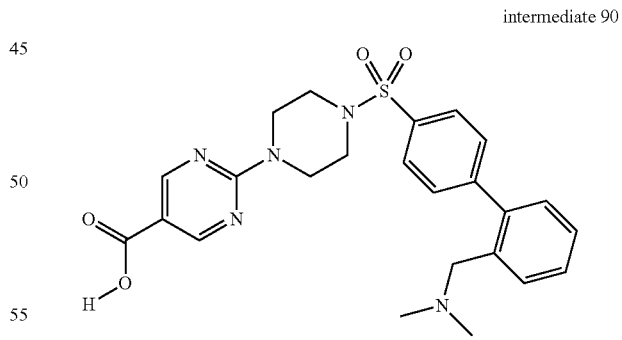

intermediate 90

A mixture of intermediate 89 (0.00139 mol) and sodium hydroxide 1N (0.010 mol) in THF (10 ml) and MeOH (2 ml) was stirred overnight at room temperature, then HCl 1N (10 ml) was added and the reaction mixture was stirred for 15 min. at room temperature. The resulting precipitate was filtered off and dried (vac., 60° C.), yielding 0.610 g (90.9%) of intermediate 90.

d) Preparation of

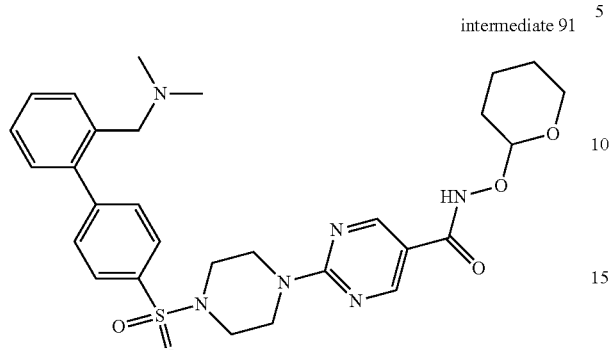

intermediate 91

Intermediate 90 (0.001267 mol) was stirred in DCM (50 ml) and THF (50 ml). TEA (0.007189 mol), then N'-(ethyl-carbonimidoyl)-N,N-dimethyl-1,3-propanediamine, monohydrochloride (0.001647 mol), then 1-hydroxy-1H-benzotriazole (0.001647 mol) and finally O-(tetrahydro-2H-pyran-2-yl)-hydroxylamine (0.001647 mol) were added. The reaction mixture was stirred at room temperature for 1 day, then the mixture was dissolved in DCM and washed with water. The organic layer was separated, dried (MgSO$_4$), filtered and the solvent was evaporated. The residue was crystallised from acetonitrile, the resulting precipitate was filtered off and dried (vac., 50° C.), yielding 0.560 g (76.13%) of intermediate 91.

Example A28 a) Preparation of

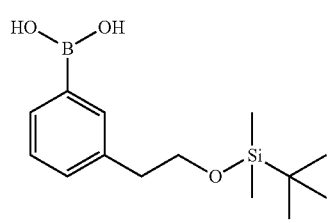

intermediate 92 nBuLi 1.6M in hexane (0.0069 mol) was added dropwise at −70° C. to a solution of [2-(3-bromophenyl)ethoxy](1,1-dimethylethyl)dimethyl-silane (0.0063 mol) in THF (20 ml) under N$_2$ flow. The mixture was stirred for 1 hour. Trisisopropoxyborane (0.0069 mol) was added dropwise. The mixture was stirred at −70° C. for 30 minutes, then brought to −20° C. Water was added. The mixture was extracted with DCM. The organic layer was separated, dried (MgSO$_4$), filtered, and the solvent was evaporated till dryness, yielding 1.8 g (100%) of intermediate 92.

b) Preparation of

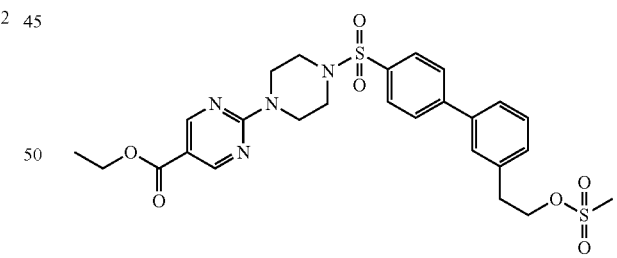

intermediate 93

A solution of intermediate 92 (0.0063 mol) in DMF (60 ml) was added to a mixture of intermediate 80 (0.0045 mol) and cesium carbonate (0.0063 mol) in DMF (20 ml). The mixture was stirred for 15 minutes. Tetrakis(triphenylphosphine)-palladium (0.0004 mol) was added. The mixture was stirred at 80° C. for 18 hours, then cooled to room temperature. HCl 3N was added. The mixture was stirred at room temperature for 3 hours, then filtered over celite. Celite was washed several times with water. The filtrate was taken up several times with DCM. The organic layer was washed with water, dried (MgSO$_4$), filtered, and the solvent was evaporated till dryness. The residue (2.4 g) was purified by column chromatography over silica gel (15-40 μm) (eluent: DCM/MeOH 99/1). The pure fractions were collected and the solvent was evaporated, yielding 1.76 g (78%) of intermediate 93.

c) Preparation of intermediate 94

Methanesulfonyl chloride (0.0133 mol) was added dropwise at 5° c. to a mixture of intermediate 93 (0.0044 mol) and TEA (0.0177 mol) in DCM (30 ml) under N$_2$ flow. The mixture was stirred for 1 hour, then brought to room temperature. Ice water was added. The mixture was extracted with DCM. The organic layer was separated, dried (MgSO$_4$), filtered, and the solvent was evaporated till dryness, yielding 3.43 g (>100%) of intermediate 94. This product was used without further purification.

d) Preparation of

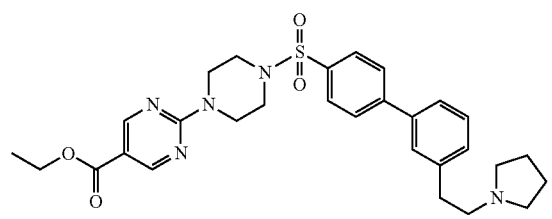

intermediate 95

A mixture of intermediate 94 (0.0014 mol), pyrrolidine (0.0147 mol) and potassium carbonate (0.0222 mol) in acetonitrile (20 ml) was stirred and refluxed for 18 hours. Water was added. The mixture was extracted with DCM/MeOH. The organic layer was separated, dried (MgSO$_4$), filtered, and the solvent was evaporated till dryness. The residue (1 g) was purified by column chromatography over silica gel (70-200 μm) (eluent: DCM/MeOH/NH$_4$OH 95/5/0.1). The pure fractions were collected and the solvent was evaporated, yielding 0.4 g (49%) of intermediate 95, melting point 190° C.

e) Preparation of

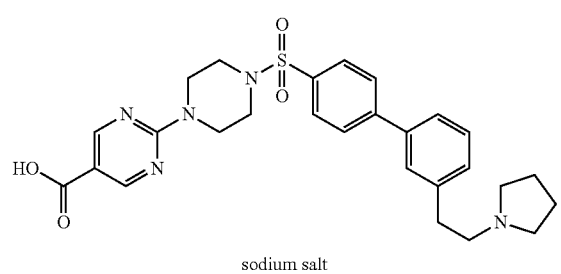

intermediate 96 sodium salt

A mixture of intermediate 95 (0.0007 mol) and sodium hydroxide (0.0014 mol) in EtOH (10 ml) was stirred and refluxed for 3 hours, then cooled to room temperature. The precipitate was filtered, washed with EtOH, then with diethyl ether and dried at 50° C. under a vacuo, yielding 0.35 g (88%) of intermediate 96. Na.

f) Preparation of

EDC (0.0008 mol) was added to a mixture of intermediate 96 (0.0006 mol), O-(tetrahydro-2H-pyran-2-yl)-hydroxylamine (0.0008 mol) and 1-hydroxybenzotriazole (0.0008 mol) in DCM/THF (10 ml) under N$_2$ flow. The mixture was stirred at room temperature for 18 hours. Water was added. The mixture was extracted with DCM. The organic layer was separated, dried (MgSO$_4$), filtered, and the solvent was evaporated till dryness. The residue (0.7 g) was purified by column chromatography over silica gel (5 μm) (eluent: DCM/MeOH/NH$_4$OH 92/8/0.1). The pure fractions were collected and the solvent was evaporated, yielding 0.31 g (77%) of intermediate 97.

Example A29 a) Preparation of

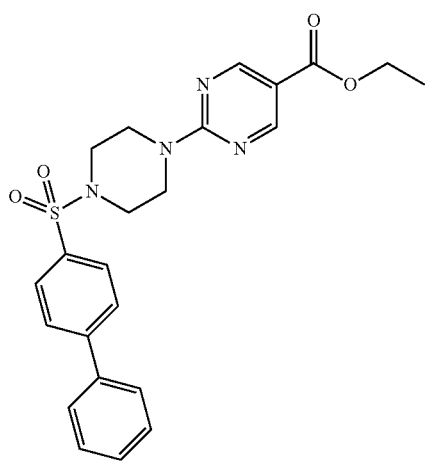

intermediate 98

A mixture of intermediate 30 (0.00021 mol), [1,1'-biphenyl]-4-sulfonyl chloride (±0.00032 mol, 1.5 equiv.) and morpholinomethyl-PS-scavenger (supplier: Novabiochem cat No 01-64-0171) (0.150 g) in DCM (5 ml) was stirred for 20 hours at room temperature, then Tris(2-aminoethyl)amine-PS scavenger (supplier: Novabiochem cat No 01-64-0170) (0.150 g) was added and the mixture was stirred for another 4 hours, yielding intermediate 98.

intermediate 97

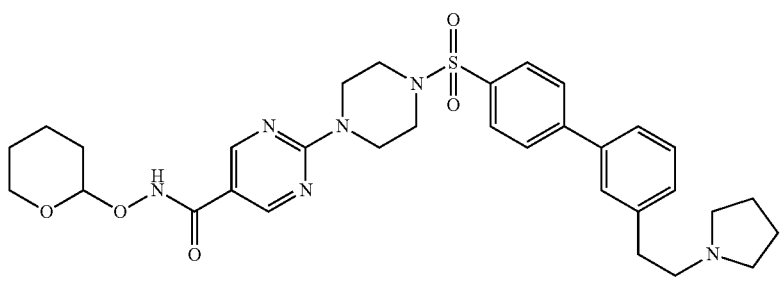

b) Preparation of

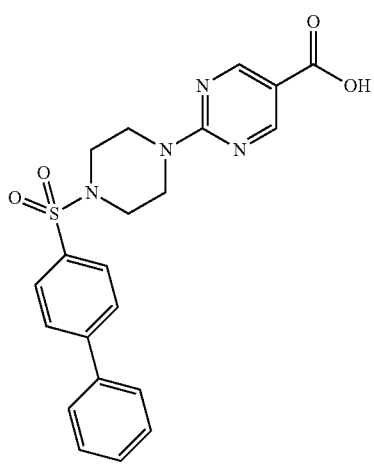
intermediate 99

A mixture of intermediate 98 (0.00021 mol) in sodium hydroxide 1N (1.5 ml), MeOH (1 ml) and THF (4 ml) was stirred at 60° C. for 2 hours, then stirred at room temperature for 20 hours. The reaction mixture was neutralized with 1.5 ml HCl 1N. The desired product was collected and dried, yielding intermediate 99.

c) Preparation of

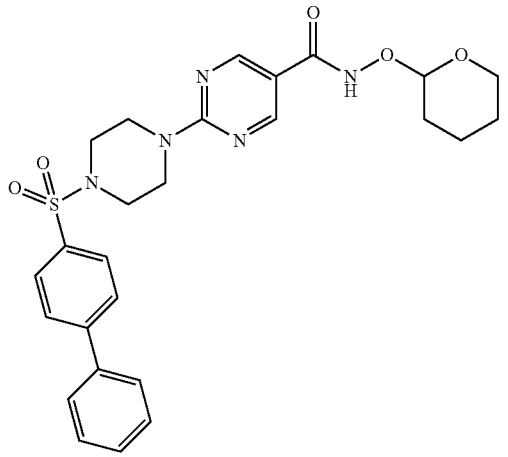
intermediate 100

A mixture of intermediate 99 (0.00021 mol), 1-hydroxy-1H-benzotriazole (0.00014 mol), N'-(ethylcarbonimidoyl)-N,N-dimethyl-1,3-propanediamine, monohydrochloride (0.00015 mol) and O-(tetrahydro-2H-pyran-2-yl)-hydroxylamine (0.00015 mol) in TEA (0.025 ml) and DCM/THF (10 ml) was stirred overnight at room temperature, then water (2 ml) was added and the reaction mixture was filtered through Extrelut™ NT (supplier: Merck). Isocyanate-PS-resin (supplier: Argonaut cat No 800260) (0.100 g) was added and the mixture was stirred at room temperature for 4 hours, then the resin was filtered off and the filtrate was evaporated. The residue was purified by column chromatography on Flashtube™ 2008 (supplier Trikonex) (eluent: DCM/EtOAc 1/1). The product fractions were collected and the solvents were evaporated, yielding intermediate 100.

Example A30 a) Preparation of

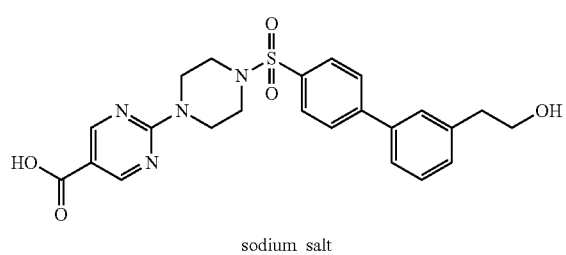
intermediate 101 sodium salt

A mixture of intermediate 93 (0.001 mol) and sodium hydroxide (0.004 mol) in EtOH (20 ml) was stirred and refluxed for 4 hours, then cooled to room temperature. Diethyl ether was added. The precipitate was filtered off and dried, yielding 0.476 g (97%) of intermediate 101.Na.

b) Preparation of

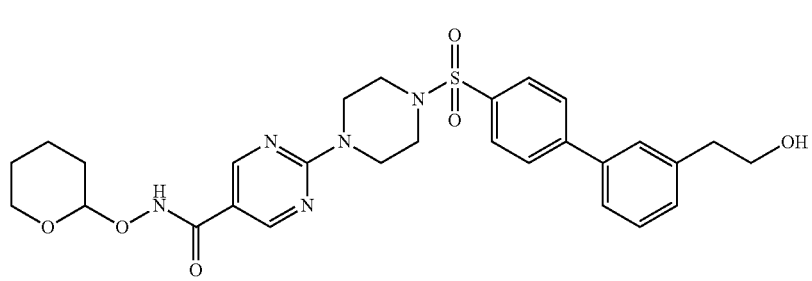
intermediate 102

EDC (0.0014 mol) and 1-hydroxybenzotriazole (0.0014 mol) were added at room temperature to a solution of intermediate 101 (0.0009 mol) in THF (5 ml) and DCM (5 ml). The mixture was stirred at room temperature for 30 minutes. O-(tetrahydro-2H-pyran-2-yl)-hydroxylamine (0.0014 mol) was added. The mixture was stirred at room temperature for 2 days, poured out into ice water and extracted with DCM. The organic layer was separated, dried (MgSO$_4$), filtered, and the solvent was evaporated. The residue (0.62 g) was purified by column chromatography over silica gel (5 μm) (eluent: DCM/MeOH/NH$_4$OH 97/3/0.3). The pure fractions were collected and the solvent was evaporated. The residue (0.38 g, 69%) was crystallized from diethyl ether. The precipitate was filtered off and dried, yielding 0.3 g (54%) of intermediate 102, melting point 214° C.

B. PREPARATION OF THE FINAL COMPOUNDS

Example B1

N-Fmoc-hydroxylamine 2-chlorotrityl resin (Novabiochem, 01-64-0165) was deprotected by 50% piperidine in DMF (RT, 24 hr)[1]. The resin was washed several times with DCM and DMF and swelled in DMF. Two equivalents of acid[3], PyBrOP[4] and 4 equivalents of DIEA were added as one portion. The mixture was shaken for 24 hr, liquid was drained and the resin was washed several times by DCM and DMF. The resin was swelled in DMF containing 2 equivalents of amine and was shaken 24 hr at RT. The liquid was drained and the resin was washed by DCM and DMF. An arylsulfonyl chloride (2 eq.) was added as one portion to the resin swelled in DMF with 4 equivalents of TEA. The reaction was stirred overnight, drained and the resin was washed by DCM and DMF. The final product was cleaved by 5% TFA in DCM, analysed by HPLC and MS and evaporated in the pre-weighted test-tubes.

[1]. In one example compound 16 glycinol 2-chlorotrityl-resin (Novabiochem, 01-64-0087) was used. In two other examples 2-chlorotritylchloride-resin (Novabiochem, 01-64-0114) and 1,2-phenylenediamine compound 17 or ethylenediamine compound 18 were used. In one other examples compound 19 carboxymethanethiol 4-methoxytrityl resin (Novabiochem, 01-64-0238) was used.

[2]. In some cases also MeOH was used in the different washing procedures compounds 16, 17, 18 and 19.

[3]. Based on the loading of the resin.

[4]. In some cases PyBrOP was replaced by PyBOP compounds 16, 17, 18 and 19.

For illustrative purposes the scheme hereunder is included.

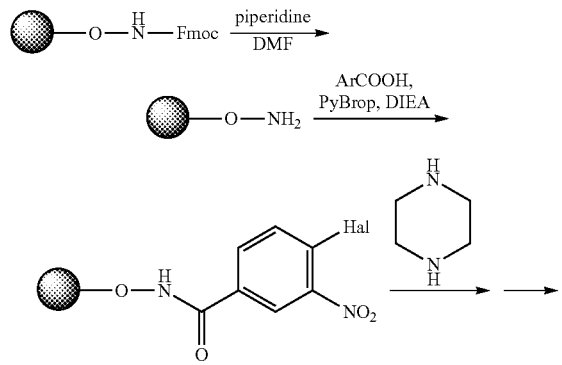

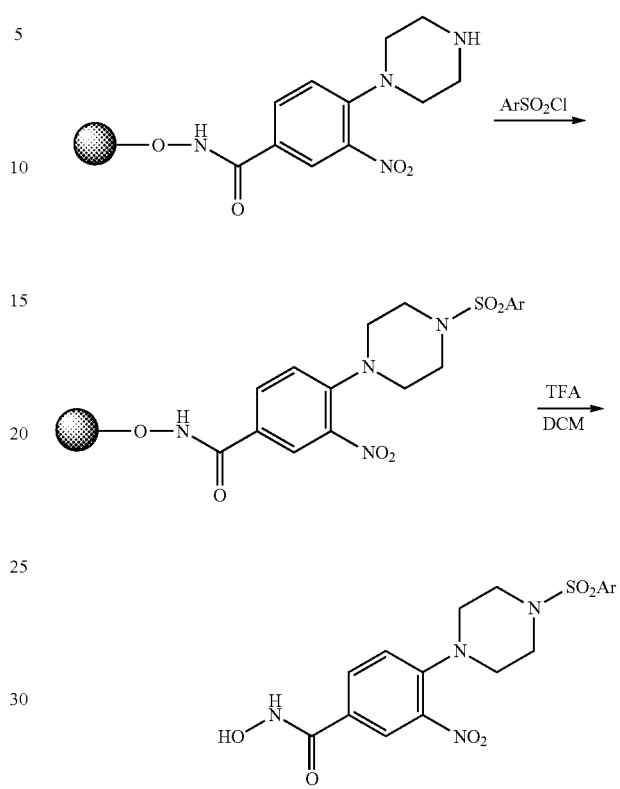

Example B2

Preparation of

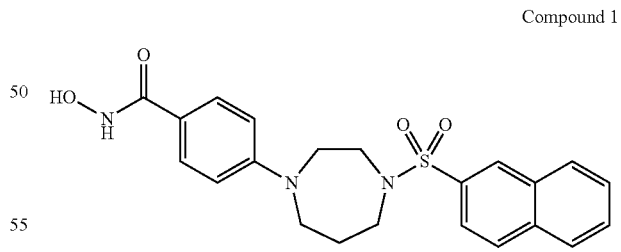

Compound 1

A mixture of interm. 3 (0.0027 mol) in DMF (100 ml) was hydrogenated for 48 hours at room temperature with Pd/C 10% (0.5 g) as a catalyst. After uptake of H$_2$ (1 equiv), the catalyst was filtered off and the filtrate was evaporated. The residue was triturated under DCM, filtered off, then recrystallized from HOAc, filtered off, washed with HOAc and ethanol, then dried, yielding 0.75 g (65%) of compound 1.

Example B3

Preparation of

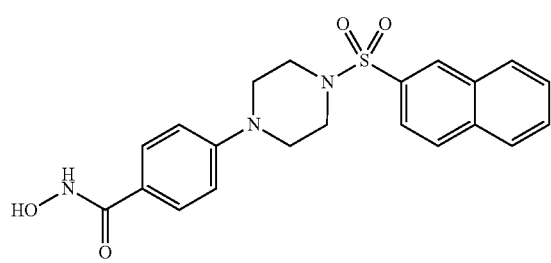

Compound 2

Interm. 6 (0.0022 mol) in THF (100 ml) was hydrogenated for 5 hours with Pd/C 10% (1 g) as a catalyst. After uptake of $H_2$ (1 equiv), the catalyst was filtered off over dicalite and the solvent was evaporated. The residue was suspended in DCM. The precipitate was filtered off, washed with a little DCM and dried (vacuum), yielding 0.9 g (100%) of compound 2.

Example B4

Preparation of

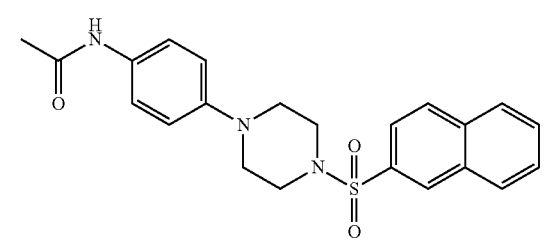

Compound 3

TEA (0.0008 mol) then acetyl chloride (0.0008 mol) were added to a mixture of interm. 7 (0.0008 mol) in DCM (5 ml) under $N_2$ flow. The mixture was kept at room temperature for 30 minutes, poured out into $K_2CO_3$ 10%/$H_2O$ and extracted with DCM. The organic layer was separated, dried ($MgSO_4$), filtered, and the solvent was evaporated till dryness. The residue (0.41 g) was purified by column chromatography over silica gel (eluent: DCM/MeOH 98/2; 10 µm). The pure fractions were collected and the solvent was evaporated. The residue (0.22 g, 66%) was crystallized from DCM/$CH_3CN$. The precipitate was filtered, washed with diethyl ether and dried, yielding 0.18 g (54%) of compound 3, melting point 200° C.

Example B5

Preparation of

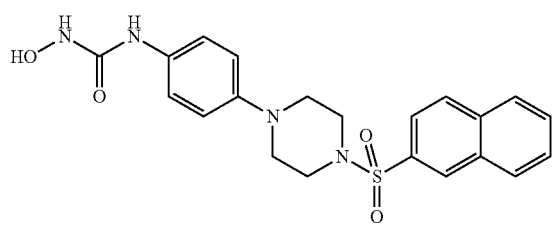

Compound 4

1,1-Carbonyldiimidazole (0.0003 mol) was added at room temperature to a solution of interm. 7 (0.0002 mol) in DCM (1 ml) under $N_2$ flow. The mixture was kept at room temperature for 1 hour. Hydroxylamine (0.0003 mol) was added. The mixture was stirred overnight. $K_2CO_3$ 10% was added. The mixture was extracted with DCM. The precipitate was filtered, washed with diethyl ether and dried, yielding 0.034 g (29%) of compound 4, melting point 210° C.

Example B6

Preparation of

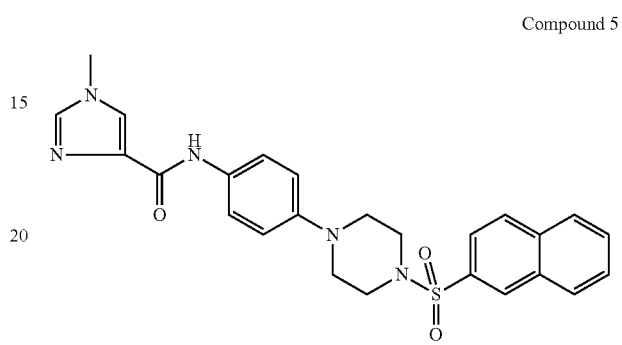

Compound 5

A mixture of interm. 7 (0.0013 mol), 1-methyl-1H-imidazole-4-carboxylic acid (0.002 mol), EDC (0.002 mol) and 1-hydroxybenzotriazole (0.002 mol) in DCM/THF (10 ml) was stirred at room temperature for 18 hours, poured out into $K_2CO_3$ 10% and extracted with DCM. The organic layer was separated, dried ($MgSO_4$), filtered, and the solvent was evaporated till dryness. The residue (1.3 g) was purified by column chromatography over silica gel (eluent: DCM/MeOH 98/2; 15-40 µm). The pure fractions were collected and the solvent was evaporated. The residue (0.25 g, 39%) was taken up in $CH_3CN$. The precipitate was filtered off and dried, yielding 0.15 g (23%) of compound 5, melting point 252° C.

Example B7

Preparation of

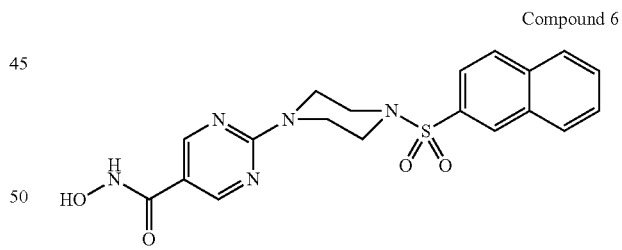

Compound 6

TFA (4 ml) was added at 0° C. to a solution of interm. 10 (0.0005 mol) in MeOH (20 ml). The mixture was stirred at room temperature for 48 hours. The solvent was evaporated till dryness. The residue was taken up in diethyl ether. The precipitate was filtered off and dried, yielding 0.195 g (83%) of compound 6, melting point 265° C. Another procedure for making compound 6:

$CF_3COOH$ (25 ml) was added to a mixture of interm. 33 (0.012 mol) in DCM p.a. (250 ml) and MeOH p.a. (250 ml). The reaction mixture was stirred for 24 hours at room temperature. The precipitate was filtered off, suspended in hot $CH_3CN$, then allowed to cool to room temperature while stirring, then filtered off, washed with $CH_3CN$, and dried (vacuum, 50° C.), yielding 3.43 g of compound 6. The corresponding filtrate was concentrated. The solid residue was suspended in hot CH$_3$CN, stirred, allowed to cool to room temperature, filtered off and dried (vacuum, 50° C.), yielding 1.22 g of compound 6. Total yielding 4.65 g (94%) of compound 6.

Example B8

Preparation of compound 7

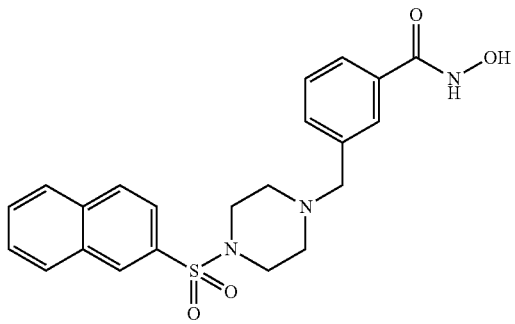

A mixture of interm. 13 (0.000049 mol) in 5% CF$_3$COOH/MeOH (5 ml) was shaken for 40 hours at room temperature. The solvent was evaporated under a stream of N$_2$, at room temperature. DCM was added, and then evaporated again. Dioxane was added, and then evaporated again under a stream of N$_2$, at room temperature. DCM was added and the solvent was evaporated at 30° C. under a stream of N$_2$. The residue was dried over the weekend at 40° C. in vacuo, yielding 0.024 g of compound 7.

Example B9

Preparation of compound 8

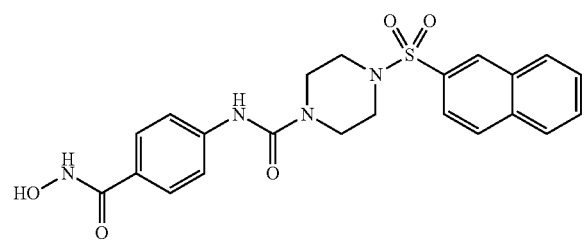

A mixture of interm. 17 (0.00018 mol) in 5% CF$_3$COOH/MeOH (6 ml) was stirred over the weekend at room temperature. The mixture was blown dry under a gentle stream of N$_2$. The residue was suspended in EtOAc, then filtered off and dried in vacuo, yielding 0.0222 g of compound 8.

Example B10

Preparation of compound 9

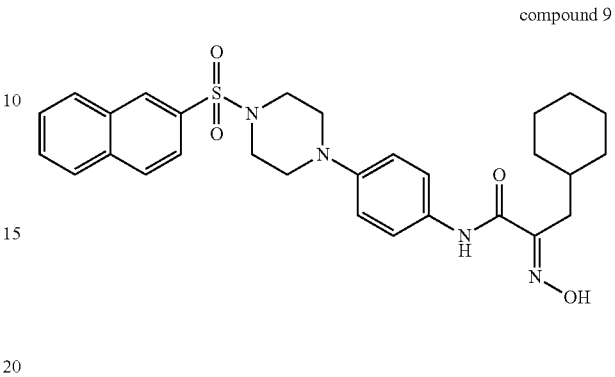

Methanesulfonic acid (1.5 ml) was added at room temperature to a mixture of interm. 20 (0.0018 mol) in MeOH (15 ml). The mixture was kept for 18 hours. Ice was added. The mixture was basified with K$_2$CO$_3$ 10% and extracted with DCM. The organic layer was washed with water, dried (MgSO$_4$), filtered and the solvent was evaporated till dryness. The residue (1.1 g) was crystallized from DCM/MeOH. The precipitate was filtered off and dried, yielding 0.68 g (76%) of compound 9 (E configuration), melting point. 226° C.

Example B11

Preparation of compound 10

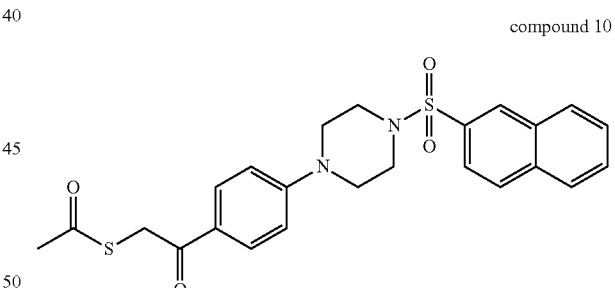

Ethanethioic acid (0.0023 mol) was added at 0° C. to a mixture of interm. 22 (0.0021 mol) and TEA (0.0032 mol) in 2-propanone (10 ml). The mixture was brought to room temperature, and then stirred for 2 hours. Water was added. The mixture was extracted with DCM. The organic layer was washed twice with water, dried (MgSO$_4$), filtered, and the solvent was evaporated. The residue (0.85 g) was purified by column chromatography over silica gel (eluent: cyclohexane/EtOAc 70/30; 10 um). The fractions were collected and the solvent was evaporated. The residue was crystallized from diethyl ether. The precipitate was filtered off and dried, yielding 0.088 g (10%) of compound 10, melting point 179° C.

Example B12

Preparation of

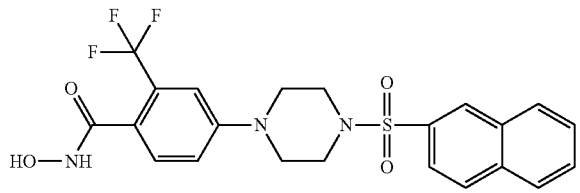

compound 11

CF$_3$COOH (0.7 ml) was added to a solution of interm. 25 (0.0007 mol) in MeOH (7 ml) and DCM (7 ml). The mixture was stirred at room temperature overnight. The precipitate was filtered, washed with diethyl ether and dried. The residue (0.23 g, 68%) was dried again, yielding 0.194 g (57%) of compound 11, melting point 196° C.

Example B13

Preparation of

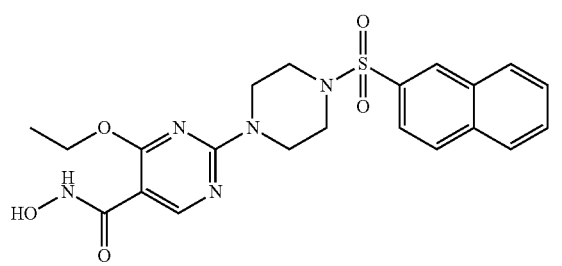

compound 12

CF$_3$COOH (2.6 ml) was added to a solution of interm. 28 (0.0005 mol) in MeOH (12 ml) and DCM (10 ml). The mixture was stirred at 24° C. overnight. The solvent was evaporated till dryness. The residue was crystallized from DCM/diethyl ether. The precipitate was filtered off and dried, yielding 0.124 g (49%) of compound 12, melting point 197° C.

Example B14

Preparation of

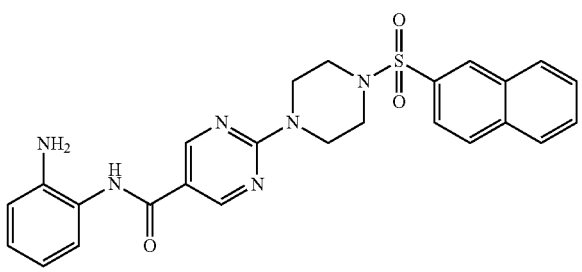

compound 13

EDC (0.0026 mol) and 1-hydroxybenzotriazole hydrate (0.0023 mol) were added at room temperature to a solution of interm. 32 (0.0017 mol) and TEA (0.0021 mol) in DMF (14 ml). The mixture was stirred for 1 hour. 1,2-Benzenediamine (0.0021 mol) was added. The mixture was stirred at room temperature overnight, then at 60° C. for 3 hours, poured out into ice water and extracted with EtOAc. The organic layer was separated, dried (MgSO$_4$), filtered, and the solvent was evaporated. The residue (0.9 g) was purified by column chromatography over silica gel (eluent: DCM/MeOH/NH$_4$OH 97/3/0.1; 15-40 μm). The pure fractions were collected and the solvent was evaporated. The residue (0.45 g) was crystallized from diethyl ether. The precipitate was filtered off and dried, yielding 0.414 g (48%) of compound 13, melting point 238° C.

Example B15

Preparation of

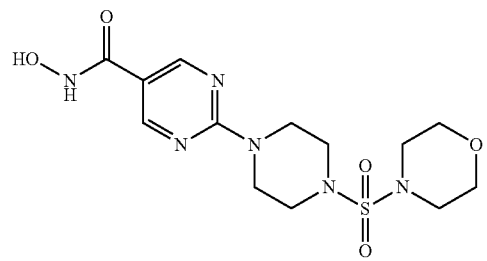

compound 14

CF$_3$COOH (0.2 ml) was added at 0° C. to a mixture of interm 36 (0.0005 mol) in MeOH (1 ml) and DCM (1 ml). The mixture was stirred at room temperature for 24 hours. The solvent was evaporated till dryness, yielding 0.0174 g (89%) of compound 14.

Example B16

Preparation of

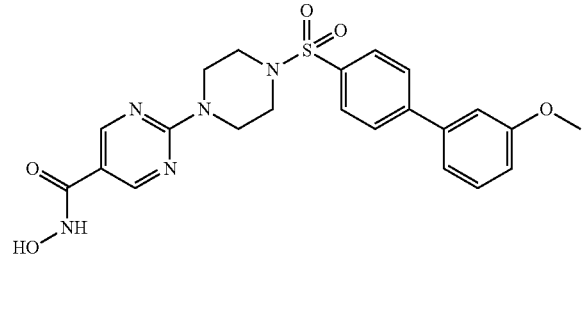

compound 15

Interm. 40. (0.0903 mmol) was dissolved in DCM (2 ml) and MeOH (3 ml). Trifluoroacetic acid (250 μl) was added. The mixture was stirred for 2 days at room temperature. The solvent was evaporated at room temperature under N$_2$-blow. Two times dioxane was added. The products were blowed and dried at 40° C. under N$_2$-blow, yielding compound 15.

Example B17

Preparation of compound 113

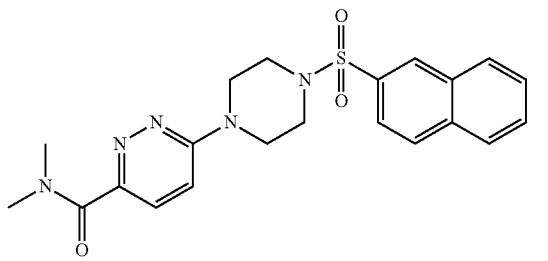

Pd(PPh$_3$)$_4$ (0.0002 mol) and potassium carbonate (0.0056 mol) were added to a mixture of intermediate 41 (0.0028 mol) in EtOH (22 ml) and DMF (22 ml). The mixture was stirred at 80° C. for 48 hours under a 5 bar pressure of CO, then taken up in EtOAc/H$_2$O and filtered over celite. The organic layer was washed with water, dried (MgSO$_4$), filtered and the solvent was evaporated. The residue was purified by column chromatography over silica gel (15-40 μm) (eluent: DCM/MeOH/NH$_4$OH 98/2/0.1). The pure fractions were collected and the solvent was evaporated, yielding 0.27 g (23%) of compound 113, melting point 200° C.

Example B18

Preparation of compound 114

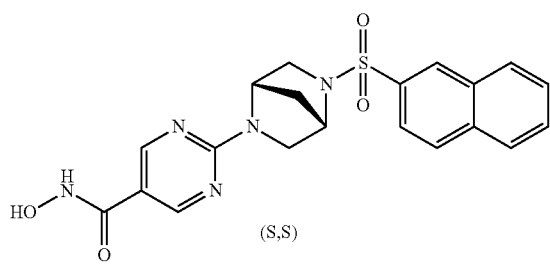

(S,S)

TFA (0.5 ml) was added at 0° C. to a mixture of intermediate 46 (S,S) (0.0006 mol) in MeOH (10 ml). The mixture was brought to room temperature, then stirred for 12 hours. TFA was added again. The mixture was stirred at room temperature for 72 hours. The precipitate was filtered, washed with MeOH, then with diethyl ether and dried. The residue (0.276 g) was dried at 60° C. for 4 hours, yielding 0.258 g, then dried at 75° C. for 8 hours, and then taken up in DCM and stirred at room temperature. The precipitate was filtered, washed with diethyl ether and dried, yielding 0.158 g (56%) of compound 114 (S,S).

Example B19

Preparation of compound 115

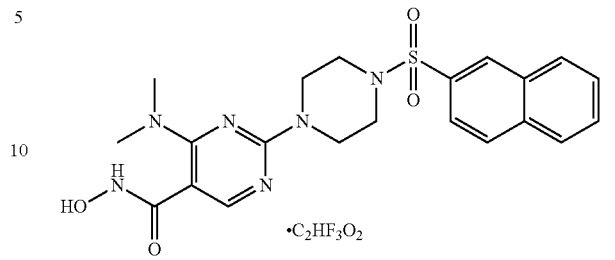

·C$_2$HF$_3$O$_2$

A mixture of intermediate 49 (0.0001 mol) in TFA (2 ml), MeOH (4 ml) and DCM (3 ml) was stirred at room temperature for 19 days. The solvent was evaporated. The residue was crystallized from diethyl ether. The precipitate was filtered, yielding yielding 0.0852 g (85%) of compound 115, melting point 135° C.

Example B20

Preparation of compound 116

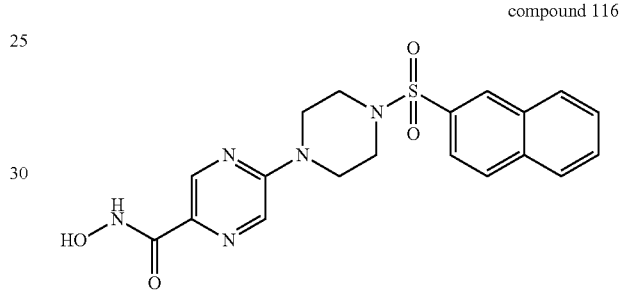

TFA (10 ml) was added at 0° C. to a solution of intermediate 52 (0.0051 mol) in MeOH (50 ml) and DCM (50 ml). The mixture was stirred at room temperature for 48 hours. The precipitate was filtered, washed with diethyl ether and dried, yielding 2.07 g (97%) of compound 116, melting point 249° C.

Example B21

Preparation of compound 117

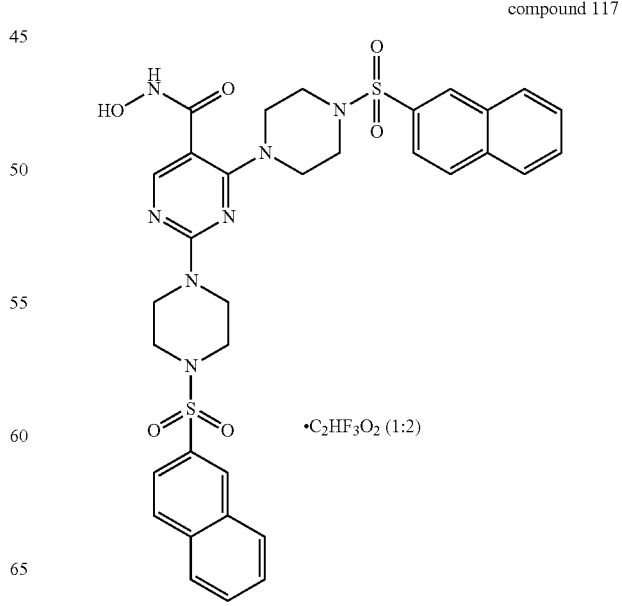

·C$_2$HF$_3$O$_2$ (1:2)

A mixture of intermediate 55 (0.00003 mol) in TFA (0.5 ml), MeOH (3 ml) and DCM (2 ml) was stirred at room temperature for 5 days. The solvent was evaporated till dryness, yielding 0.017 g (62%) of compound 117. 2C$_2$HF$_3$O$_2$, melting point 80° C.

Example B22

Preparation of compound 118

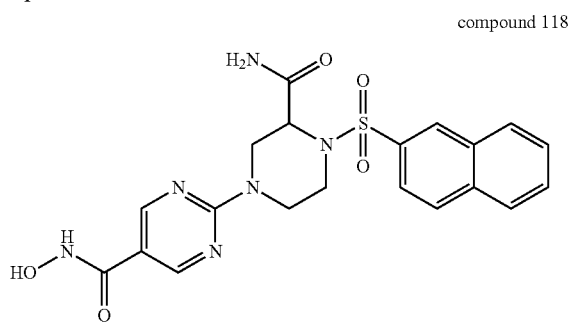

A mixture of intermediate 60 (0.0022 mol) in TFA (3 ml), MeOH (10 ml) and DCM (10 ml) was stirred at room temperature for 24 hours. Diethyl ether was added. The precipitate was filtered off and dried, yielding 1 g (97%) of compound 118, melting point 210° C.

Example B23

Preparation of compound 119

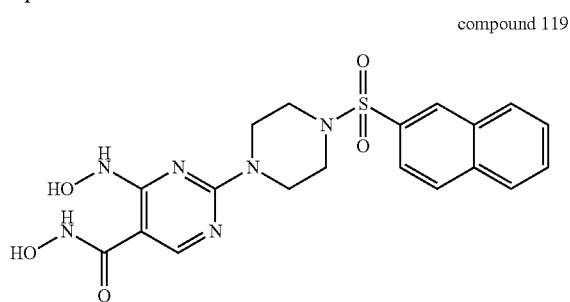

A mixture of intermediate 62 (0.0024 mol) in TFA (5 ml), MeOH (22 ml) and DCM (10 ml) was stirred at room temperature for 8 days, then filtered. The precipitate was discarded and the filtrate was evaporated. The residue (1.4 g) was crystallized from DCM/MeOH/CH$_3$CN/diethyl ether. The precipitate was filtered off and dried, yielding 0.388 g (36%) of compound 119, melting point 225° C. (purity: 90%).

Example B24

Preparation of compound 120

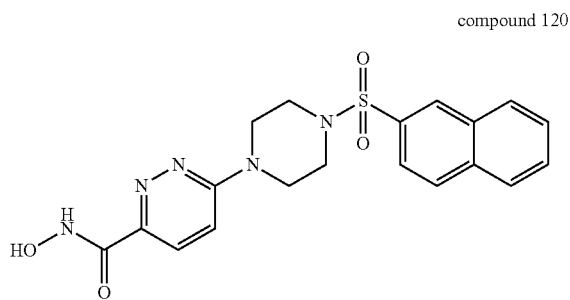 [SMILES: O=C(NO)c1ccc(N2CCN(S(=O)(=O)c3ccc4ccccc4c3)CC2)nn1]

A mixture of intermediate 65 (0.0004 mol) in TFA (2 ml), MeOH (20 ml) and DCM (10 ml) was stirred at room temperature for 72 hours. The solvent was evaporated. Diethyl ether was added. The precipitate was filtered off and dried, yielding 0.19 g (94%) of compound 120, melting point>260° C.

Example B25

Preparation of compound 121

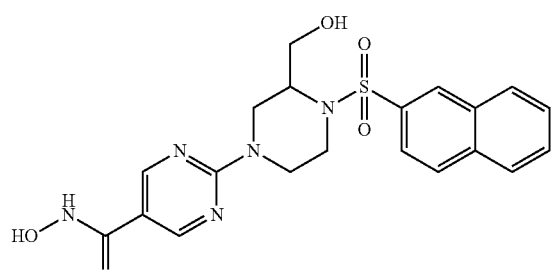

A mixture of intermediate 71 (0.0003 mol) in TFA (1 ml) and MeOH (10 ml) was stirred at room temperature for 4 days. The precipitate was filtered, washed with MeOH, then with diethyl ether and dried, yielding 0.096 g (72%) of compound 121, melting point 220° C.

Example B26

Preparation of compound 122

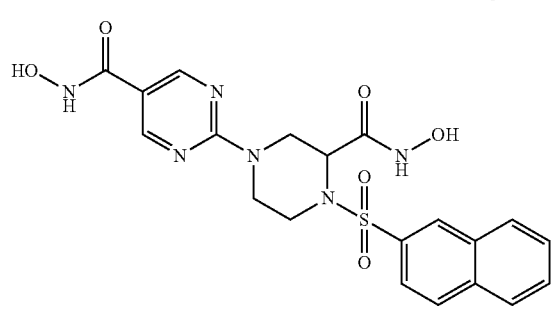

A mixture of intermediate 75 (0.0003 mol) in TFA (2 ml) and MeOH (5 ml) was stirred at room temperature for 72 hours. The precipitate was filtered, washed with diethyl ether and dried, yielding 0.112 g (63%) of compound 122, melting point 166° C.

Example B27

Preparation of compound 123

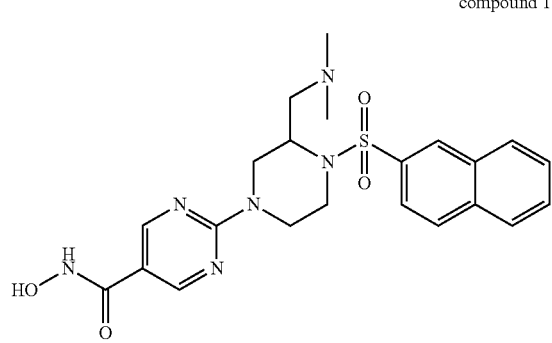

·C$_2$HF$_3$O$_2$

A mixture of intermediate 79 (0.0009 mol) in TFA (0.5 ml) and MeOH (5 ml) was stirred at room temperature for 48 hours then evaporated till dryness. The residue was taken up in MeOH/diethyl ether. The precipitate was filtered off and dried, yielding 0.42 g (82%) of compound 123. $C_2HF_3O_2$, melting point 114° C.

Example B28

Preparation of compound 124

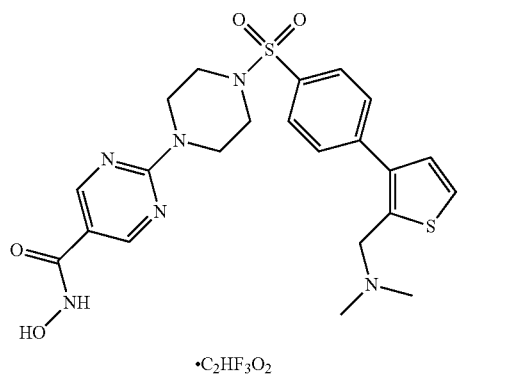

•$C_2HF_3O_2$

Intermediate 84 (0.000852 mol) was stirred in TFA (5% in MeOH/DCM) (40 ml) for 3 days, then the resulting precipitate was filtered off and dried (vac., 50° C.), yielding 0.316 g (60%) of compound 124. $C_2HF_3O_2$, melting point 192° C.

Example B29

Preparation of compound 125

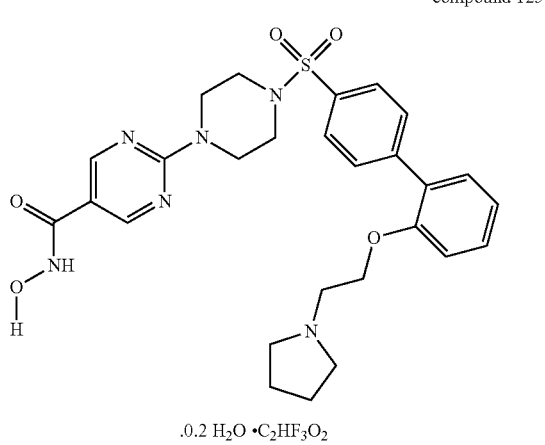

.0.2 $H_2O$ •$C_2HF_3O_2$

A mixture of intermediate 87 (0.00121 mol) in TFA (5% in MeOH) (60 ml) was stirred for 6 days at room temperature (after 4 days 0.25 ml TFA was added) and the solvent was evaporated (vac.) at room temperature. The residue was crystallised from EtOAc by reflux, the resulting precipitate was filtered off and dried (vac.), yielding 0.356 g (44.2%) of compound 125. 0.2 $H_2O.C_2HP_3O_2$, melting point 146.9° C.

Example B30

Preparation of compound 126

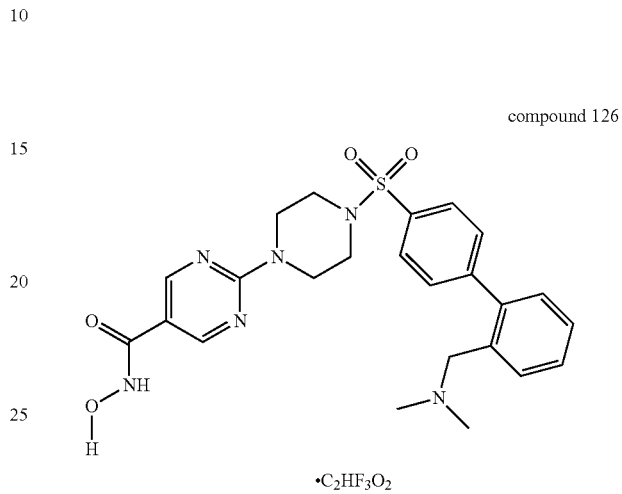

•$C_2HF_3O_2$

Intermediate 91 (0.00096 mol) was stirred in TFA (40 ml, 5% in DCM/MeOH) at room temperature for 4 days and the solvent was partly evaporated (vac.) at room temperature. Precipitation resulted in the concentrate and the precipitate was filtered off, then dried (vac., 50° C.), yielding 0.455 g (78%) of compound 126. $C_2HF_3O_2$, melting point 190, 7° C.

Example B31

Preparation of compound 127

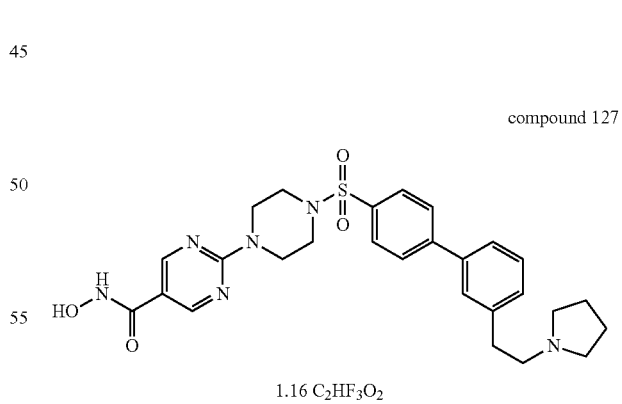

1.16 $C_2HF_3O_2$

TFA (0.5 ml) was added to a mixture of intermediate 97 (0.0004 mol) in MeOH (10 ml). The mixture was stirred at room temperature for 18 hours. The precipitate was filtered off and dried, yielding 0.22 g (66%) of compound 127. 1.16 $C_2HF_3O_2$, melting point 243° C.

Example B32

Preparation of compound 128

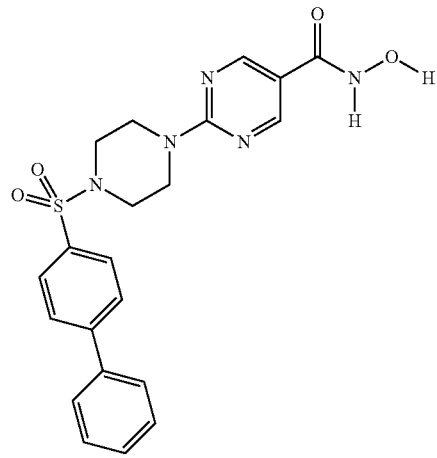

A mixture of intermediate 100 (0.00021 mol) in TFA (5 ml, 5% in MeOH) and DCM (1 ml) was stirred at room temperature for 48 hours, then the solvent was evaporated, yielding compound 128.

Example B33

Preparation of compound 129

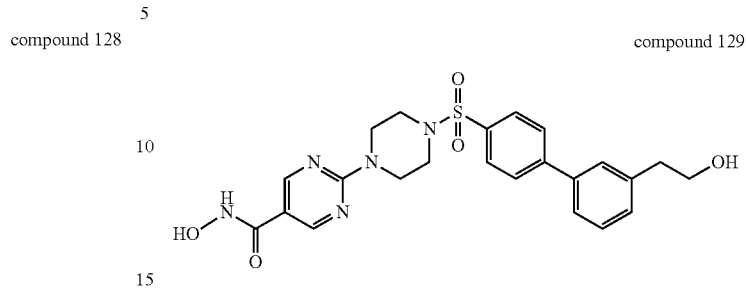

A mixture of intermediate 102 (0.0005 mol) in TFA (1.2 ml), MeOH (10 ml) and DCM (2 ml) was stirred at room temperature for 3 days. Diethyl ether was added. The precipitate was filtered off and dried, yielding 0.232 g (94%) of compound 129, melting point>260° C.

Table F-1 lists the compounds that were prepared according to one of the above Examples. The following abbreviations were used in the tables: Co. No. stands for Compound Number, Ex. [Bn°] referred to the same method as described in the Bn° examples, $C_2HF_3O_2$ stands for the trifluoroacetate salt. Some compounds have been characterized via melting point (mp.), other compounds were characterized via Mass Spectral data [MH$^+$] (ms.).

TABLE F-1

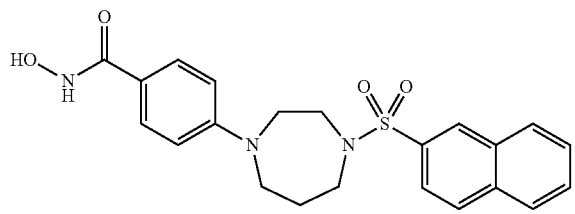

Co. No. 1; Ex. [B2]

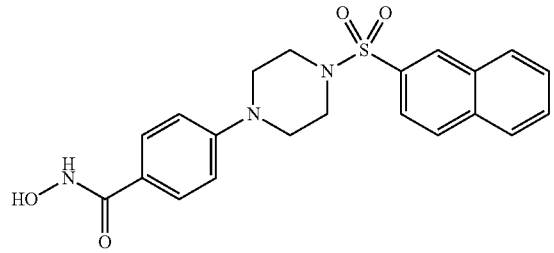

Co. No. 2; Ex. [B3]

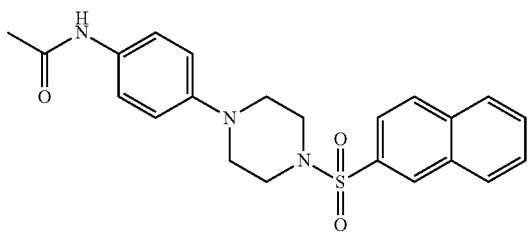

Co. No. 3; Ex. [B4]; mp. 200° C.

TABLE F-1-continued
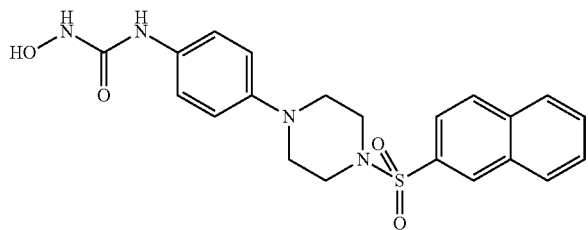
Co. No. 4; Ex. [B5]; mp. 210° C.
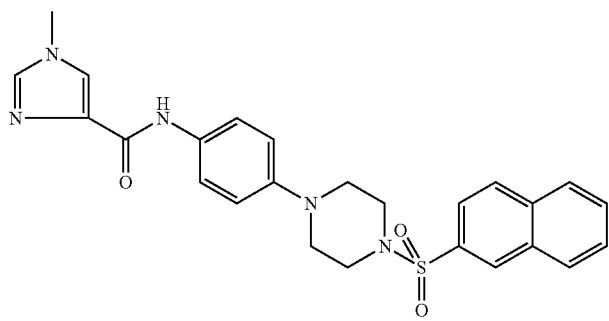
Co. No. 5; Ex. [B6]; mp. 252° C.
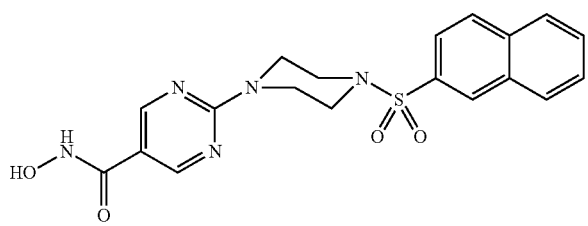
Co. No. 6; Ex. [B7]; mp. 265° C.
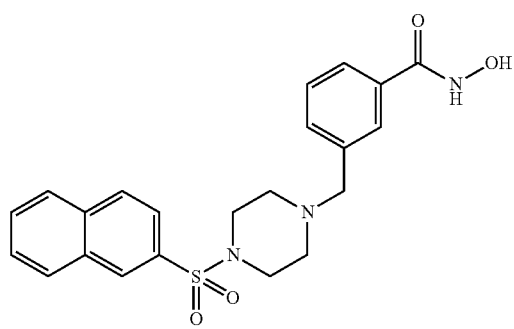
Co. No. 7; Ex. [B8]
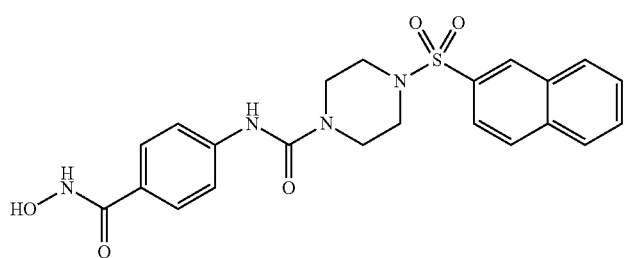
Co. No. 8; Ex. [B9]

TABLE F-1-continued
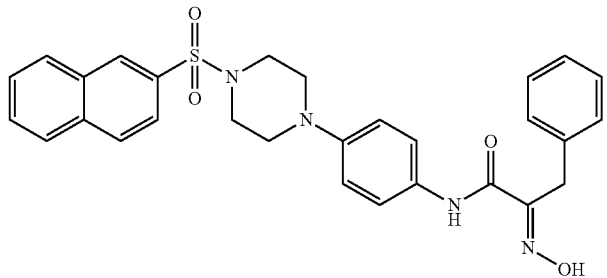
Co. No. 9; Ex. [B10]; mp. 226° C.
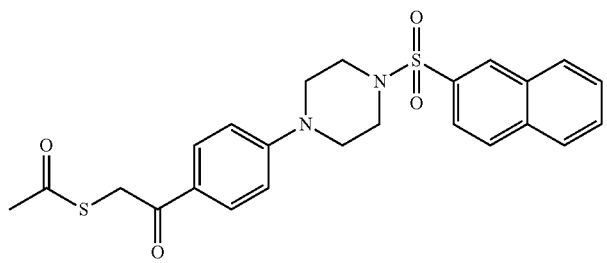
Co. No. 10; Ex. [B11]; mp. 179° C.
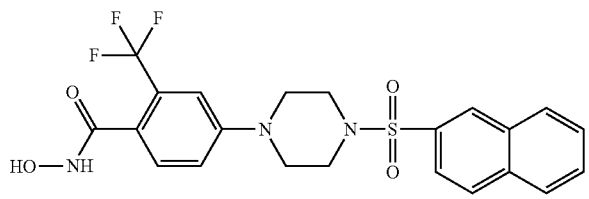
Co. No. 11; Ex. [B12]; mp. 196° C.
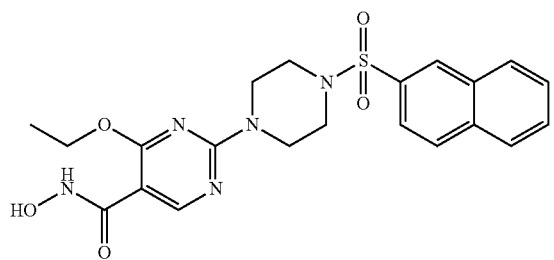
Co. No. 12; Ex. [B13]; mp. 197° C.
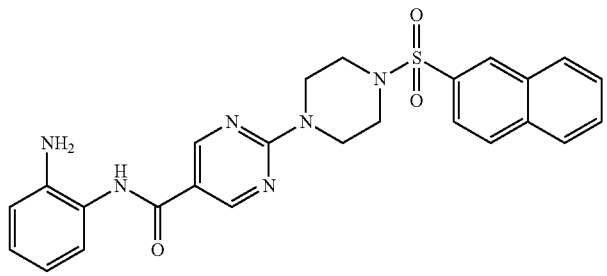
Co. No. 13; Ex. [B14]; mp. 238° C.

TABLE F-1-continued
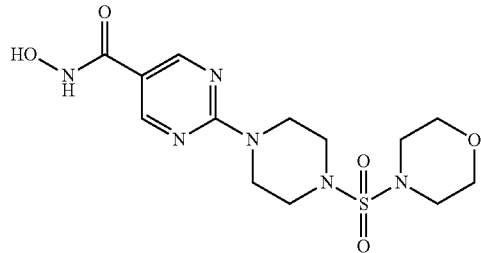
Co. No. 14; Ex. [B15]; MH⁺ = 373
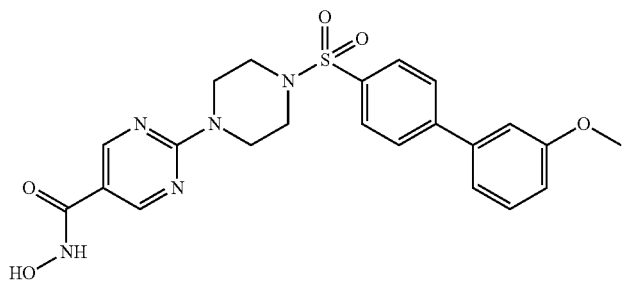
Co. No. 15; Ex. [B16]
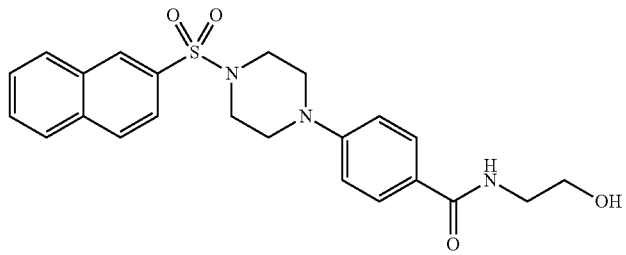
Co. No. 16; Ex. [B1]
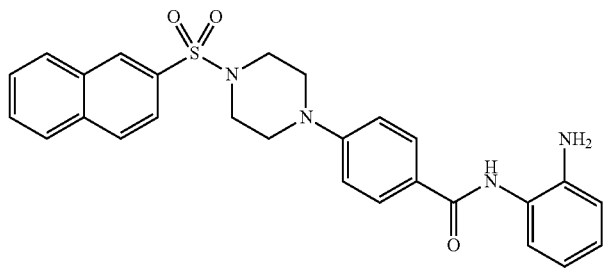
Co. No. 17; Ex. [B1]
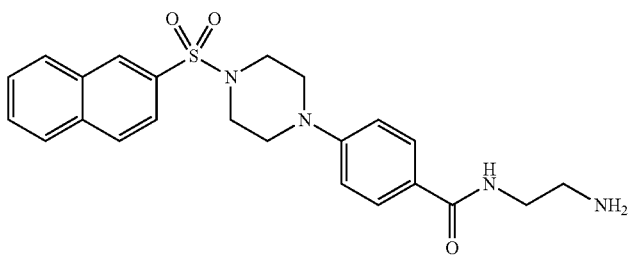
C₂HF₃O₂ (1:1), Co. No. 18; Ex. [B1]

TABLE F-1-continued
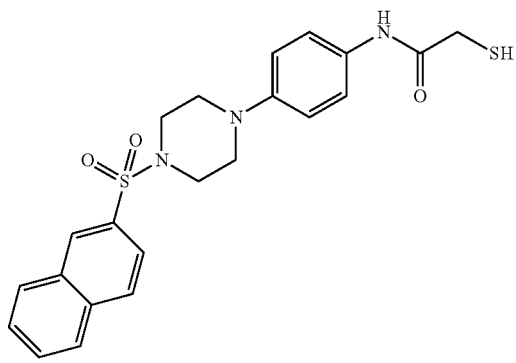
•C₂HF₃O₂ (1:1), Co. No. 19; Ex. [B1]
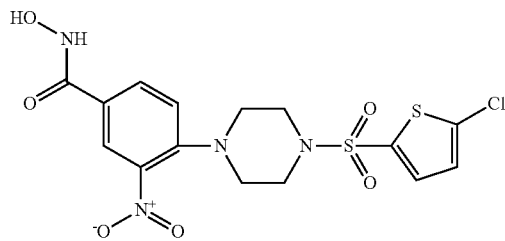
•C₂HF₃O₂ (1:1), Co. No. 20; Ex. [B1]; ms. 447
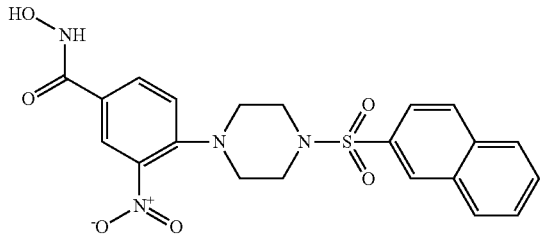
•C₂HF₃O₂ (1:1), Co. No. 21; Ex. [B1]; ms. 457
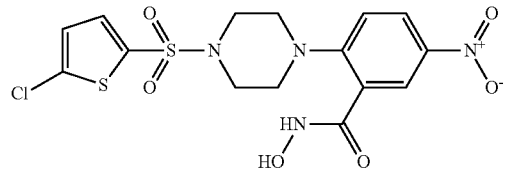
•C₂HF₃O₂ (1:1), Co. No. 22; Ex. [B1]; ms. 447
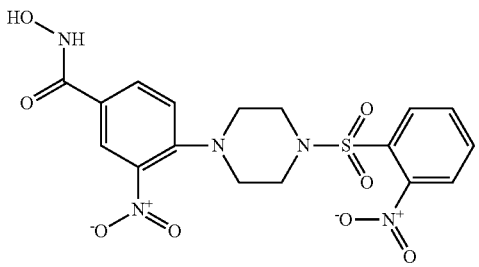
•C₂HF₃O₂ (1:1), Co. No. 23; Ex. [B1]; ms. 452

TABLE F-1-continued
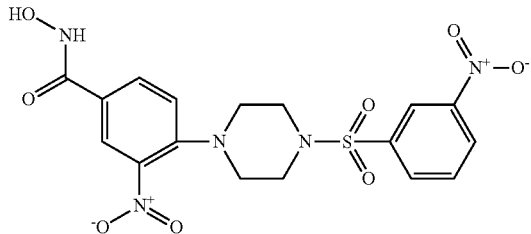
·C$_2$HF$_3$O$_2$ (1:1), Co. No. 24; Ex. [B1];
ms. 452
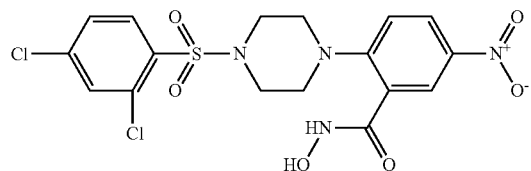
·C$_2$HF$_3$O$_2$ (1:1), Co. No. 25; Ex. [B1];
ms. 477
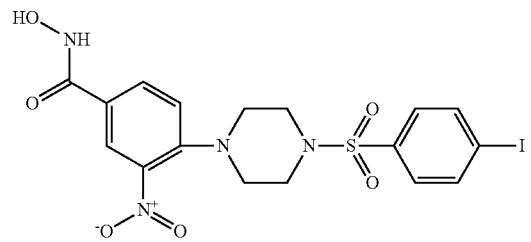
·C$_2$HF$_3$O$_2$ (1:1), Co. No. 26; Ex. [B1];
ms. 533
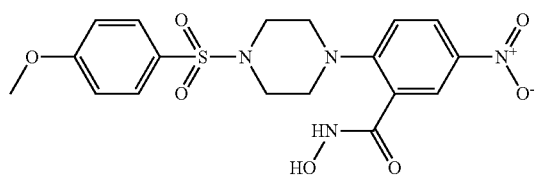
·C$_2$HF$_3$O$_2$ (1:1), Co. No. 27; Ex. [B1];
ms. 437
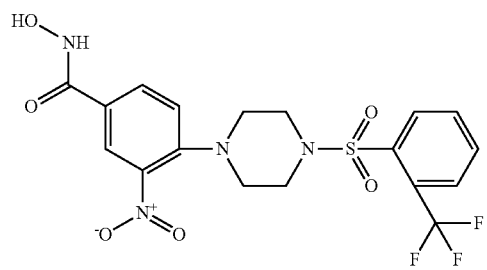
·C$_2$HF$_3$O$_2$ (1:1), Co. No. 28; Ex. [B1];
ms. 475

TABLE F-1-continued
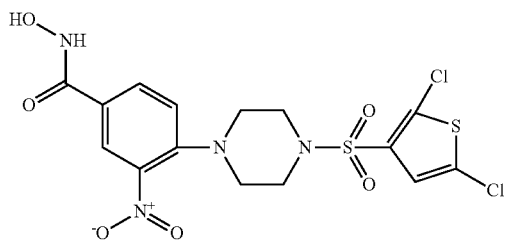
•C₂HF₃O₂ (1:1), Co. No. 29; Ex. [B1];
ms. 482
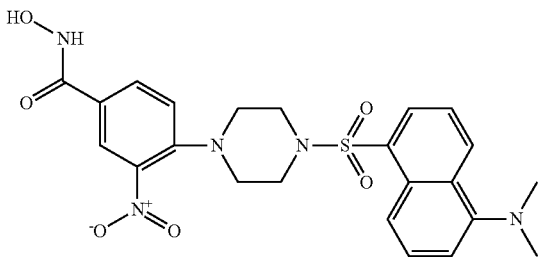
•C₂HF₃O₂ (1:1), Co. No. 30; Ex. [B1];
ms. 500
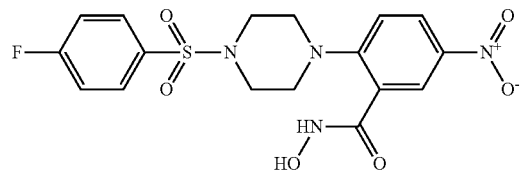
•C₂HF₃O₂ (1:1), Co. No. 31; Ex. [B1];
ms. 425
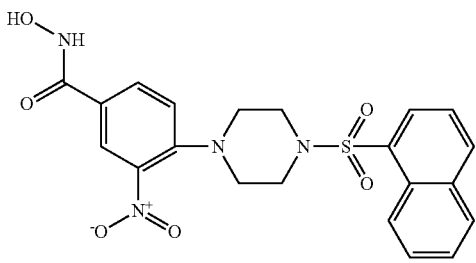
•C₂HF₃O₂ (1:1), Co. No. 32; Ex. [B1];
ms. 457
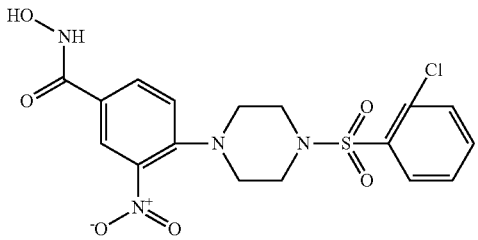
•C₂HF₃O₂ (1:1), Co. No. 33; Ex. [B1];
ms. 441

TABLE F-1-continued
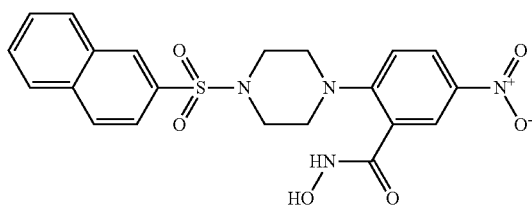
·C$_2$HF$_3$O$_2$ (1:1), Co. No. 34; Ex. [B1];
ms. 457
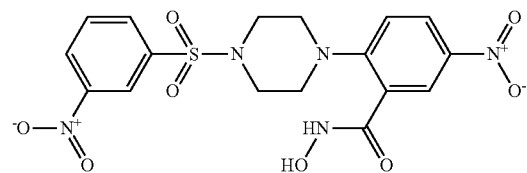
·C$_2$HF$_3$O$_2$ (1:1), Co. No. 35; Ex. [B1];
ms. 452
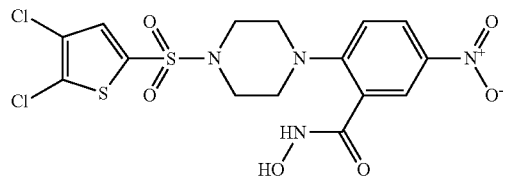
·C$_2$HF$_3$O$_2$ (1:1), Co. No. 36; Ex. [B1];
ms. 483
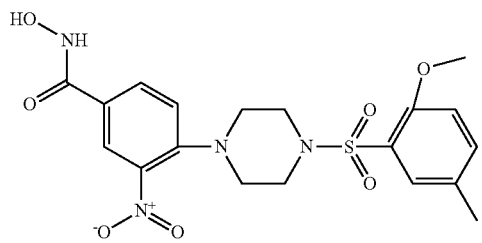
·C$_2$HF$_3$O$_2$ (1:1), Co. No. 37; Ex. [B1];
ms. 451
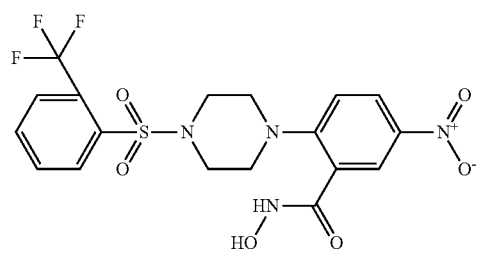
·C$_2$HF$_3$O$_2$ (1:1), Co. No. 38; Ex. [B1];
ms. 475

TABLE F-1-continued
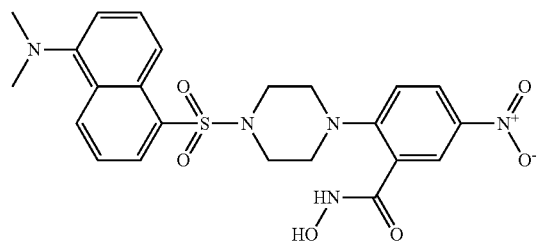
•C₂HF₃O₂ (1:1), Co. No. 39; Ex. [B1];
ms. 500
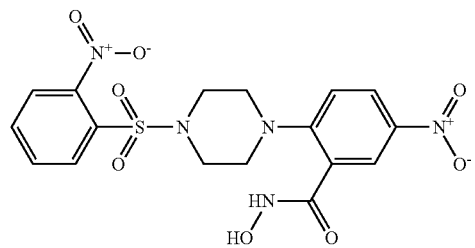
•C₂HF₃O₂ (1:1), Co. No. 40; Ex. [B1];
ms. 452
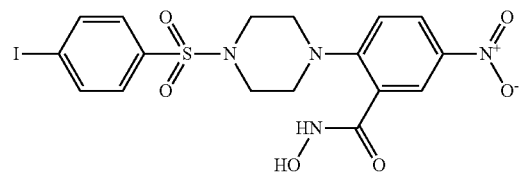
•C₂HF₃O₂ (1:1), Co. No. 41; Ex. [B1];
ms. 533
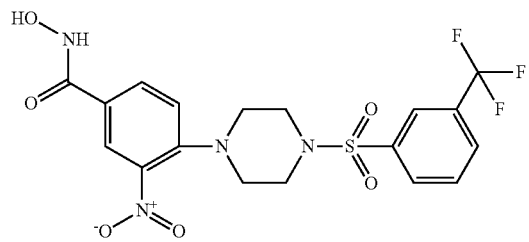
•C₂HF₃O₂ (1:1), Co. No. 42; Ex. [B1];
ms. 475
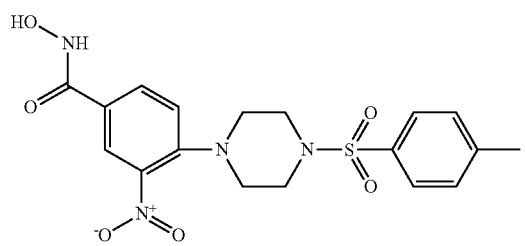
•C₂HF₃O₂ (1:1), Co. No. 43; Ex. [B1];
ms. 421

TABLE F-1-continued
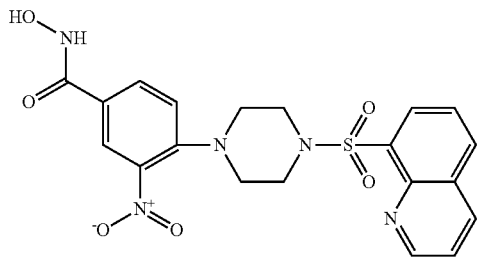
•C₂HF₃O₂ (1:1), Co. No. 44; Ex. [B1];
ms. 458
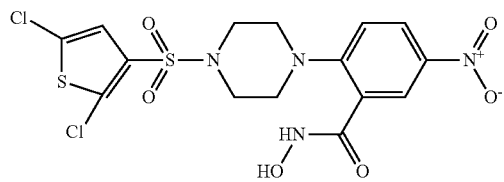
•C₂HF₃O₂ (1:1), Co. No. 45; Ex. [B1];
ms. 481
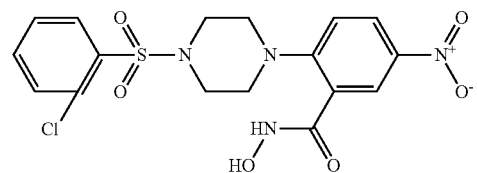
•C₂HF₃O₂ (1:1), Co. No. 46; Ex. [B1];
ms. 441
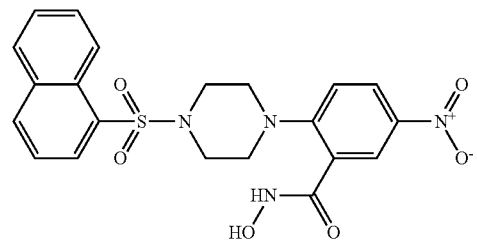
•C₂HF₃O₂ (1:1), Co. No. 47; Ex. [B1];
ms. 457
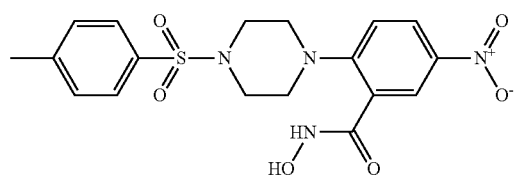
•C₂HF₃O₂ (1:1), Co. No. 48; Ex. [B1];
ms. 421

TABLE F-1-continued
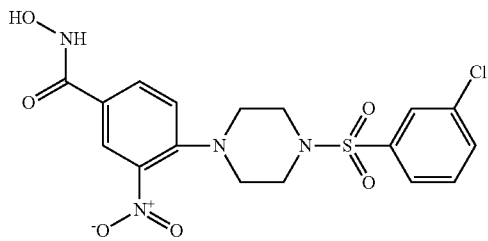
·C₂HF₃O₂ (1:1), Co. No. 49; Ex. [B1];
ms. 441
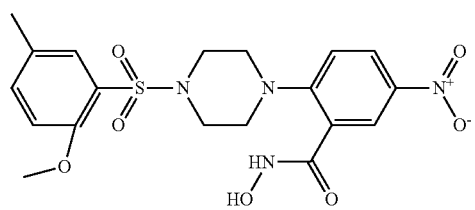
·C₂HF₃O₂ (1:1), Co. No. 50; Ex. [B1];
ms. 451
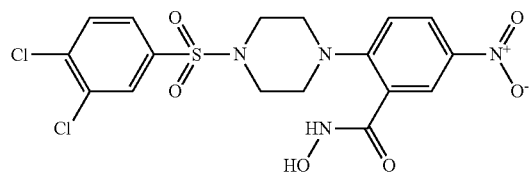
·C₂HF₃O₂ (1:1), Co. No. 51; Ex. [B1];
ms. 477
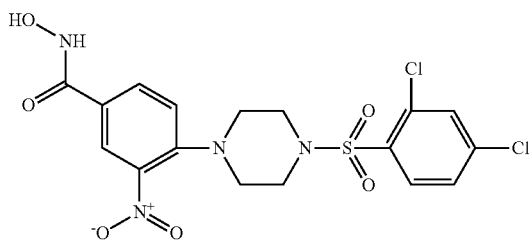
·C₂HF₃O₂ (1:1), Co. No. 52; Ex. [B1];
ms. 475
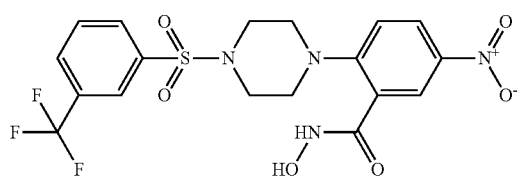
·C₂HF₃O₂ (1:1), Co. No. 53; Ex. [B1];
ms. 475

TABLE F-1-continued
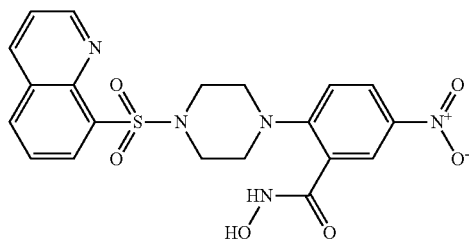
•C₂HF₃O₂ (1:1), Co. No. 54; Ex. [B1];
ms. 458
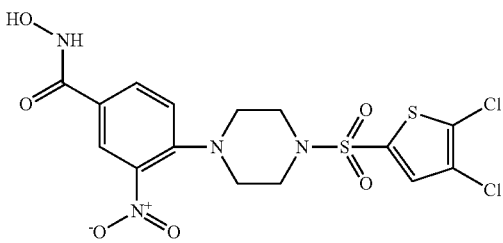
•C₂HF₃O₂ (1:1), Co. No. 55; Ex. [B1];
ms. 481
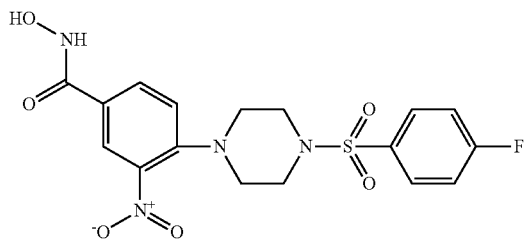
•C₂HF₃O₂ (1:1), Co. No. 56; Ex. [B1];
ms. 425
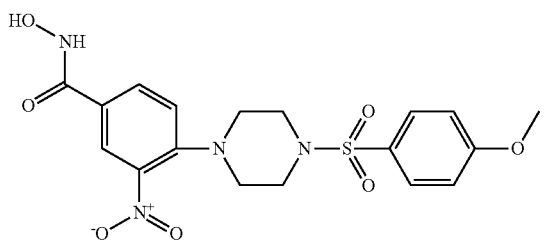
•C₂HF₃O₂ (1:1), Co. No. 57; Ex. [B1];
ms. 437
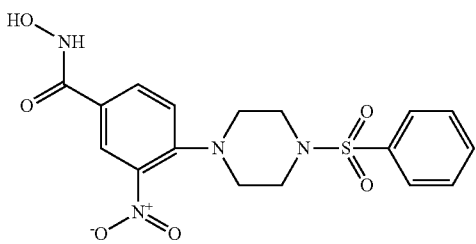
•C₂HF₃O₂ (1:1), Co. No. 58; Ex. [B1];
ms. 407

TABLE F-1-continued
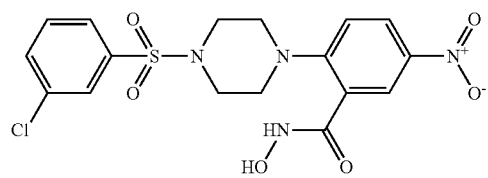
•C₂HF₃O₂ (1:1), Co. No. 59; Ex. [B1]; ms. 441
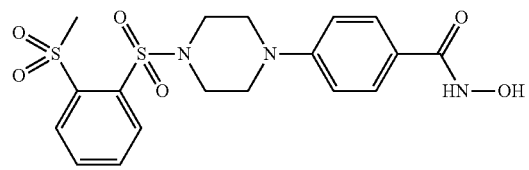
Co. No. 60; Ex. [B1]
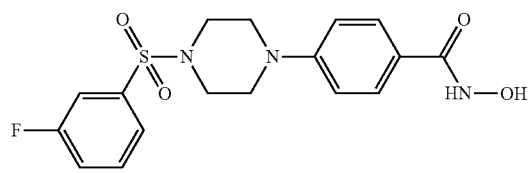
Co. No. 61; Ex. [B1]; mp. 228° C.
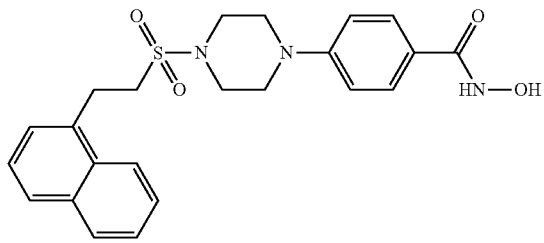
Co. No. 62; Ex. [B1]
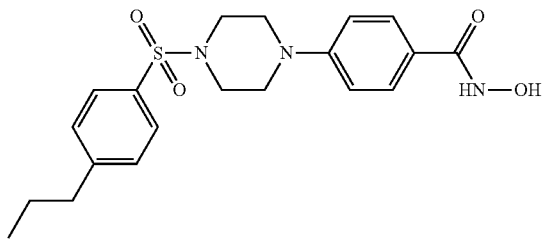
Co. No. 63; Ex. [B1]; mp. 230° C.
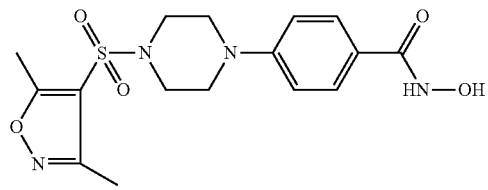
Co. No. 64; Ex. [B1]

TABLE F-1-continued
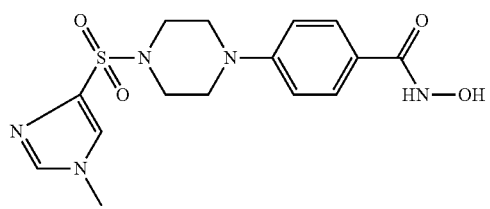
Co. No. 65; Ex. [B1]; mp. 252° C.
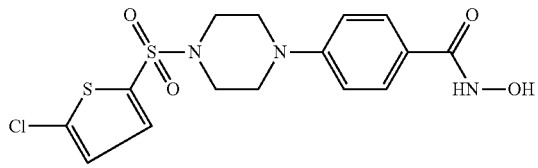
Co. No. 66; Ex. [B1]; mp. 231° C.
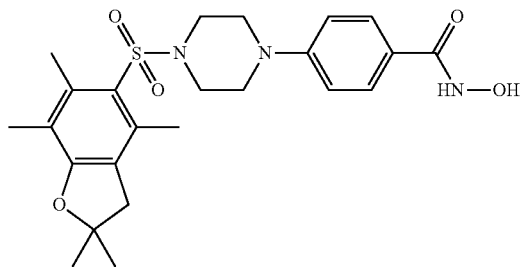
Co. No. 67; Ex. [B1]; mp. 226° C.
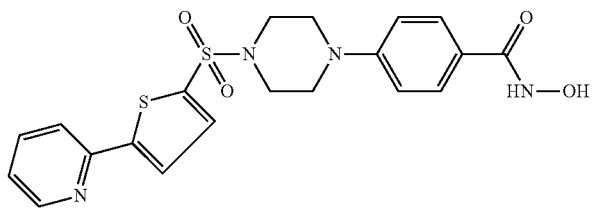
Co. No. 68; Ex. [B1]
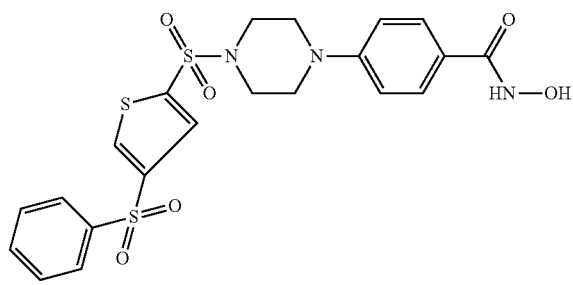
Co. No. 69; Ex. [B1]
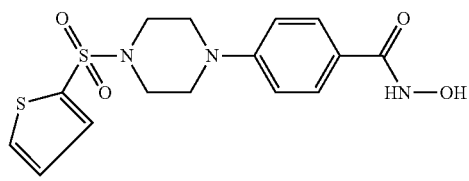
Co. No. 70; Ex. [B1]; mp. 228° C.

TABLE F-1-continued
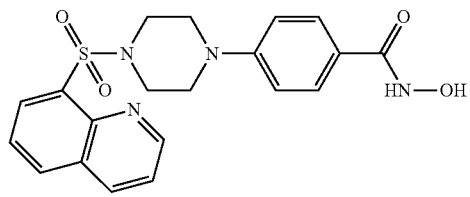
Co. No. 71; Ex. [B1]
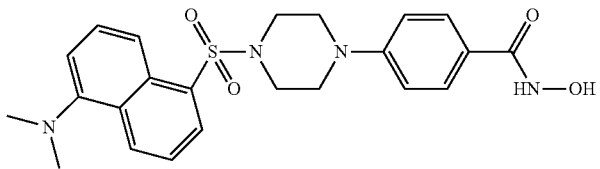
Co. No. 72; Ex. [B1]
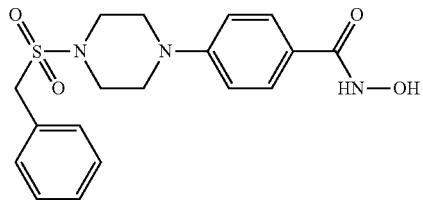
Co. No. 73; Ex. [B1]
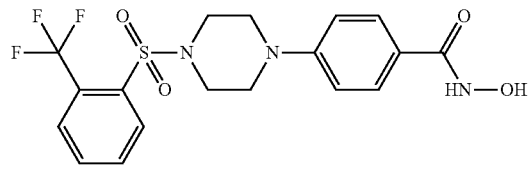
Co. No. 74; Ex. [B1]; mp. 234° C.
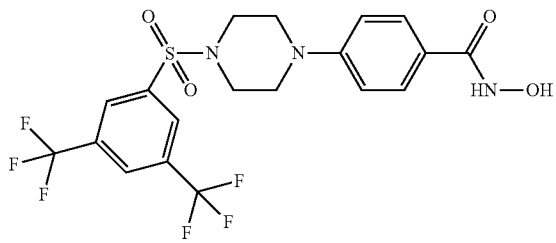
Co. No. 75; Ex. [B1]
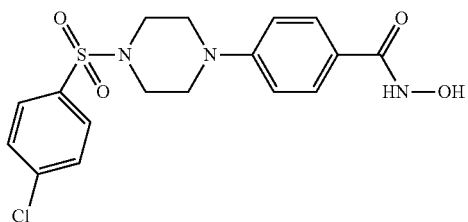
Co. No. 76; Ex. [B1]; mp. 224° C.

TABLE F-1-continued
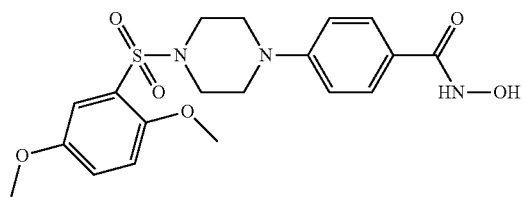
Co. No. 77; Ex. [B1]
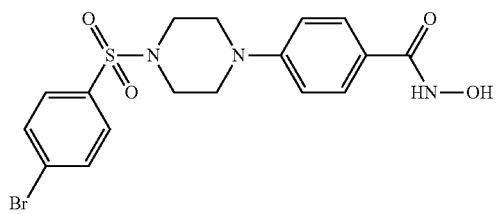
Co. No. 78; Ex. [B1]; mp. 221° C.
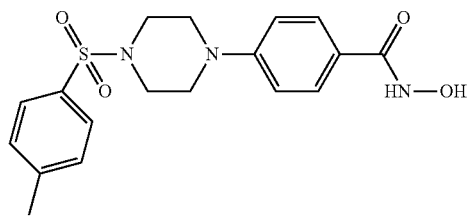
Co. No. 79; Ex. [B1]; mp. 219° C.
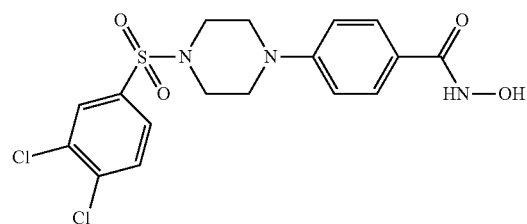
Co. No. 80; Ex. [B1]
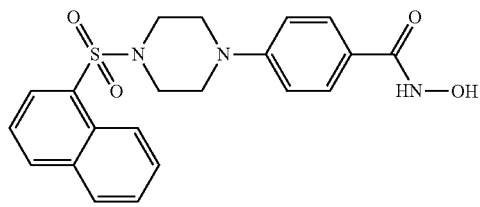
Co. No. 81; Ex. [B1]
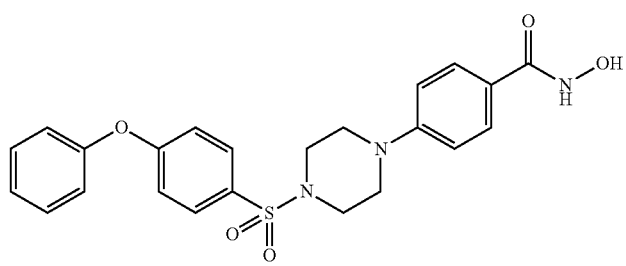
Co. No. 82; Ex. [B1]; mp. 222° C.

TABLE F-1-continued
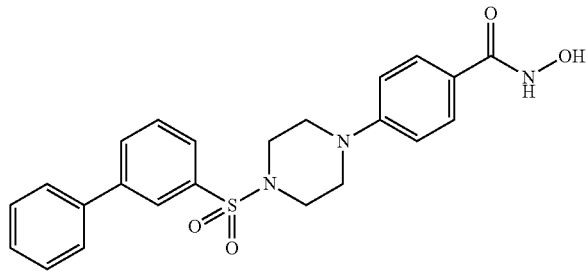
Co. No. 83; Ex. [B1]; mp. 214° C.
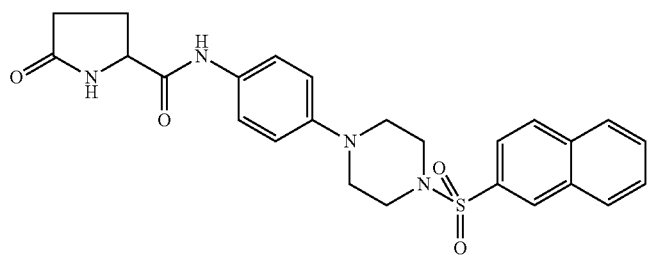
Co. No. 84; Ex. [B6]; mp. 232° C.
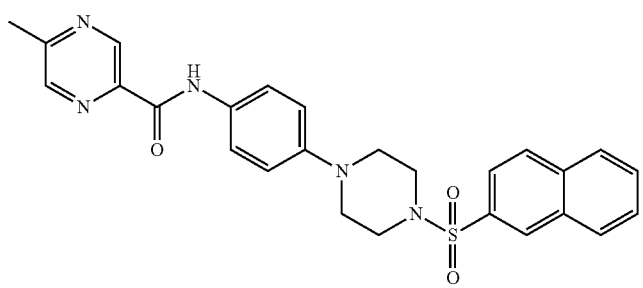
Co. No. 85; Ex. [B6]; mp. 250° C.
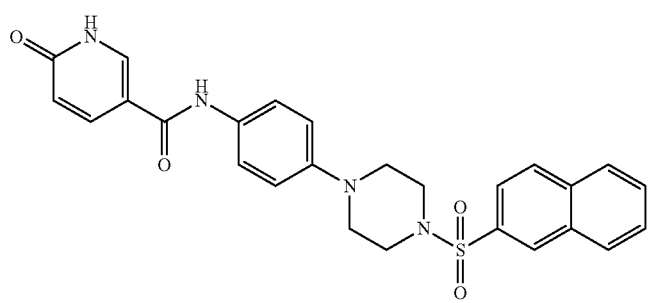
Co. No. 86; Ex. [B6]; mp. 264° C.
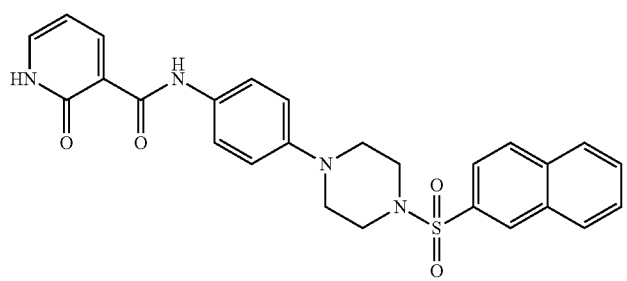
Co. No. 87; Ex. [B6]; mp. >260° C.

TABLE F-1-continued
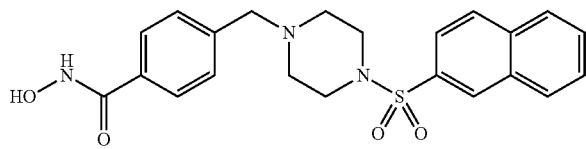
Co. No. 88; Ex. [B8]
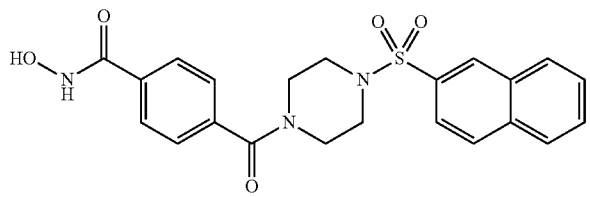
Co. No. 89; Ex. [B9]
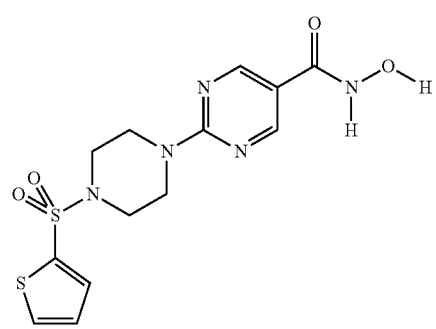
Co. No. 90; Ex. [B15]
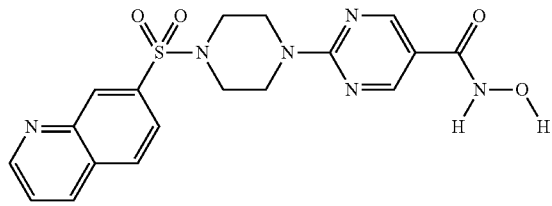
Co. No. 91; Ex. [B15]
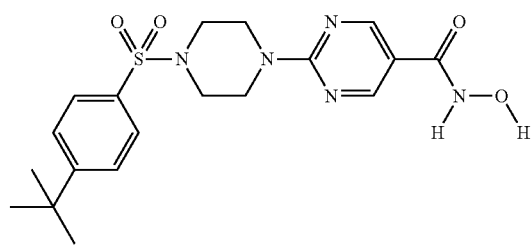
Co. No. 92; Ex. [B15]
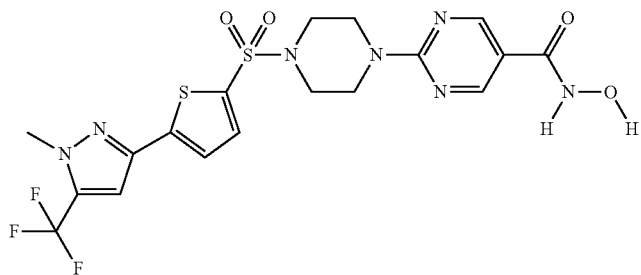
Co. No. 93; Ex. [B15]

TABLE F-1-continued
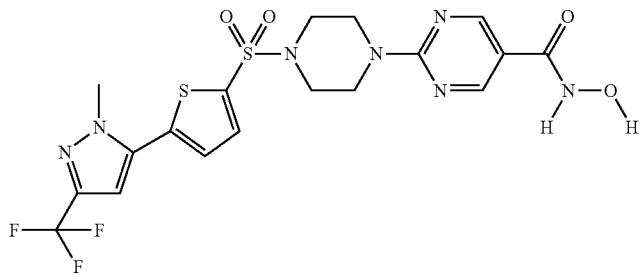
Co. No. 94; Ex. [B15]
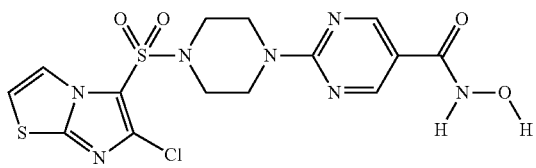
Co. No. 95; Ex. [B15]
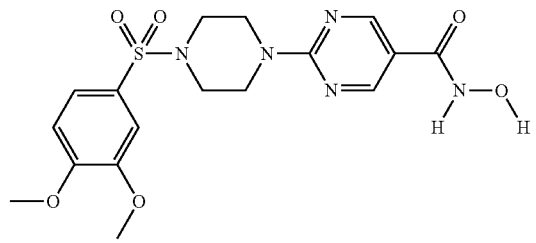
Co. No. 96; Ex. [B15]
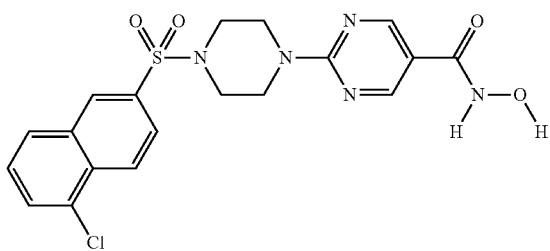
Co. No. 97; Ex. [B15]
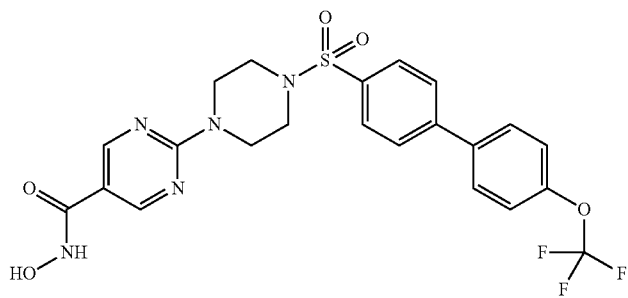
Co. No. 98; Ex. [B16]

TABLE F-1-continued
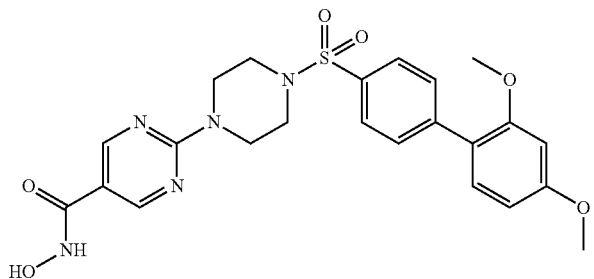
Co. No. 99; Ex. [B16]
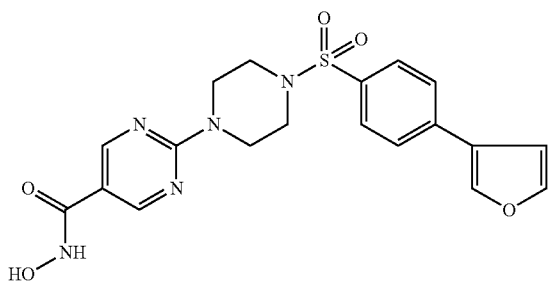
Co. No. 100; Ex. [B16]
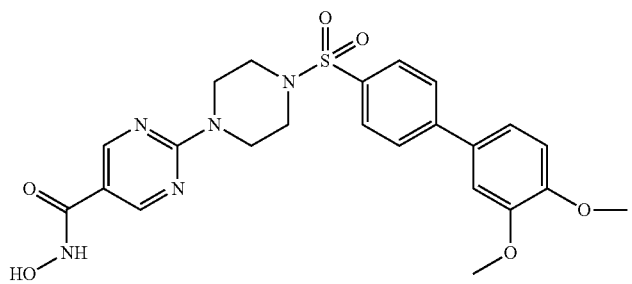
Co. No. 101; Ex. [B16]
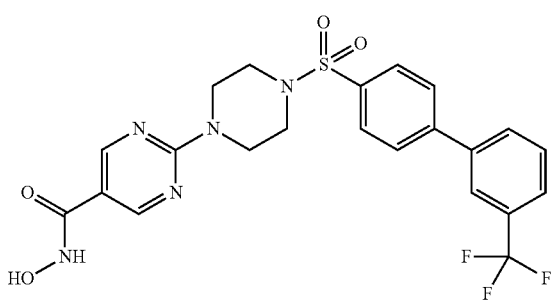
Co. No. 102; Ex. [B16]
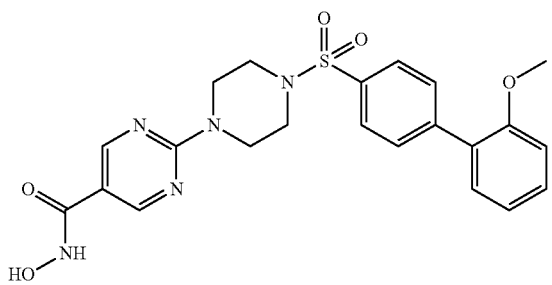
Co. No. 103; Ex. [B16]

TABLE F-1-continued
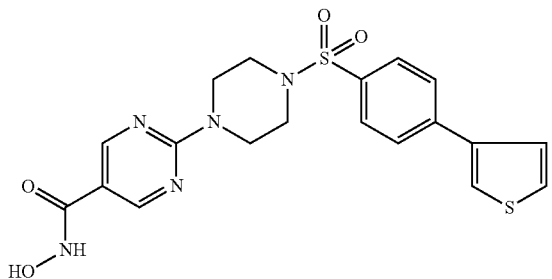
Co. No. 104; Ex. [B16]
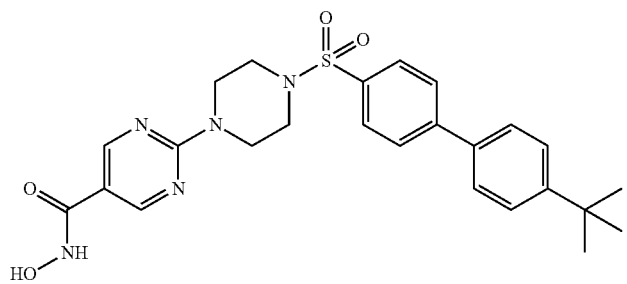
Co. No. 105; Ex. [B16]
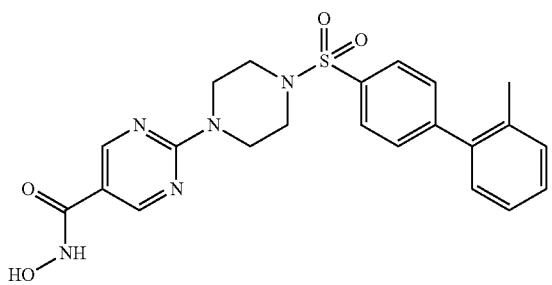
Co. No. 106; Ex. [B16]
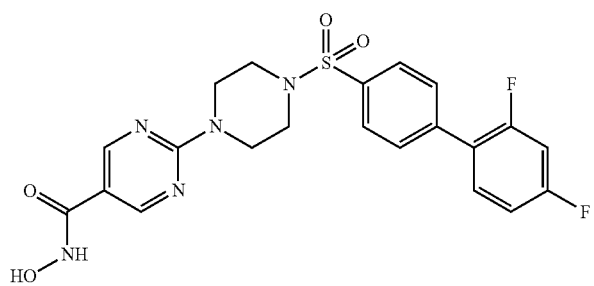
Co. No. 107; Ex. [B16]
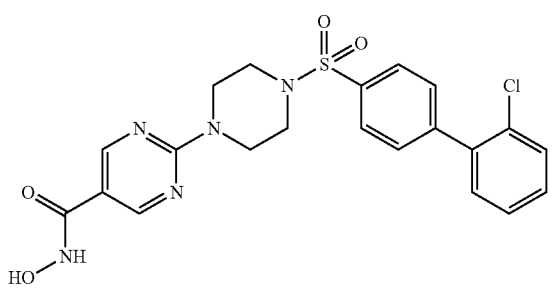
Co. No. 108; Ex. [B16]

TABLE F-1-continued
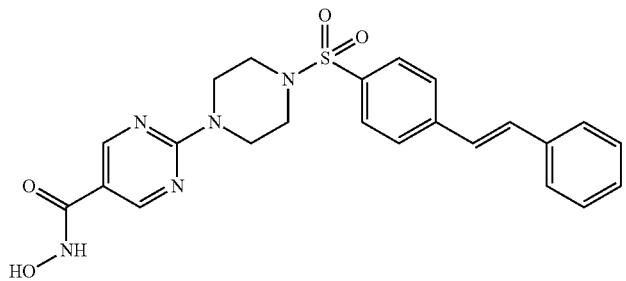
Co. No. 109; Ex. [B16]
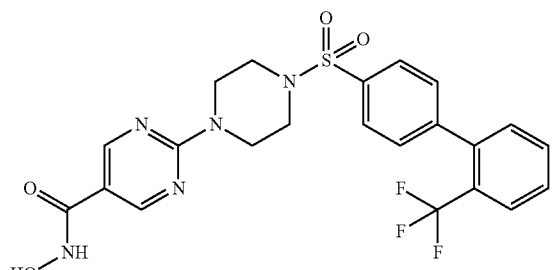
Co. No. 110; Ex. [B16]
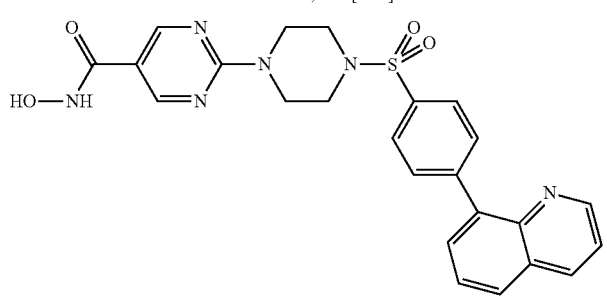
Co. No. 111; Ex. [B16]
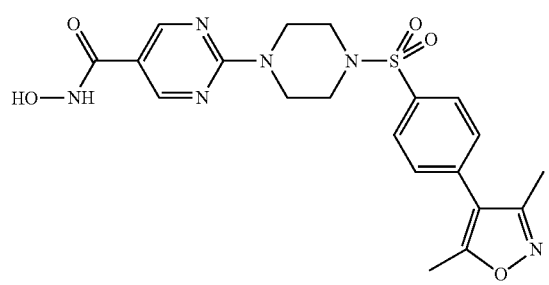
Co. No. 112; Ex. [B16]
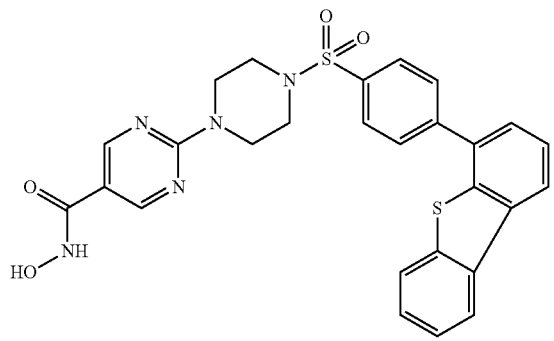
Co. No. 130; Ex. [B16]

TABLE F-1-continued
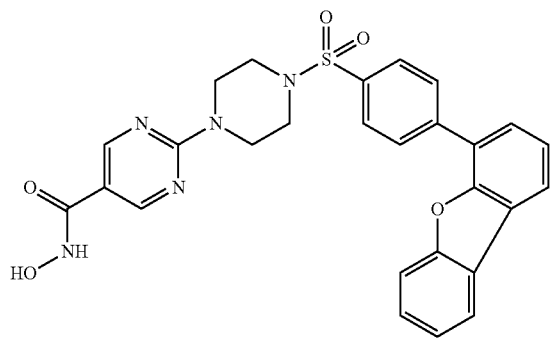
Co. No. 131; Ex. [B16]
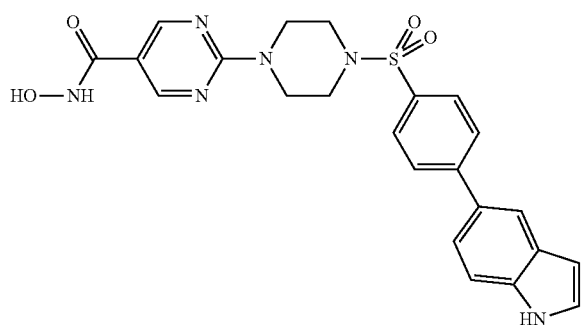
Co. No. 132; Ex. [B16]
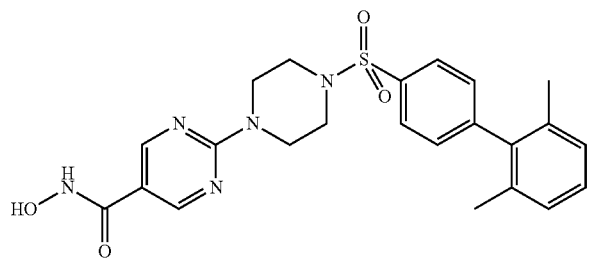
Co. No. 133; Ex. [B16]
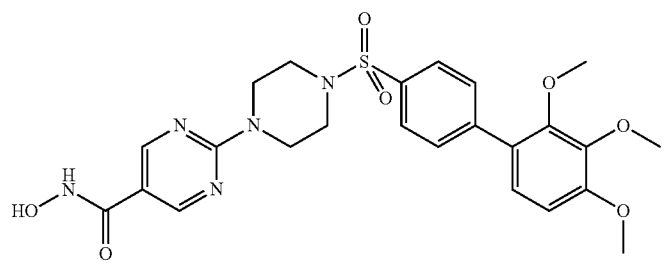
Co. No. 134; Ex. [B16]
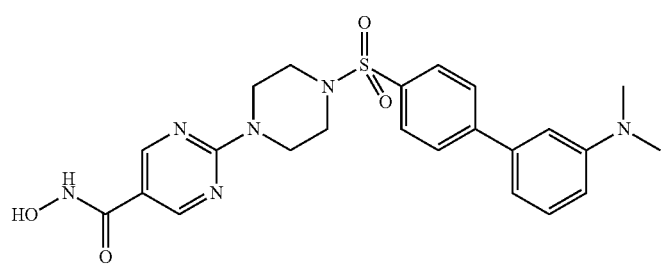
•C$_2$HF$_3$O$_2$; Co. No. 135; Ex. [B16]

TABLE F-1-continued
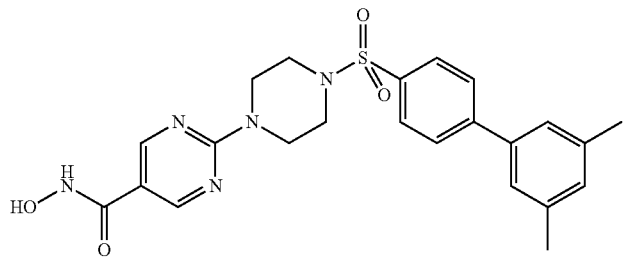
Co. No. 136; Ex. [B16]
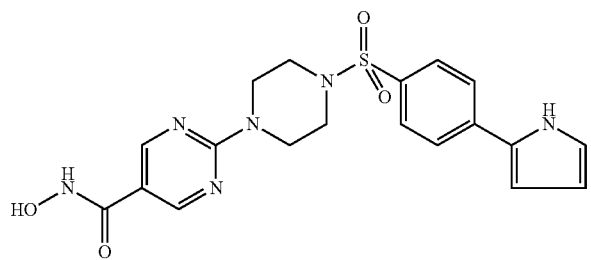
Co. No. 137; Ex. [B16]
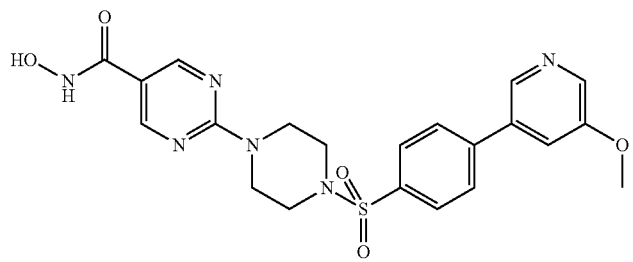
•1.6 $C_2HF_3O_2$; Co. No. 138; Ex. [B16]
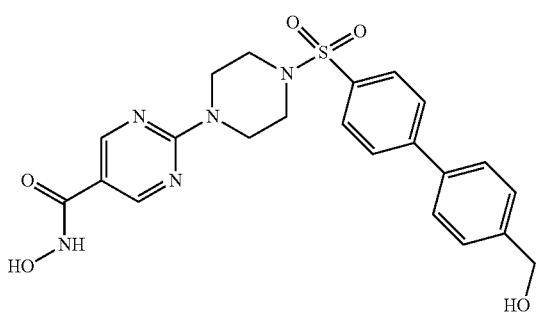
Co. No. 139; Ex. [B16]
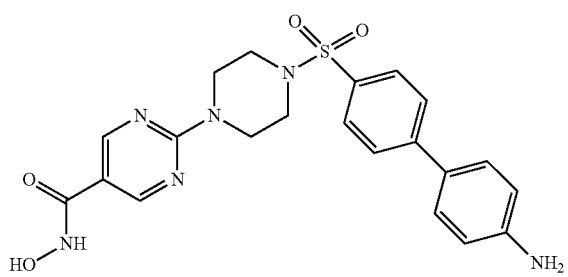
•1.5 $C_2F_3O_2$; Co. No. 140; Ex. [B16]

TABLE F-1-continued
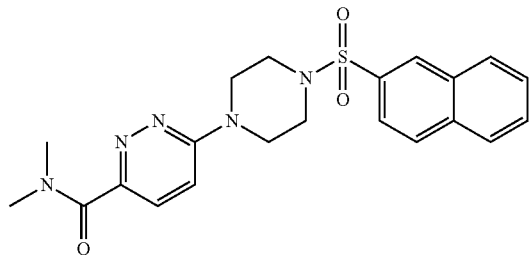
Co. No. 113; Ex. [B17]; mp. 200° C.
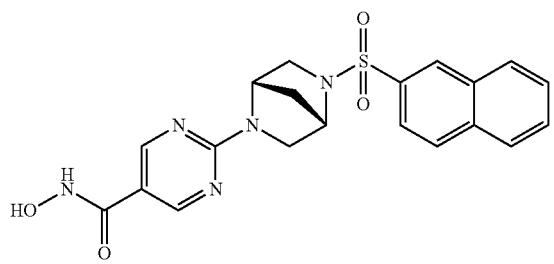
(S,S); Co. No. 114; Ex. [B18]; mp. 225° C.
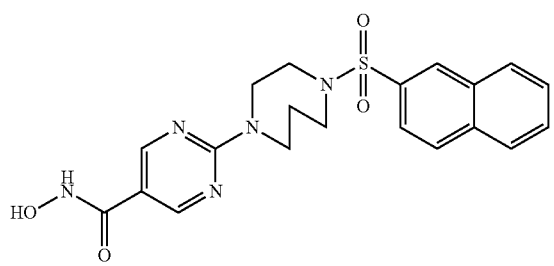
Co. No. 141; Ex. [B18]; mp. 240° C.
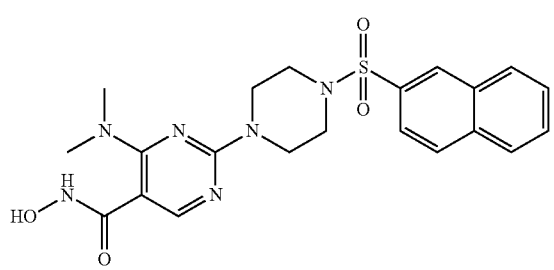
•C₂HF₃O₂; Co. No. 115; Ex. [B19]; mp. 135° C.
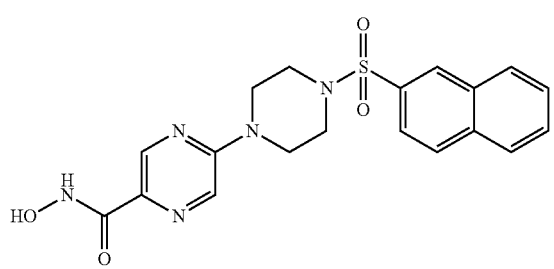
Co. No. 116; Ex. [B20]; mp. 249° C.

TABLE F-1-continued
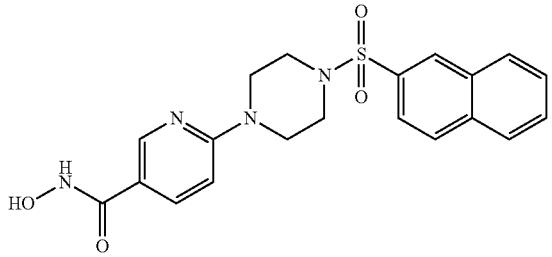
Co. No. 142; Ex. [B20]; mp. 183° C.
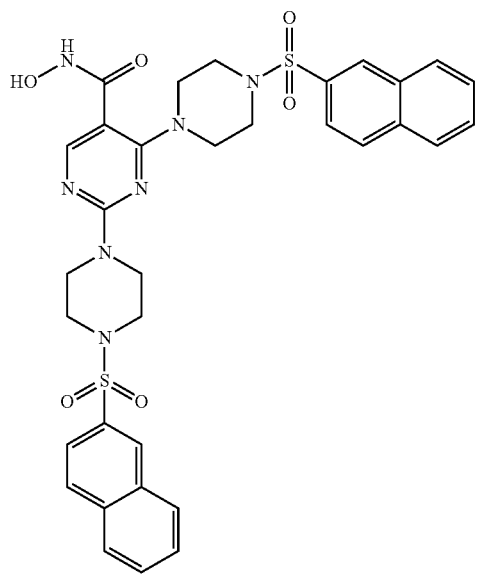
·2 $C_2HF_3O_2$; Co. No. 117; Ex. [B21]; mp. 80° C.
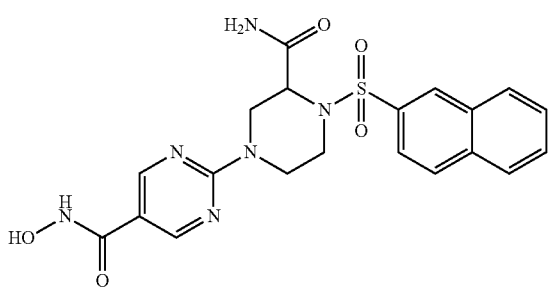
Co. No. 118; Ex. [B22]; mp. 210° C.
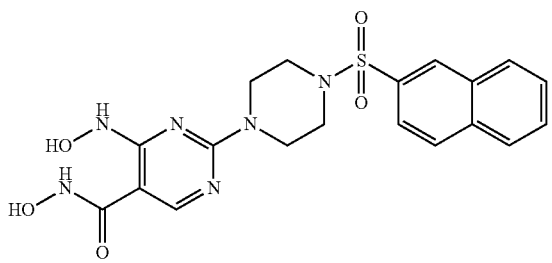
Co. No. 119; Ex. [B23]; mp. 225° C.

TABLE F-1-continued
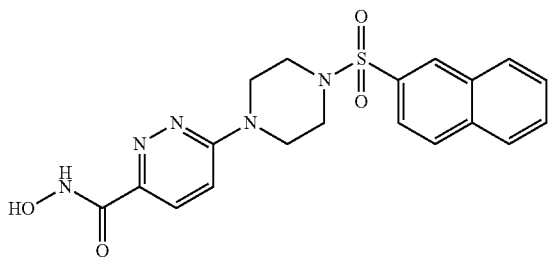
Co. No. 120; Ex. [B24]; mp. >260° C.
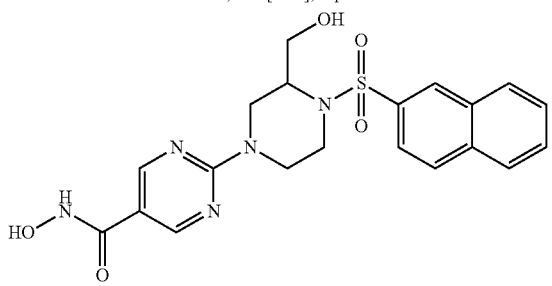
Co. No. 121; Ex. [B25]; mp. 220° C.
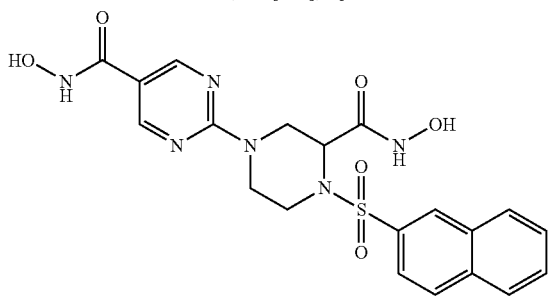
Co. No. 122; Ex. [B26]; mp. 166° C.
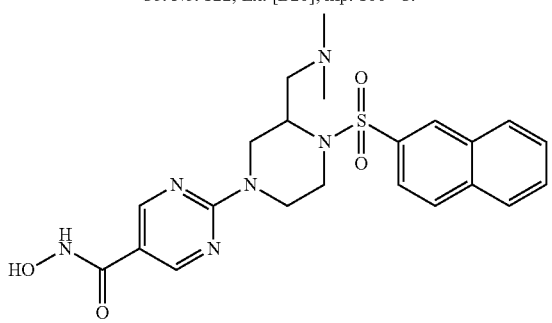
•$C_2HF_3O_2$; Co. No. 123; Ex. [B27]; mp. 114° C.
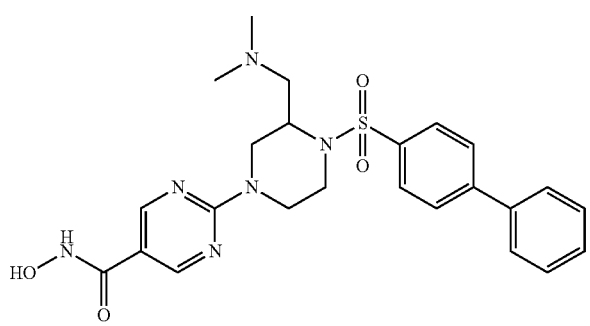
•0.82 $C_2HF_3O_2$; Co. No. 143; Ex. [B27]; mp. 153° C.

TABLE F-1-continued
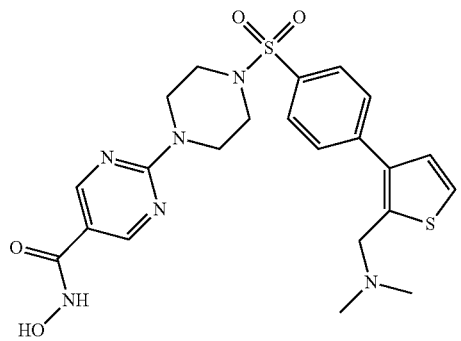
•C₂HF₃O₂; Co. No. 124; Ex. [B28]; mp. 192° C.
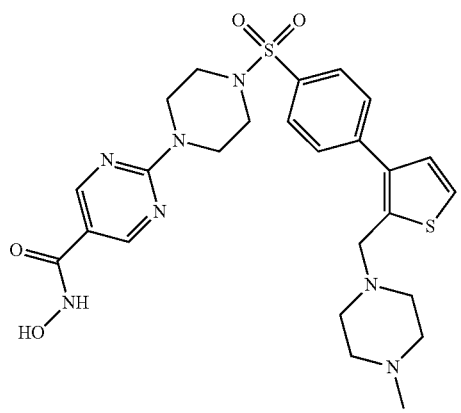
•0.65 H₂O•C₂HF₃O₂; Co. No. 144; Ex. [B28]; mp. 145° C.
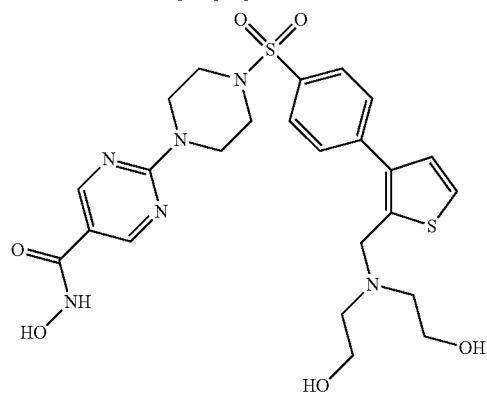
•C₂HF₃O₂; Co. No. 145; Ex. [B28]
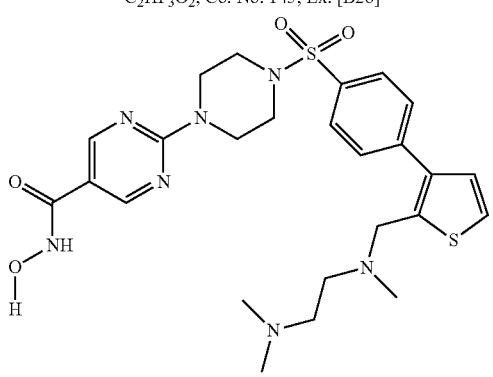
•H₂O •C₂HF₃O₂; Co. No. 146; Ex. [B28]

TABLE F-1-continued
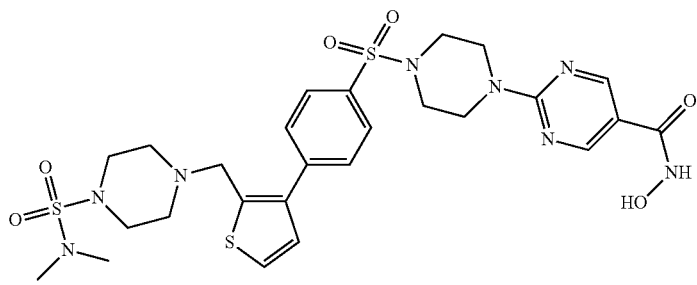
•C₂HF₃O₂; Co. No. 147; Ex. [B28]; mp. 214.2° C.
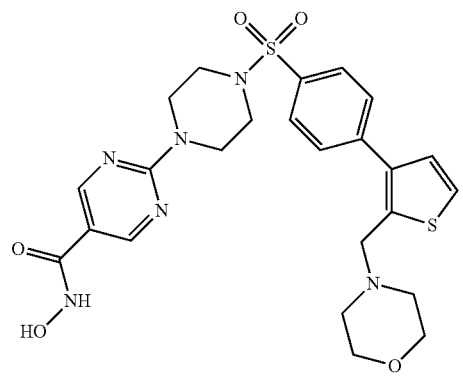
•H₂O•C₂HF₃O₂; Co. No. 148; Ex. [B28]; mp. 196.3° C.
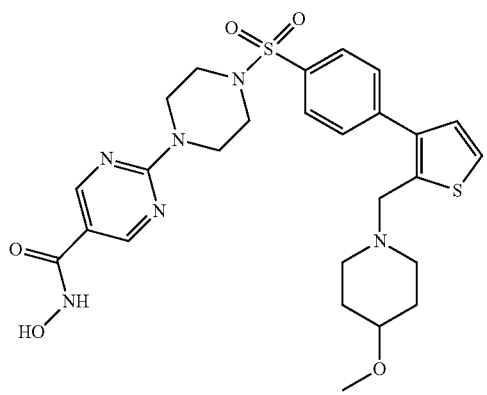
•C₂HF₃O₂; Co. No. 149; Ex. [B28]; mp. 205° C.

TABLE F-1-continued
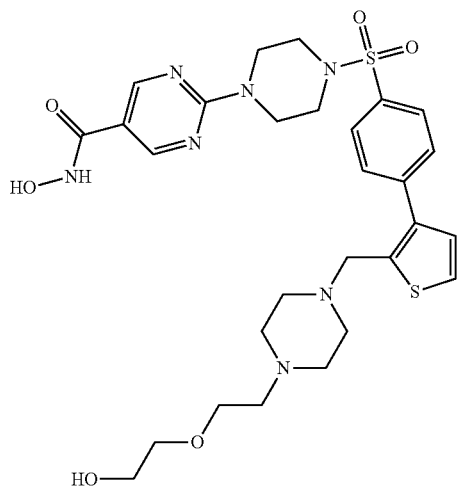
•C₂HF₃O₂; Co. No. 150; Ex. [B28]; mp. 202.4° C.
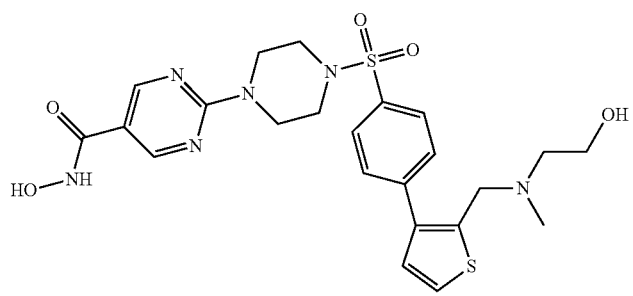
•C₂HF₃O₂; Co. No. 151; Ex. [B28]; mp. 200° C.
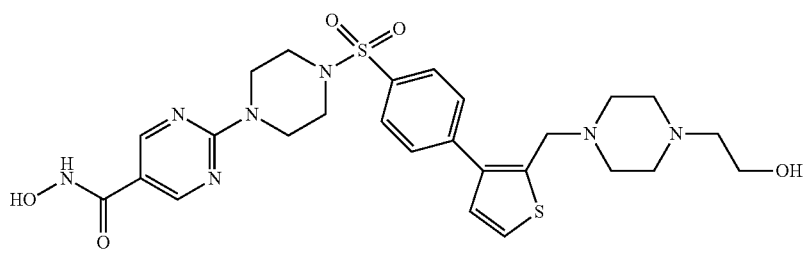
•C₂HF₃O₂; Co. No. 152; Ex. [B28]; mp. 234° C.
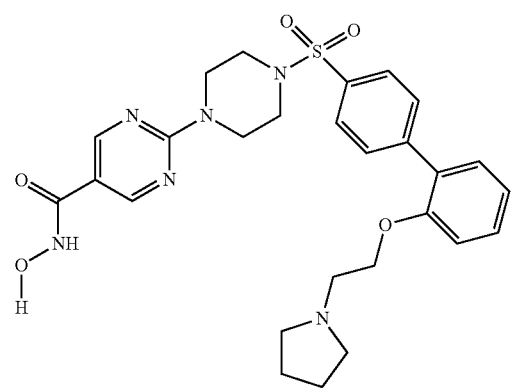
0.2 H₂O•C₂HF₃O₂; Co. No. 125; Ex. [B29]; mp. 146.9° C.

TABLE F-1-continued
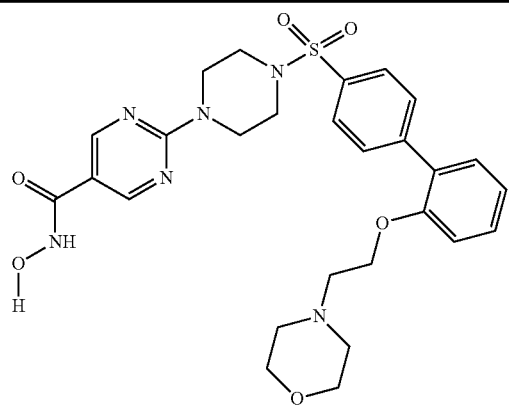
•C₂HF₃O₂; Co. No. 153; Ex. [B29]
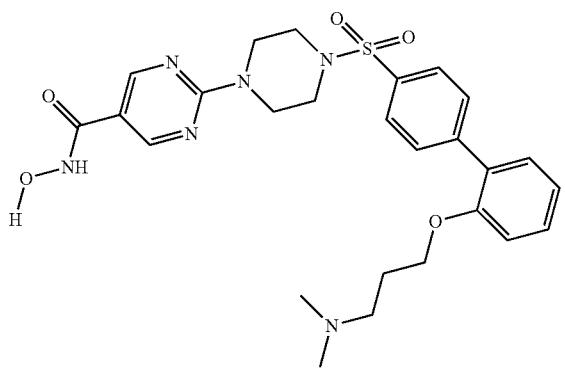
•0.6 H₂O•C₂HF₃O₂; Co. No. 154; Ex. [B29]; mp. 151° C.
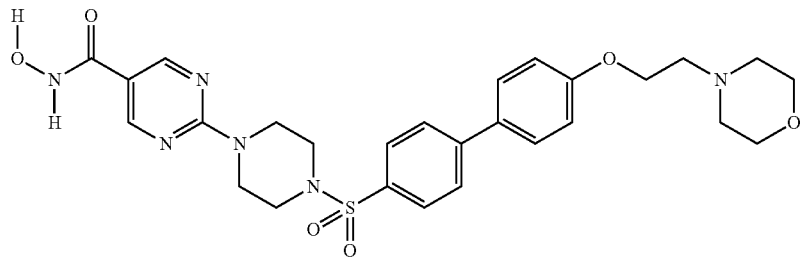
•C₂HF₃O₂; Co. No. 155; Ex. [B29]; mp. 40° C.
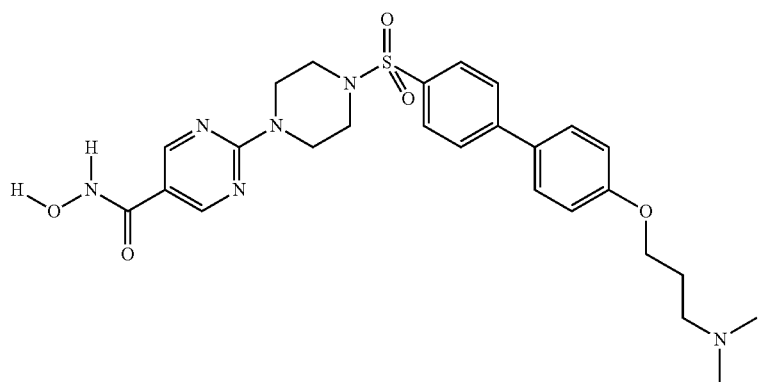
•0.3 H₂O •1.2 C₂HF₃O₂; Co. No. 156; Ex. [B29]; mp. 240° C.

TABLE F-1-continued
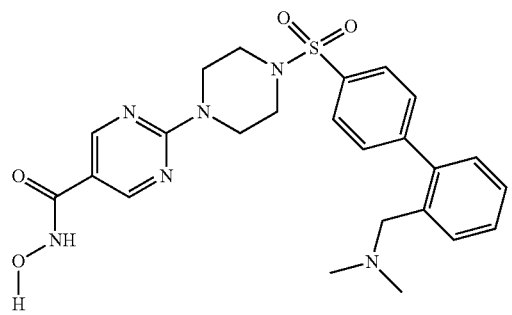
•C₂HF₃O₂; Co. No. 126; Ex. [B30]; mp. 190.7
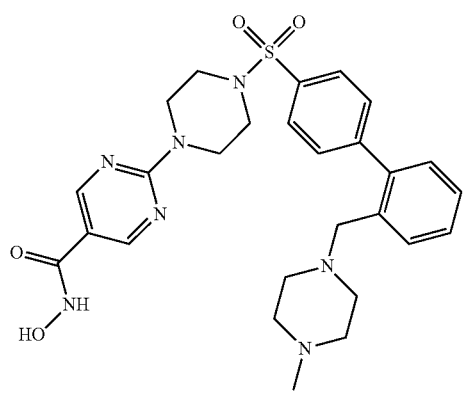
•0.5 H₂O •1.2 C₂HF₃O₂; Co. No. 157; Ex. [B30]; mp. 155° C.
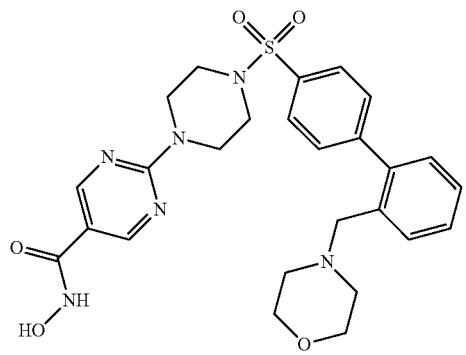
•C₂HF₃O₂; Co. No. 158; Ex. [B28]; mp. 165° C.
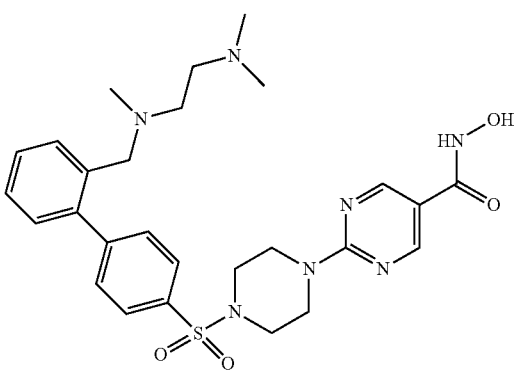
0.3 H₂O •1.5 C₂HF₃O₂; Co. No. 159; Ex. [B30]; mp. 163° C.

TABLE F-1-continued
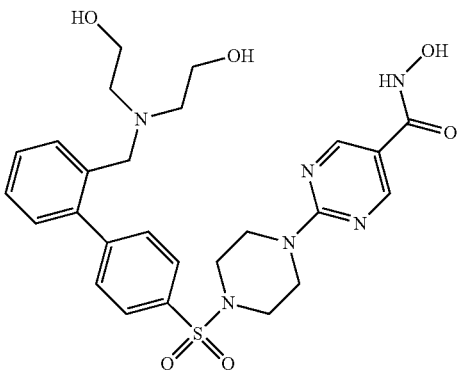
•$C_2HF_3O_2$; Co. No. 160; Ex. [B30]; mp. 182° C.
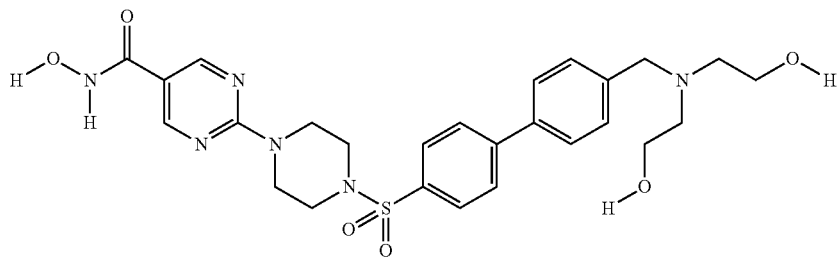
•$C_2HF_3O_2$; Co. No. 161; Ex. [B30]; mp. >260° C.
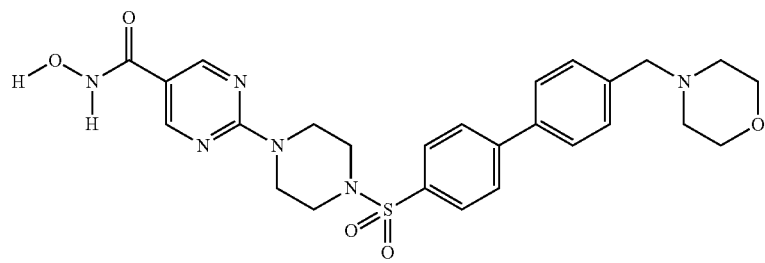
•$C_2HF_3O_2$; Co. No. 162; Ex. [B30]; mp. 164° C.
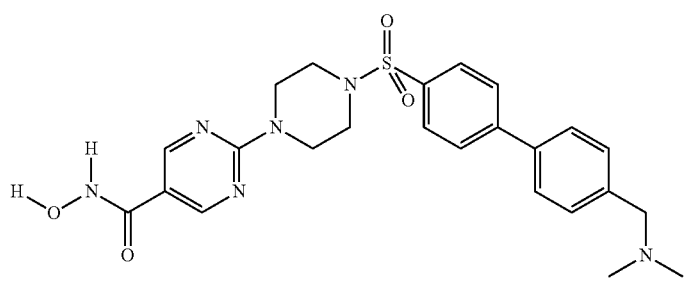
•0.6 $H_2O$ •$C_2HF_3O_2$; Co. No. 163; Ex. [B30]

TABLE F-1-continued
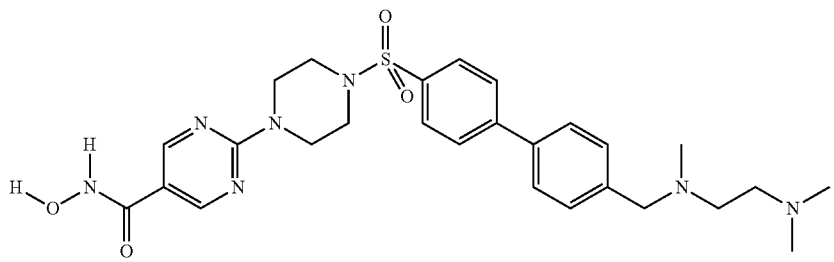
•0.7 H$_2$O•1.5•C$_2$HF$_3$O$_2$; Co. No. 164; Ex. [B30]; mp. 139° C.
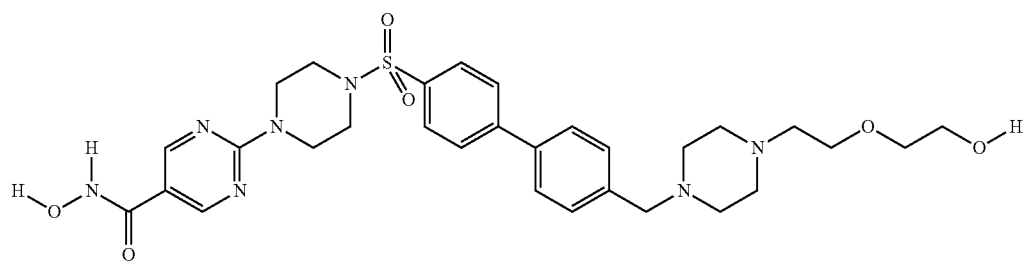
•C$_2$HF$_3$O$_2$; Co. No. 165; Ex. [B30]; mp. 197° C.
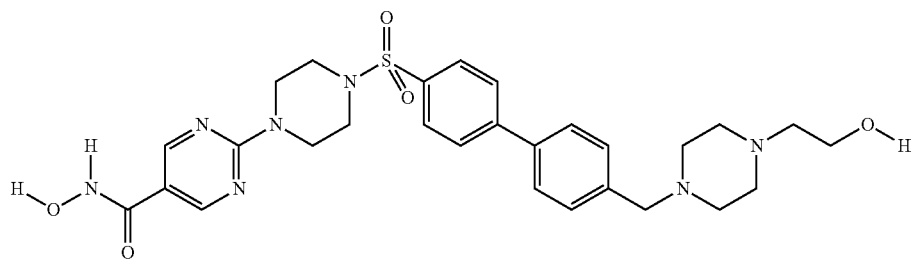
•C$_2$HF$_3$O$_2$; Co. No. 166; Ex. [B30]; mp. 183° C.
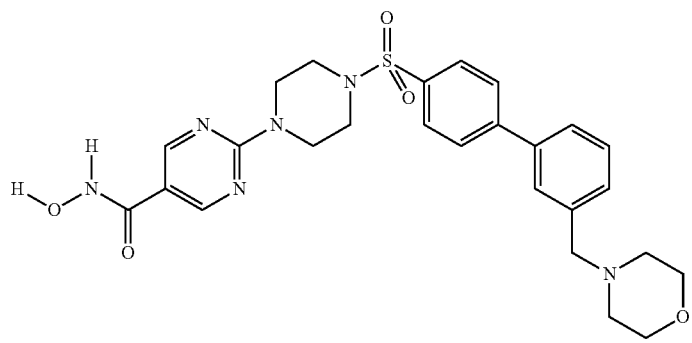
•C$_2$HF$_3$O$_2$; Co. No. 167; Ex. [B30]

TABLE F-1-continued
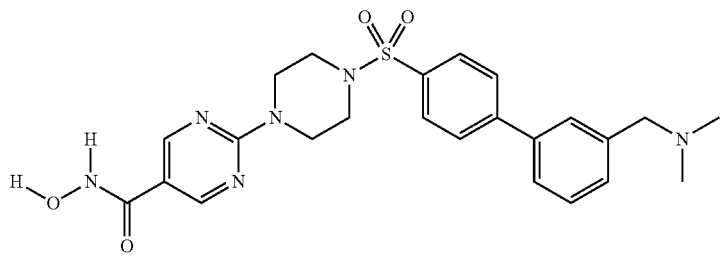
•C₂HF₃O₂; Co. No. 168; Ex. [B30]
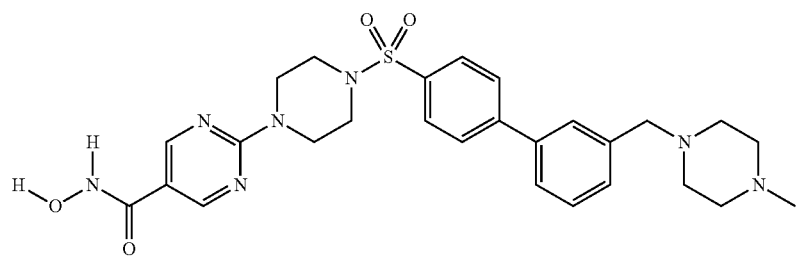
•1.1 C₂HF₃O₂; Co. No. 169; Ex. [B30]; mp. 184° C.
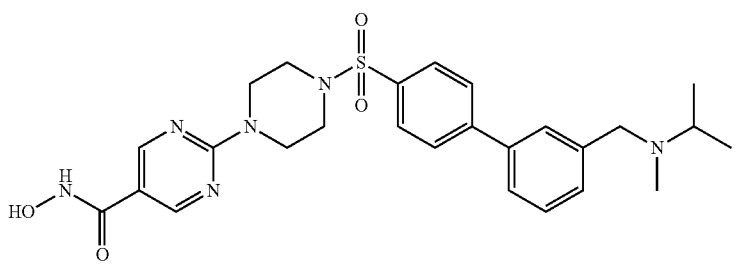
•0.94 C₂HF₃O₂; Co. No. 170; Ex. [B30]; mp. 130° C.
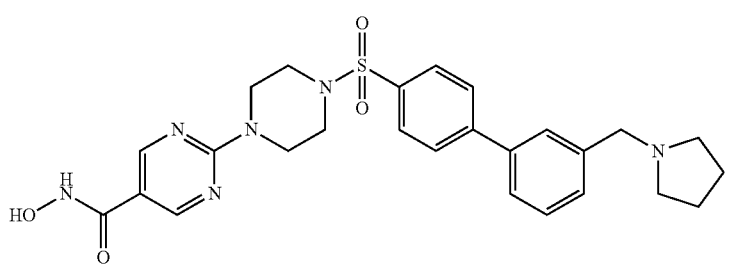
•1.03 C₂HF₃O₂; Co. No. 171; Ex. [B30]; mp. 205° C.
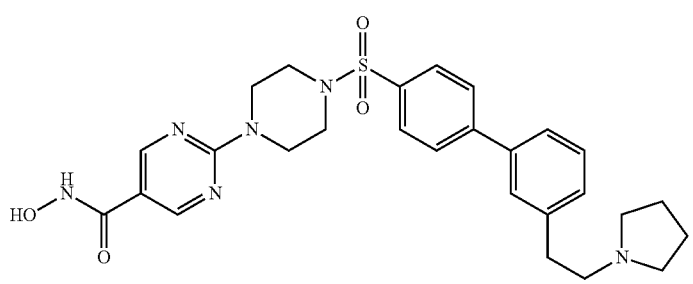
•1.16 C₂HF₃O₂; Co. No. 127; Ex. [B31]; mp. 243° C.

TABLE F-1-continued
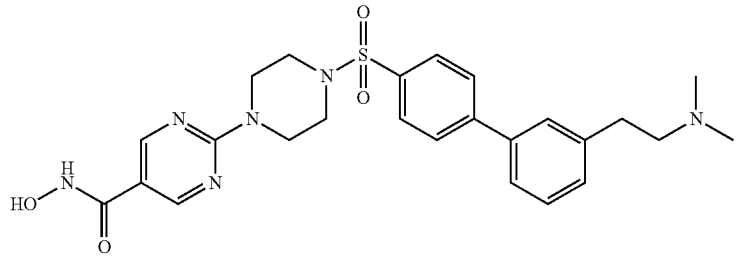
•1.18 C₂HF₃O₂; Co. No. 172; Ex. [B31];
mp. 254° C.
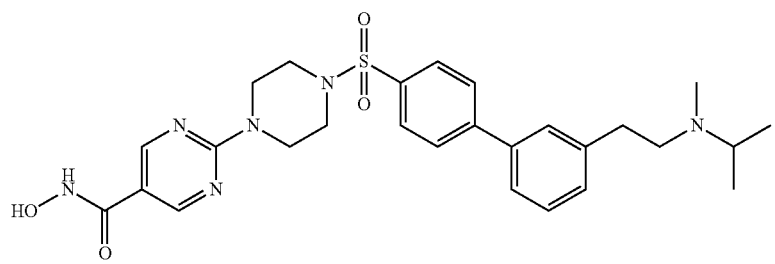
•1.17 C₂HF₃O₂; Co. No. 173; Ex. [B31];
mp. 224° C.
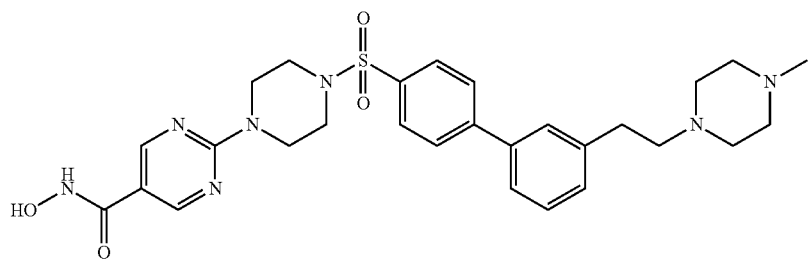
•C₂HF₃O₂; Co. No. 174; Ex. [B31]; mp.
164° C.
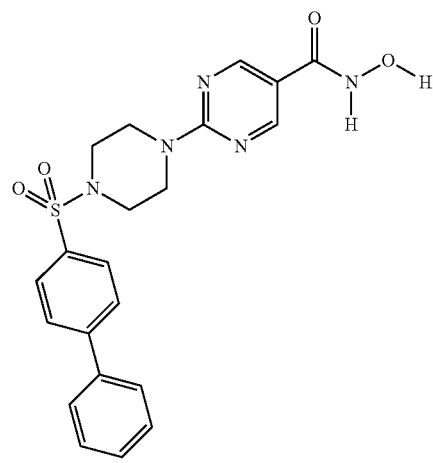
Co. No. 128; Ex. [B32]

TABLE F-1-continued
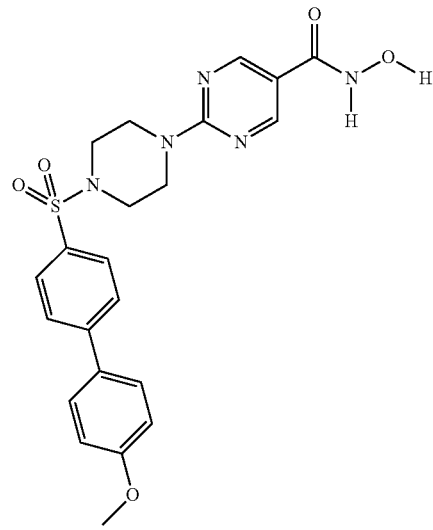
Co. No. 175; Ex. [B32]
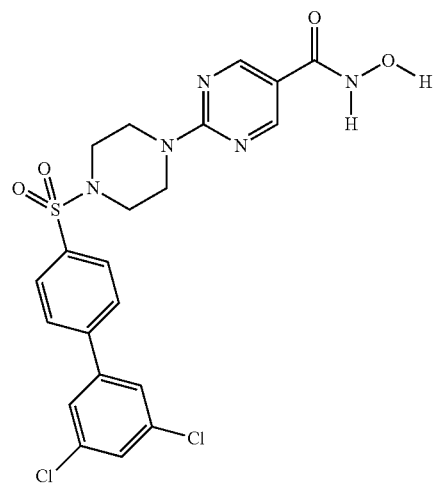
Co. No. 176; Ex. [B32]
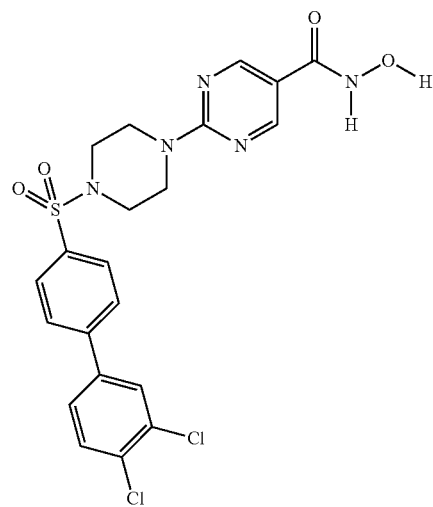
Co. No. 177; Ex. [B32]

TABLE F-1-continued
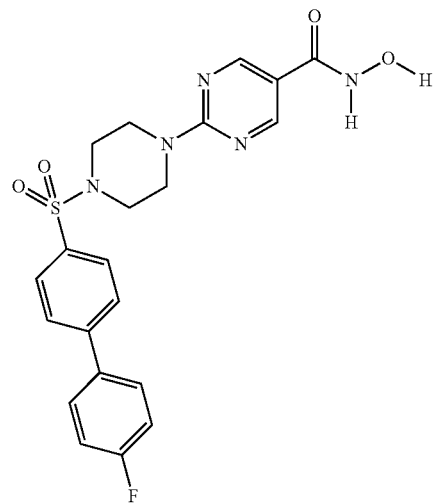
Co. No. 178; Ex. [B32]
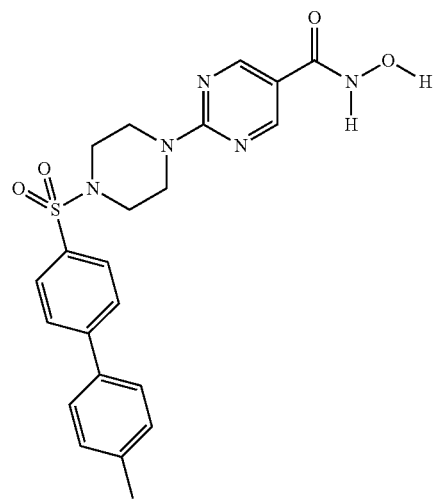
Co. No. 179; Ex. [B32]
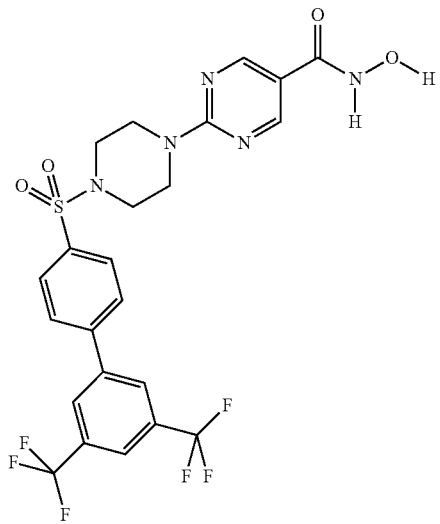
Co. No. 180; Ex. [B32]

TABLE F-1-continued
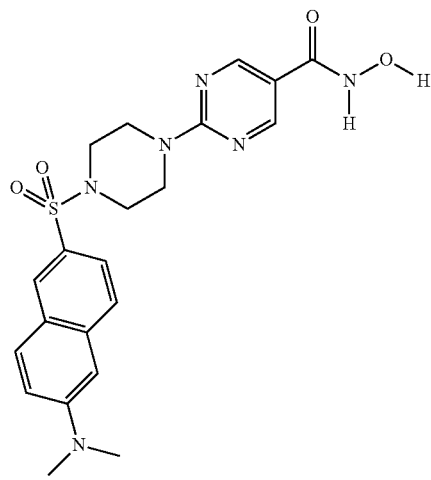
Co. No. 181; Ex. [B32]
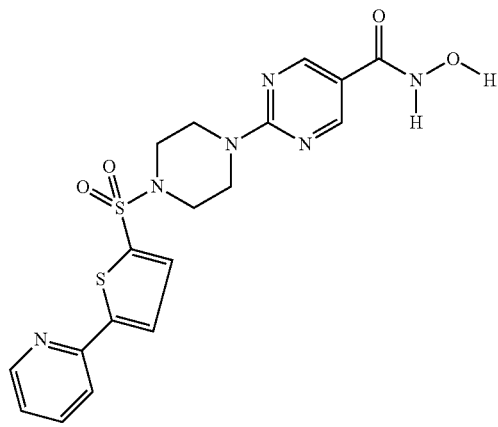
Co. No. 182; Ex. [B32]
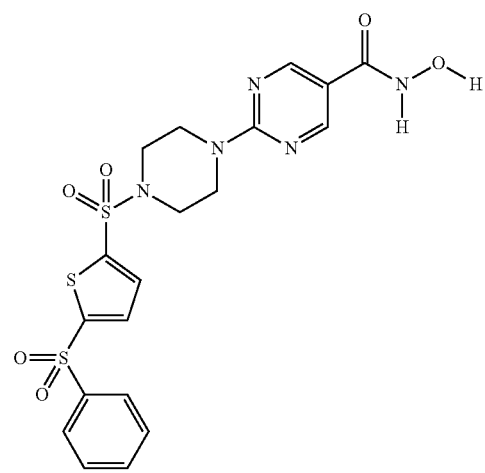
Co. No. 183; Ex. [B32]

TABLE F-1-continued
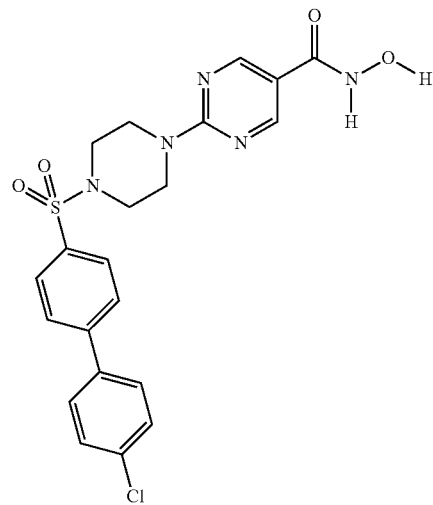
Co. No. 184; Ex. [B32]
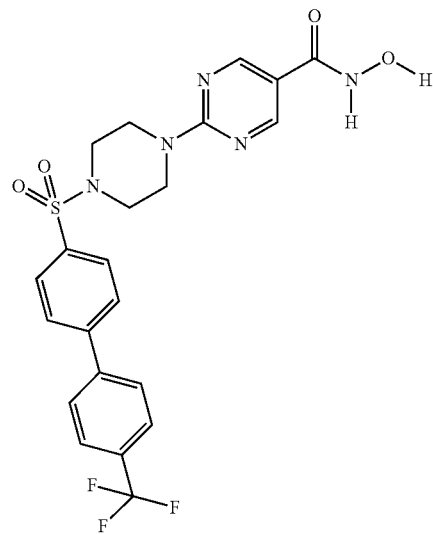
Co. No. 185; Ex. [B32]
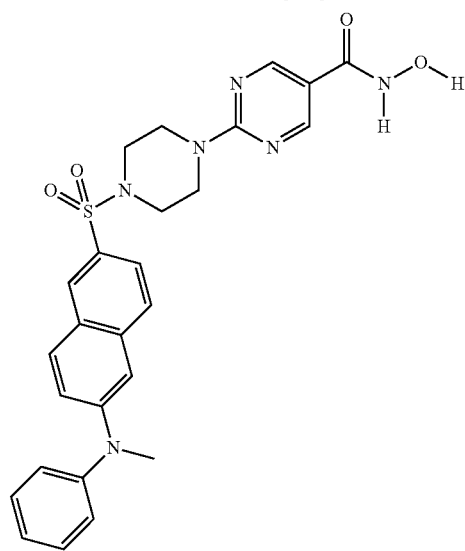
Co. No. 186; Ex. [B32]

TABLE F-1-continued

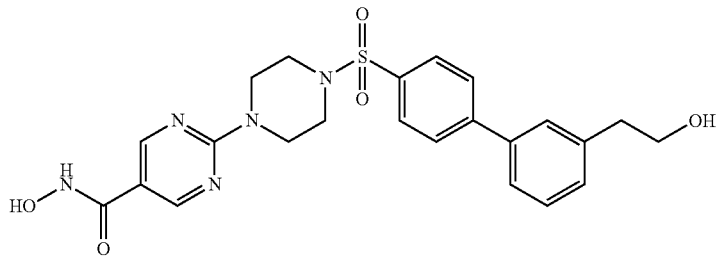

Co. No. 129; Ex. [B33]; mp. >260° C.

C. PHARMACOLOGICAL EXAMPLE

The in vitro assay for inhibition of histone deacetylase (see example C.1) measures the inhibition of HDAC enzymatic activity obtained with the compounds of formula (I).

Cellular activity of the compounds of formula (I) was determined on A2780 tumour cells using a colorimetric assay for cell toxicity or survival (Mosmann Tim, Journal of Immunological Methods 65: 55-63, 1983) (see example C.2).

Kinetic solubility in aqueous media measures the ability of a compound to stay in aqueous solution upon dilution (see example C.3).

DMSO-stock solutions are diluted with a single aqueous buffer solvent in 3 consecutive steps. For every dilution turbidity is measured with a nephelometer.

A drug's permeability expresses its ability to move from one medium into or through another. Specifically its ability to move through the intestinal membrane into the blood stream and/or from the blood stream into the target. Permeability (see example C.4) can be measured through the formation of a filter-immobilized artificial membrane phospholipid bilayer. In the filter-immobilized artificial membrane assay, a "sandwich" is formed with a 96-well microtitre plate and a 96-well filter plate, such that each composite well is divided into two chambers with a donor solution at the bottom and an acceptor solution at the top, separated by a 125 μm microfilter disc (0.45 μm pores), coated with 2% (wt/v) dodecane solution of dioleoylphosphatidyl-choline, under conditions that multi-lamellar bilayers form inside the filter channels when the system contacts an aqueous buffer solution. The permeability of compounds through this artificial membrane is measured in cm/s. The purpose is to look for the permeation of the drugs through a parallel artificial membrane at 2 different pH's: 4.0 and 7.4. Compound detection is done with UV-spectrometry at optimal wavelength between 250 and 500 nm.

Metabolism of drugs means that a lipid-soluble xenobiotic or endobiotic compound is enzymatically transformed into (a) polar, water-soluble, and excretable metabolite(s). The major organ for drug metabolism is the liver. The metabolic products are often less active than the parent drug or inactive. However, some metabolites may have enhanced activity or toxic effects. Thus drug metabolism may include both "detoxication" and "toxication" processes. One of the major enzyme systems that determine the organism's capability of dealing with drugs and chemicals is represented by the cytochrome P450 monooxygenases, which are NADPH dependent enzymes. Metabolic stability of compounds can be determined in vitro with the use of subcellular human tissue (see example C.5). Here metabolic stability of the compounds is expressed as % of drug metabolised after 15 minutes incubation of these compounds with microsomes. Quantitation of the compounds was determined by LC-MS analysis.

The tumour suppressor p53 transcriptionally activates a number of genes including the WAF1/CIP1 gene in response to DNA damage. The 21 kDa product of the WAF1 gene is found in a complex involving cyclins, cyclin dependent kinases (CDKs), and proliferating cell nuclear antigen (PCNA) in normal cells but not transformed cells and appears to be a universal inhibitor of CDK activity. One consequence of p21WAF1 binding to and inhibiting CDKs is to prevent CDK-dependent phosphorylation and subsequent inactivation of the Rb protein, which is essential for cell cycle progression. Induction of p21WAF1 in response to cellular contact with a HDAC inhibitor is therefore a potent and specific indicator of inhibition of cell cycle progression at both the G1 and G2 checkpoints.

The capacity of the compounds to induce p21WAF1 was measured with the p21WAF1 enzyme linked immunosorbent assay (WAF1 ELISA of Oncogene). The p21WAF1 assay is a "sandwich" enzyme immunoassay employing both mouse monoclonal and rabbit polyclonal antibodies. A rabbit polyclonal antibody, specific for the human WAF1 protein, has been immobilized onto the surface of the plastic wells provided in the kit. Any p21WAF present in the sample to be assayed will bind to the capture antibody. The biotinylated detector monoclonal antibody also recognizes human p21WAF1 protein, and will bind to any p21WAF1, which has been retained by the capture antibody. The detector antibody, in turn, is bound by horseradish peroxidas-conjugated streptavidin. The horseradish peroxidase catalyses the conversion of the chromogenic substrate tetra-methylbenzidine from a colorless solution to a blue solution (or yellow after the addition of stopping reagent), the intensity of which is proportional to the amount of p21WAF1 protein bound to the plate. The colored reaction product is quantified using a spectrophotometer. Quantitation is achieved by the construction of a standard curve using known concentrations of p21WAF1 (provided lyophilised) (see example C.6).

Specific HDAC inhibitors should not inhibit other enzymes like the abundant CYP P450 proteins. The CYP P450 (E. coli expressed) proteins 3A4, 2D6 en 2C9 convert their specific substrates into a fluorescent molecule. The CYP3A4 protein converts 7-benzyloxy-trifluoromethyl coumarin (BFC) into 7-hydroxy-trifluoromethyl coumarin. The CYP2D6 protein converts 3-[2-(N,N-diethyl-N-methylamino)ethyl]-7-methoxy-4-methylcoumarin (AMMC) into 3-[2-(N,N-diethylamino)ethyl]-7-hydroxy-4-methylcoumarin hydrochloride and the CYP2C9 protein converts 7-Methoxy-4-trifluoromethyl coumarin (MFC) into 7-hydroxy-trifluoromethyl coumarin. Compounds inhibiting the enzymatic reaction will result in a decrease of fluorescent signal (see example C.7).

Example C.1

In Vitro Assay for Inhibition of Histone Deacetylase

HeLa nuclear extracts (supplier: Biomol) were incubated at 60 µg/ml with $2\times10^{-8}$ M of radiolabeled peptide substrate. As a substrate for measuring HDAC activity a synthetic peptide, i.e. the amino acids 14-21 of histone H4, was used. The substrate is biotinylated at the $NH_2$-terminal part with a 6-aminohexanoic acid spacer, and is protected at the COOH-terminal part by an amide group and specifically [$^3$H]acetylated at lysine 16. The substrate, biotin-(6-aminohexanoic) Gly-Ala-([$^3$H]-acetyl-Lys-Arg-His-Arg-Lys-Val-$NH_2$), was added in a buffer containing 25 mM Hepes, 1 M sucrose, 0.1 mg/ml BSA and 0.01% Triton X-100 at pH 7.4. After 30 min the deacetylation reaction was terminated by the addition of HCl and acetic acid. (final concentration 0.035 mM and 3.8 mM respectively). After stopping the reaction, the free $^3$H-acetate was extracted with ethylacetate. After mixing and centrifugation, the radioactivity in an aliquot of the upper (organic) phase was counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-12}$M. In each test the blank value was subtracted from both the control and the sample values. The control sample represented 100% of substrate deactylation. For each sample the radioactivity was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value). All tested compounds showed enzymatic activity at a test concentration of $10^{-5}$M and 144 compounds had a $pIC_{50} \geq 5$ (see table F-2).

Example C.2

Determination of Antiproliferative Activity on A2780 Cells

All compounds tested were dissolved in DMSO and further dilutions were made in culture medium. Final DMSO concentrations never exceeded 0.1% (v/v) in cell proliferation assays. Controls contained A2780 cells and DMSO without compound and blanks contained DMSO but no cells. MTT was dissolved at 5 mg/ml in PBS. A glycine buffer comprised of 0.1 M glycine and 0.1 M NaCl buffered to pH 10.5 with NaOH (1 N) was prepared (all reagents were from Merck).

The human A2780 ovarian carcinoma cells (a kind gift from Dr. T. C. Hamilton [Fox Chase Cancer Centre, Pennsylvania, USA]) were cultured in RPMI 1640 medium supplemented with 2 mM L-glutamine, 50 µg/ml gentamicin and 10% fetal calf serum. Cells were routinely kept as monolayer cultures at 37° C. in a humidified 5% $CO_2$ atmosphere. Cells were passaged once a week using a trypsin/EDTA solution at a split ratio of 1:40. All media and supplements were obtained from Life Technologies. Cells were free of mycoplasma contamination as determined using the Gen-Probe Mycoplasma Tissue Culture kit (supplier: BioMérieux).

Cells were seeded in NUNC™ 96-well culture plates (Supplier: Life Technologies) and allowed to adhere to the plastic overnight. Densities used for plating were 1500 cells per well in a total volume of 200 µl medium. After cell adhesion to the plates, medium was changed and drugs and/or solvents were added to a final volume of 200 µl. Following four days of incubation, medium was replaced by 200 µl fresh medium and cell density and viability was assessed using an MTT-based assay. To each well, 25 µl MTT solution was added and the cells were further incubated for 2 hours at 37° C. The medium was then carefully aspirated and the blue MTT-formazan product was solubilized by addition of 25 µl glycine buffer followed by 100 µl of DMSO. The microtest plates were shaken for 10 min on a microplate shaker and the absorbance at 540 nm was measured using an Emax 96-well spectrophotometer (Supplier: Sopachem). Within an experiment, the results for each experimental condition are the mean of 3 replicate wells. For initial screening purposes, compounds were tested at a single fixed concentration of $10^{-6}$ M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value). Most of the tested compounds showed cellular activity at a test concentration of $10^{-6}$ M and 129 compounds had a $pIC_{50} \geq 5$ (see table F-2)

Example C.3

Kinetic Solubility in Aqueous Media

In the first dilution step, 10 µl of a concentrated stock-solution of the active compound, solubilized in DMSO (5 mM), was added to 100 µl phosphate citrate buffer pH 7.4 and mixed. In the second dilution step, an aliquot (20 µl) of the first dilution step was further dispensed in 100 µl phosphate citrate buffer pH 7.4 and mixed. Finally, in the third dilution step, a sample (20 µl) of the second dilution step was further diluted in 100 µl phosphate citrate buffer pH 7.4 and mixed. All dilutions were performed in 96-well plates. Immediately after the last dilution step the turbidity of the three consecutive dilution steps were measured with a nephelometer. Dilution was done in triplicate for each compound to exclude occasional errors. Based on the turbidity measurements a ranking is performed into 3 classes. Compounds with high solubility obtained a score of 3 and for this compounds the first dilution is clear. Compounds with medium solubility obtained a score of 2. For these compounds the first dilution is unclear and the second dilution is clear. Compounds with low solubility obtained a score of 1 and for these compounds both the first and the second dilution are unclear. The solubility of 112 compounds was measured. From these compounds 42 showed a score of 3, thirty-two had a score of 2 and 38 demonstrated a score of 1 (see table F-2).

Example C.4

Parallel Artificial Membrane Permeability Analysis

The stock samples (aliquots of 10 µl of a stock solution of 5 mM in 100% DMSO) were diluted in a deep-well or Pre-mix plate containing 2 ml of an aqueous buffer system pH 4 or pH 7.4 (PSR4System Solution Concentrate (pION)). Before samples were added to the reference plate, 150 µl of buffer was added to wells and a blank UV-measurement was performed. Thereafter the buffer was discarded and the plate was used as reference plate. All measurements were done in UV-resistant plates (supplier: Costar or Greiner).

After the blank measurement of the reference plate, 150 µl of the diluted samples was added to the reference plate and 200 µl of the diluted samples was added to donor plate 1. An acceptor filter plate 1 (supplier: Millipore, type: MAIP N45) was coated with 4 µl of the artificial membrane-forming solution (1,2-Dioleoyl-sn-Glycer-3-Phosphocholine in Dodecane containing 0.1% 2,6-Di-tert-butyl-4-methylphenol and placed on top of donor plate 1 to form a "sandwich". Buffer (200 µl) was dispensed into the acceptor wells on the top. The sandwich was covered with a lid and stored for 18 h at room temperature in the dark.

A blank measurement of acceptor plate 2 was performed through the addition of 150 µl of buffer to the wells, followed by an UV-measurement. After the blank measurement of acceptor plate 2 the buffer was discarded and 150 µl of acceptor solution was transferred from the acceptor filter plate 1 to the acceptor plate 2. Then the acceptor filter plate 1 was removed form the sandwich. After the blank measurement of donor plate 2 (see above), 150 µl of the donor solution was transferred from donor plate 1 to donor plate 2. The UV spectra of the donor plate 2, acceptor plate 2 and reference plate wells were scanned (with a SpectraMAX 190). All the spectra were processed to calculate permeability with the PSR4p Command Software. All compounds were measured in triplo. Carbamazepine, griseofulvin, acycloguanisine, atenolol, furosemide, and chlorothiazide were used as standards in each experiment. Compounds were ranked in 3 categories as having a low permeability (mean effect<$0.5 \times 10^{-6}$ cm/s; score 1), a medium permeability ($1 \times 10^{-6}$ cm/s>mean effect $0.5 \times 10^{-6}$ cm/s; score 2) or a high permeability ($\geq 0.5 \times 10^{-6}$ cm/s; score 3). Fourteen of the 22 tested compounds showed at least a score of 3 at one of both pH's measured. Three compounds showed at least a score of 2 at one of the pH's measured and 5 compounds showed only a score of 1 at one of the pH's measured.

Example C.5

Metabolic Stability

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4) using either a Potter-S (Braun, Italy) equipped with a Teflon pestle or a Sorvall Omni-Mix homogeniser, for 7×10 sec. In both cases, the vessel was kept in/on ice during the homogenization process.

Tissue homogenates were centrifuged at 9000×g for 20 minutes at 4° C. using a Sorvall centrifuge or Beckman Ultracentrifuge. The resulting supernatant was stored at −80° C. and is designated 'S9'.

The S9 fraction can be further centrifuged at 100.000×g for 60 minutes (4° C.) using a Beckman ultracentrifuge. The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 µM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 min at 95 degrees Celsius) microsomes. Recovery of the compounds in the control samples was always 100%.

The mixtures were preincubated for 5 min at 37 degrees Celsius. The reaction was started at timepoint zero (t=0) by addition of 0.8 mM NADP and the samples were incubated for 15 min (t=15). The reaction was terminated by the addition of 2 volumes of DMSO. Then the samples were centrifuged for 10 min at 900×g and the supernatants were stored at room temperature for no longer as 24 h before analysis. All incubations were performed in duplo. Analysis of the supernatants was performed with LC-MS analysis. Elution of the samples was performed on a Xterra MS C18 (50×4.6 mm, 5 µm, Waters, US). An Alliance 2790 (Supplier: Waters, US) HPLC system was used. Elution was with buffer A (25 mM ammoniumacetate (pH 5.2) in H$_2$O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 min in a linear fashion and organic phase concentration was kept stationary for an additional 1.5 min. Total injection volume of the samples was 25 µl.

A Quattro (supplier: Micromass, Manchester, UK) triple quadrupole mass spectrometer fitted with and ESI source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 sec.

Metabolic stability was expressed as % metabolism of the compound after 15 min of incubation in the presence of active microsomes $$(E(\text{act})) \ (\% \ \text{metabolism} = 100\% - \left(\left(\frac{\text{Total Ion Current } (TIC) \text{ of } E(\text{act}) \text{ at } t = 15}{TIC \text{ of } E(\text{act}) \text{ at } t = 0}\right) \times 100\right).$$

Compounds that had a percentage metabolism less than 20% were defined as highly metabolic stable. Compound that had a metabolism between 20 and 70% were defined as intermediately stable and compounds that showed a percentage metabolism higher than 70 were defined as low metabolic stable. Three reference compounds were always included whenever a metabolic stability screening was performed. Verapamil was included as a compound with low metabolic stability (% metabolism=73%). Cisapride was included as a compound with medium metabolic stability (% metabolism 45%) and propanol was included as a compound with intermediate to high metabolic stability (25% metabolism). These reference compounds were used to validate the metabolic stability assay.

Twenty-eight compounds were tested. Fourteen compounds had a percentage metabolism less than 20% and fourteen compounds had a percentage metabolism between 20 and 70%.

Example C.6 p21 Induction Capacity

The following protocol has been applied to determine the p21 protein expression level in human A2780 ovarian carcinoma cells. The A2780 cells (20000 cells/180 μl) were seeded in 96 microwell plates in RPMI 1640 medium supplemented with 2 mM L-glutamine, 50 μg/ml gentamicin and 10% fetal calf serum. 24 hours before the lysis of the cells, compounds were added at final concentrations of $10^{-5}$, $10^{-6}$, $10^{-7}$ and $10^{-8}$ M. All compounds tested were dissolved in DMSO and further dilutions were made in culture medium. 24 hours after the addition of the compound, the supernatants were removed from the cells. Cells were washed with 200 μl ice-cold PBS. The wells were aspirated and 30 μl of lysisbuffer (50 mM Tris.HCl (pH 7.6), 150 mM NaCl, 1% Nonidet p40 and 10% glycerol) was added. The plates were incubated overnight at −70° C.

The appropriate number of microtiter wells were removed from the foil pouch and placed into an empty well holder. A working solution (1×) of the Wash Buffer (20× plate wash concentrate: 100 ml 20-fold concentrated solution of PBS and surfactant. Contains 2% chloroacetamide) was prepared. The lyophilised p21WAF standard was reconstituted with distilled $H_2O$ and further diluted with sample diluent (provided in the kit)

The samples were prepared by diluting them 1:4 in sample diluent. The samples (100 μl) and the p21WAF1 standards (100 μl) were pipetted into the appropriate wells and incubated at room temperature for 2 hours. The wells were washed 3 times with 1× wash buffer and then 100 μl of detector antibody reagent (a solution of biotinylated monoclonal p21WAF1 antibody) was pipetted into each well. The wells were incubated at room temperature for 1 hour and then washed three times with 1× wash buffer. The 400× conjugate (peroxidase streptavidine conjugate: 400-fold concentrated solution) was diluted and 100 μl of the 1× solution was added to the wells. The wells were incubated at room temperature for 30 min and then washed 3 times with 1× wash buffer and 1 time with distilled $H_2O$, Substrate solution (chromogenic substrate)(100 μl) was added to the wells and the wells were incubated for 30 minutes in the dark at room temperature. Stop solution was added to each well in the same order as the previously added substrate solution. The absorbance in each well was measured using a spectrophotometric plate reader at dual wavelengths of 450/595 nm.

For each experiment, controls (containing no drug) and a blank incubation (containing no cells or drugs) were run in parallel. The blank value was subtracted from all control and sample values. For each sample, the value for p21WAF1 induction (in absorbance units) was expressed as the percentage of the value for p21WAF1 present in the control. Percentage induction higher than 130% was defined as significant induction. Seventy-nine compounds were tested in this assay. Sixty-six showed significant induction.

Example C.7

P450 Inhibiting Capacity

All compounds tested were dissolved in DMSO (5 mM) and a further dilution to $5\ 10^{-4}$ M was made in acetonitrile. Further dilutions were made in assay buffer (0.1M NaK phosphate buffer pH 7.4) and the final solvent concentration was never higher than 2%.

The assay for the CYP3A4 protein comprises per well 15 pmol P450/mg protein (in 0.01M NaKphosphate buffer+1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 μl. After a 5 min pre-incubation at 37° C. the enzymatic reaction was started with the addition of 150 μM of the fluorescent probe substrate BFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Ketoconazole ($IC_{50}$-value=$3\times10^{-8}$M) was included as reference compound in this experiment. The assay for the CYP2D6 protein comprises per well 6 pmol P450/mg protein (in 0.01M NaKphosphate buffer+1.15% KCl), an NADPH generating system (0.41 mM Glucose-6-phosphate, 0.4 U/ml Glucose-6-phosphate dehydrogenase, 0.0082 mM NADP and 0.41 mM $MgCl_2.6H_2O$ in assay buffer) and compound in a total assay volume of 100 μl. After a 5 min pre-incubation at 37° C. the enzymatic reaction was started with the addition of 3 μM of the fluorescent probe substrate AMMC in assay buffer. After an incubation of 45 minutes at room temperature the reaction was terminated after addition of 2 volumes of acetonitrile. Fluorescent determinations were carried out at an excitation wavelength of 405 nm and an emission wavelength of 460 nm. Quinidine ($IC_{50}$-value<$5\times10^{-8}$M) was included as reference compound in this experiment.

The assay for the CYP2C9 protein comprises per well 15 pmol P450/mg protein (in 0.01M NaKphosphate buffer+1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 μl. After a 5 min pre-incubation at 37° C. the enzymatic reaction was started with the addition of 200 μM of the fluorescent probe substrate MFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Sulfaphenazole ($IC_{50}$-value=$6.8\times10^{-7}$M) was included as reference compound in this experiment.

For initial screening purposes, compounds were tested at a single fixed concentration of $1\times10^{-6}$ M. For active compounds, the experiments were repeated to establish full concentration-response curves. For each experiment, controls (containing no drug) and a blank incubation (containing no enzyme or drugs) were run in parallel. All compounds were assayed in quadruplicate. The blank value was subtracted from all control and sample values. For each sample, the mean value of P450 activity of the sample (in relative fluorescence units) was expressed as a percentage of the mean value of P450 activity of the control. Percentage inhibition was expressed as 100% minus the mean value of P450 activity of the sample. When appropriate, $IC_{50}$-values (concentration of the drug, needed to reduce P450 activity to 50% of the control) were calculated. Four compounds were analysed in this assay. For only one compound an $IC_{50}$-value of $7.9\times10^{-6}$ M could be determined with the CYP3A4 protein.

Example C.8

A 2780 Mouse Xenograft Model

Immunodeficient mice were injected subcutaneously with A 2780 ovarium carcinoma cells ($10^7$ cells/200 µl/mouse). Subsequently they were orally treated with 10, 20 and 40 mpk of compound once daily between day 4 and day 32. The compound was dissolved in 0.9% NaCl, 20% β-cyclodextrine. On day 32 tumours were harvested and individual tumour weight of each mouse was determined. Each experiment included 10 mice.

Two independent A2780 xenograft study dosing compound No 6 orally at 10, 20, and 40 mpk once daily showed a strong antitumoural effect at all doses, with a maximal inhibition once at 20 mpk, and once at 40 mpk.

TABLE F-2

Table F-2 lists the results of the compounds that were tested according to example C.1, C.2, and C.3.

| Co. No. | Enzyme activity pIC50 | Cellular activity pIC50 | Solubility Score |
|---|---|---|---|
| 1 | 6.482 | <5 | |
| 2 | 7.147 | 5.713 | 1 |
| 3 | <5 | <5 | 1 |
| 4 | <5 | <5 | 2 |
| 5 | <5 | <5 | |
| 6 | 8.186 | 7.336 | 2 |
| 7 | <5 | | |
| 8 | 7.587 | 5.642 | 3 |
| 9 | <5 | 5.411 | |
| 10 | 6.7 | <5 | 1 |
| 11 | <5 | 5.995 | |
| 12 | <5 | 5.086 | |
| 13 | <5 | 6.355 | 1 |
| 14 | 6.621 | 5.237 | 3 |
| 15 | 7.332 | 6.971 | 2 |
| 16 | <5 | <5 | |
| 17 | <5 | 6.117 | 1 |
| 18 | <5 | 5.389 | 1 |
| 19 | <5 | <5 | 1 |
| 20 | >5 | | |
| 21 | 6.38 | | |
| 22 | <5 | | |
| 23 | >5 | | |
| 24 | >5 | | |
| 26 | >5 | | |
| 28 | 5.265 | | |
| 29 | >5 | | |
| 30 | >5 | | |
| 32 | 5.835 | | |
| 33 | >5 | | |
| 37 | 5.624 | | |
| 42 | >5 | | |
| 43 | >5 | | |
| 44 | >5 | | |
| 49 | >5 | | |
| 52 | >5 | | |
| 55 | >5 | | |
| 56 | <5 | | |
| 57 | >5 | | |
| 58 | >5 | | |
| 60 | 6.247 | 5.344 | 3 |
| 61 | 6.255 | 5.555 | 2 |
| 62 | 5.409 | 6.416 | 1 |
| 63 | 6.215 | 5.731 | 1 |
| 64 | 5.753 | 5.05 | 3 |
| 65 | 5.775 | <5 | 3 |
| 66 | 6.197 | 5.877 | 1 |
| 67 | 5.177 | 6.068 | 1 |
| 68 | 6.908 | 5.911 | 1 |
| 69 | 5.978 | <5 | 3 |
| 70 | 5.914 | 5.391 | 3 |
| 71 | 6.449 | 5.608 | 3 |
| 72 | 6.346 | 6.026 | 1 |
| 73 | 6.212 | 5.402 | 1 |
| 74 | 5.841 | 5.584 | 2 |
| 75 | <5 | 5.163 | |
| 76 | 6.227 | 5.867 | 1 |
| 77 | 5.937 | 5.149 | |
| 78 | 6.306 | 5.904 | 2 |
| 79 | 6.238 | 5.368 | 1 |
| 80 | 5.961 | 5.909 | 1 |
| 81 | 6.873 | 5.887 | 1 |
| 82 | 5.821 | 5.968 | 3 |
| 83 | 6.157 | 5.886 | 1 |
| 84 | <5 | <5 | |
| 85 | <5 | <5 | |
| 86 | <5 | <5 | |
| 87 | <5 | <5 | |
| 88 | 6.481 | 5.547 | 3 |
| 89 | 6.423 | 5.217 | |
| 90 | 7.467 | 5.953 | 3 |
| 91 | 7.688 | 6.106 | 3 |
| 92 | 7.876 | 6.141 | |
| 93 | 7.464 | 6.342 | 3 |
| 94 | 7.497 | 6.661 | 2 |
| 95 | 7.363 | 5.957 | 3 |
| 96 | 7.49 | 6.475 | 3 |
| 97 | 7.938 | 6.903 | |
| 98 | 7.054 | 6.448 | 2 |
| 99 | 7.316 | 6.617 | 3 |
| 100 | 8.171 | 7.237 | 2 |
| 101 | 6.671 | 6.994 | |
| 102 | 7.162 | 6.452 | 2 |
| 103 | 7.586 | 6.826 | 2 |
| 104 | 8.152 | 7.233 | |
| 105 | 6.494 | 6.098 | 1 |
| 106 | 7.797 | 6.589 | 2 |
| 107 | 7.663 | 6.841 | 2 |
| 108 | 8.117 | 6.679 | 1 |
| 109 | 7.176 | 6.588 | 2 |
| 110 | 7.713 | 6.352 | 2 |
| 111 | 7.561 | 6.357 | 1 |
| 112 | 7.54 | 6.482 | 3 |
| 113 | <5 | <5 | |
| 114 | 7.428 | 6.125 | 3 |
| 115 | <5 | 5.695 | |
| 116 | 7.159 | 6.065 | 1 |
| 117 | <5 | 5.759 | |
| 118 | 6.741 | 5.276 | 3 |
| 119 | 5.215 | <5 | |
| 120 | 6.491 | 5.994 | 1 |
| 121 | 6.833 | 5.557 | 3 |
| 122 | 7.06 | <5 | |
| 123 | 6.787 | 5.589 | 3 |
| 124 | 8.358 | 7.32 | 3 |
| 125 | 8.659 | 7.031 | 2 |
| 126 | 8.456 | 6.989 | 1 |
| 127 | 8.482 | 7.162 | 3 |
| 128 | 8.078 | 7.09 | 2 |
| 129 | 7.107 | 6.687 | 3 |
| 130 | 6.159 | 6.124 | 2 |
| 131 | 6.058 | 6.263 | 2 |
| 132 | 7.162 | 6.336 | |
| 133 | 7.869 | 5.899 | 2 |
| 134 | 7.662 | 6.501 | 2 |
| 135 | 7.631 | 6.542 | 3 |
| 136 | 7.288 | 6.29 | 1 |
| 137 | 7.169 | 5.951 | 2 |
| 138 | 7.545 | 6.604 | 2 |
| 139 | 7.612 | 7.258 | |

TABLE F-2-continued

Table F-2 lists the results of the compounds that were tested according to example C.1, C.2, and C.3.

| Co. No. | Enzyme activity pIC50 | Cellular activity pIC50 | Solubility Score |
|---|---|---|---|
| 140 | 7.739 | 7.001 | |
| 141 | 7.125 | 6.004 | |
| 142 | 8.01 | 6.543 | 3 |
| 143 | 7.002 | 5.879 | 3 |
| 144 | 8.428 | 7.089 | 3 |
| 145 | 8.06 | 6.555 | 1 |
| 146 | 8.565 | 6.926 | |
| 147 | 6.765 | 6.159 | 1 |
| 148 | 7.94 | 6.755 | 1 |
| 149 | 8.175 | 6.843 | 2 |
| 150 | 8.011 | 6.784 | 2 |
| 151 | 8.152 | 6.864 | 3 |
| 152 | 8.156 | 6.785 | 3 |
| 153 | 8.7 | 6.561 | |
| 154 | 8.869 | 7.194 | 1 |
| 155 | 7.939 | 7.06 | |
| 156 | 8.568 | 7.523 | |
| 157 | 8.228 | 7.017 | 3 |
| 158 | 7.784 | 6.351 | 2 |
| 159 | 8.61 | 7.018 | 3 |
| 160 | 8.272 | 6.556 | 2 |
| 162 | 8.215 | 6.933 | 3 |
| 162 | 7.83 | 7.039 | 1 |
| 163 | 8.553 | 7.37 | |
| 164 | 8.308 | 7.316 | 2 |
| 165 | 7.947 | 7.255 | 1 |
| 166 | 7.969 | 7.212 | 1 |
| 167 | 7.579 | 6.968 | 3 |
| 168 | 8.766 | 7.195 | 3 |
| 169 | 8.338 | 7.14 | 3 |
| 170 | 8.227 | 7.185 | 3 |
| 171 | 8.45 | 7.327 | 3 |
| 172 | 8.566 | 7.191 | 3 |
| 173 | 8.423 | 7.152 | 3 |
| 174 | 8.212 | 7.095 | 3 |
| 175 | 7.691 | 7.162 | 1 |
| 176 | 6.513 | 6.082 | 2 |
| 177 | 6.428 | 6.511 | 1 |
| 178 | 7.99 | 7.122 | 1 |
| 179 | 7.146 | 6.925 | 2 |
| 180 | <5 | <5 | |
| 181 | 7.098 | 6.925 | 3 |
| 182 | 7.634 | 7.06 | 1 |
| 183 | 7.631 | 5.634 | 2 |
| 184 | 7.22 | 7.202 | 1 |
| 185 | 6.417 | 6.795 | 1 |
| 186 | 6.539 | 6.253 | 2 |

D. COMPOSITION EXAMPLE

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I),

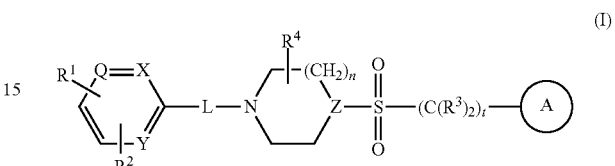

or an N-oxide form, pharmaceutically acceptable addition salt or stereo-chemically isomeric form thereof, wherein n is 1;

t is 0 and a direct bond is intended;

Q is

X is

Y is nitrogen;

Z is nitrogen;

$R^1$ is —C(O)NR$^7$R$^8$, —N(H)C(O)R$^9$, —C(O)—C$_{1-6}$alkanediylSR$^9$, —NR$^{10}$C(O)N(OH)R$^9$, —NR$^{10}$C(O)C$_{1-6}$alkanediylSR$^9$, —NR$^{10}$C(O)C=N(OH)R$^9$ or another Zn-chelating-group wherein $R^7$ and $R^8$ are each independently selected from hydrogen, hydroxy, C$_{1-6}$alkyl, hydroxyC$_{1-6}$alkyl, aminoC$_{1-6}$alkyl and aminoaryl;

$R^9$ is independently selected hydrogen, C$_{1-6}$alkyl, C$_{1-6}$alkylcarbonyl, arylC$_{1-6}$alkyl, C$_{1-6}$alkylpyrazinyl, pyridinone, pyrrolidinone and methylimidazolyl;

$R^{10}$ is independently selected from hydrogen and C$_{1-6}$alkyl;

$R^2$ is hydrogen, halo, hydroxy, amino, nitro, C$_{1-6}$alkyl, C$_{1-6}$alkyloxy, trifluoromethyl, di(C$_{1-6}$alkyl)amino, hydroxyamino or naphtalenylsulfonylpyrazinyl;

-L- is a direct bond;

each $R^3$ represents a hydrogen atom and one hydrogen atom is optionally replaced by aryl;

$R^4$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylamino C$_{1-6}$alkyl or di(C$_{1-6}$alkyl)amino C$_{1-6}$alkyl;

—A is a radical selected from

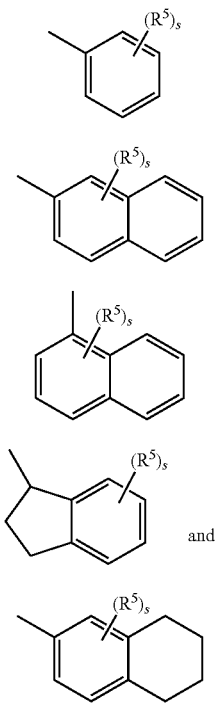

wherein each s is independently 0, 1, 2, 3, 4 or 5;
each $R^5$ is independently selected from hydrogen; halo; hydroxy; amino; nitro; trihalo$C_{1-6}$alkyl; trihalo$C_{1-6}$alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)amino carbonyl; di(hydroxy$C_{1-6}$alkyl)amino; (aryl)($C_{1-6}$alkyl)amino; di($C_{1-6}$alkyl)amino $C_{1-6}$alkyloxy; di($C_{1-6}$alkyl)amino $C_{1-6}$alkylamino; di($C_{1-6}$alkyl)amino $C_{1-6}$alkylamino $C_{1-6}$alkyl; arylsulfonyl; arylsulfonylamino; aryloxy; aryloxy$C_{1-6}$alkyl; aryl$C_{2-6}$ alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl: $C_{1-6}$alkylpiperazinyl$C_{1-6}$alkyl; $C_{1-6}$alkylpiperazinyl$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; amino sulfonylpiperazinyl; amino sulfonylpiperazinyl$C_{1-6}$alkyl; di($C_{1-6}$alkyl)amino sulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)(hydroxy$C_{1-6}$alkyl)amino$C_{1-6}$ alkylamino; ($C_{1-6}$alkylpiperidinyl)(hydroxy$C_{1-6}$alkyl)amino$C_{1-6}$alkylamino $C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino $C_{1-6}$alkyl; hydroxy$C_{1-6}$alkylamino$C_{1-6}$alkyl; di(hydroxy$C_{1-6}$alkyl)amino $C_{1-6}$alkyl; pyrrolidinyl$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indolyl; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkylsulfonyl, $C_{1-4}$alkyloxy$C_{1-4}$alkyloxy, $C_{1-4}$alkyloxycarbonyl, amino $C_{1-4}$alkyloxy, di($C_{1-4}$alkyl)amino $C_{1-4}$alkyloxy, di($C_{1-4}$alkyl)amino, di($C_{1-4}$alkyl)amino carbonyl, di($C_{1-4}$alkyl)amino $C_{1-4}$alkyl, di($C_{1-4}$alkyl)amino $C_{1-4}$alkylamino $C_{1-4}$alkyl, di($C_{1-4}$alkyl)amino ($C_{1-4}$alkyl)amino, di($C_{1-4}$alkyl)amino($C_{1-4}$alkyl)amino $C_{1-4}$alkyl, di($C_{1-4}$alkyl)amino $C_{1-4}$alkyl($C_{1-4}$alkyl)amino, di($C_{1-4}$alkyl)amino $C_{1-4}$alkyl($C_{1-4}$alkyl)amino $C_{1-4}$alkyl, aminosulfonylamino($C_{1-4}$alkyl)amino, aminosulfonylamino($C_{1-4}$alkyl)amino $C_{1-4}$alkyl, di($C_{1-4}$alkyl)amino sulfonylamino($C_{1-4}$alkyl)amino, di($C_{1-4}$alkyl)amino sulfonylamino($C_{1-4}$alkyl)amino $C_{1-6}$alkyl, cyano, piperidinyl$C_{1-4}$alkyloxy, pyrrolidinyl$C_{1-4}$alkyloxy, amino sulfonylpiperazinyl, aminosulfonylpiperazinyl$C_{1-4}$alkyl, di($C_{1-4}$alkyl)amino sulfonylpiperazinyl, di($C_{1-4}$alkyl)amino sulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino $C_{1-4}$alkyl, di(hydroxy$C_{1-4}$alkyl)amino, di(hydroxy$C_{1-4}$alkyl)amino$C_{1-4}$alkyl, furanyl, furanyl substituted with —CH═CH—CH═CH—, pyrrolidinyl$C_{1-4}$alkyl, pyrrolidinyl$C_{1-4}$alkyloxy, morpholinyl, morpholinyl$C_{1-4}$ alkyloxy, morpholinylC$_{1-4}$alkyl, morpholinylC$_{1-4}$alkylamino, morpholinylC$_{1-4}$alkylamino C$_{1-4}$alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinyl C$_{1-4}$alkyl, C$_{1-4}$alkylpiperazinylC$_{1-4}$alkylamino, C$_{1-4}$alkylpiperazinylC$_{1-4}$alkylamino C$_{1-6}$alkyl, tetrahydropyrimidinylpiperazinyl, tetrahydropyrimidinylpiperazinylC$_{1-4}$alkyl, piperidinylamino C$_{1-4}$alkylamino, piperidinylamino C$_{1-4}$alkylamino C$_{1-4}$alkyl, (C$_{1-4}$alkylpiperidinyl)(hydroxyC$_{1-4}$alkyl)amino C$_{1-4}$alkylamino, (C$_{1-4}$alkylpiperidinyl)(hydroxyC$_{1-4}$alkyl)amino C$_{1-4}$alkylamino C$_{1-4}$alkyl, pyridinylC$_{1-4}$alkyloxy, hydroxyC$_{1-4}$alkylamino, hydroxyC$_{1-4}$alkylamino C$_{1-4}$alkyl, di(C$_{1-4}$alkyl)amino C$_{1-4}$alkylamino, aminothiadiazolyl, aminosulfonylpiperazinylC$_{1-4}$alkyloxy, and thiophenylC$_{1-4}$alkylamino;

the central

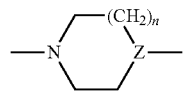

moiety is optionally bridged with a methylene, ethylene or propylene bridge;

each R$^5$ optionally replaces the hydrogen on the nitrogen; and aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

2. A compound as claimed in claim 1 wherein
R$^7$ and R$^8$ are each independently selected from hydrogen, hydroxy, hydroxyC$_{1-6}$alkyl, aminoC$_{1-6}$alkyl and aminoaryl;

R$^2$ is hydrogen, halo, hydroxy, amino, nitro, C$_{1-6}$alkyl, C$_{1-6}$alkyloxy, trifluoromethyl, hydroxyamino or naphtalenylsulfonylpyrazinyl;

R$^4$ is hydrogen, hydroxy, amino, hydroxyC$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyamino carbonyl, C$_{1-6}$alkyloxycarbonyl, C$_{1-6}$alkylaminoC$_{1-6}$alkyl or di(C$_{1-6}$alkyl)aminoC$_{1-6}$alkyl;

each R$^5$ is independently selected from hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkyloxyC$_{1-6}$alkyloxy; C$_{1-6}$alkylcarbonyl; C$_{1-6}$alkylsulfonyl; cyanoC$_{1-6}$alkyl; hydroxyC$_{1-6}$alkyl; hydroxyC$_{1-6}$alkyloxy; hydroxyC$_{1-6}$alkylamino; amino C$_{1-6}$alkyloxy; di(C$_{1-6}$alkyl)amino carbonyl; di(hydroxyC$_{1-6}$alkyl)amino; di(C$_{1-6}$alkyl)aminoC$_{1-6}$alkyloxy; di(C$_{1-6}$alkyl)aminoC$_{1-6}$alkylamino; arylsulfonyl; arylsulfonylamino; aryloxy; arylC$_{2-6}$alkenediyl; di(C$_{1-6}$alkyl)amino; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl or di(hydroxyC$_{1-6}$alkyl)aminoC$_{1-6}$alkyl; furanyl; imidazolyl; C$_{1-6}$alkyltriazolyl; tetrazolyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)amino C$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; phenyl; phenyl substituted with one, two or three substituents independently selected from halo, amino, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, piperidinylC$_{1-4}$alkyloxy, pyrrolidinylC$_{1-4}$alkyloxy, aminosulfonylpiperazinyl, amino sulfonylpiperazinylC$_{1-4}$alkyl, di(C$_{1-4}$alkyl)amino sulfonylpiperazinyl, di(C$_{1-4}$alkyl)amino sulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$ alkylpiperazinylC$_{1-4}$alkyl, (hydroxyC$_{1-4}$alkyl)(C$_{1-4}$ alkyl)amino, (hydroxyC$_{1-4}$alkyl)(C$_{1-4}$alkyl)amino C$_{1-4}$alkyl, pyrrolidinylC$_{1-4}$alkyloxy, morpholinylC$_{1-4}$ alkyloxy, morpholinylC$_{1-4}$alkyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl)amino C$_{1-4}$alkylamino, aminothiadiazolyl, aminosulfonylpiperazinylC$_{1-4}$alkyloxy, or thiophenylC$_{1-4}$alkylamino.

3. A compound as claimed in claim 1 wherein
R$^1$ is —C(O)NR$^7$R$^8$, —C(O)—C$_{1-6}$alkanediylSR$^9$, —NR$^{10}$C(O)N(OH)R$^9$, —NR$^{10}$C(O)C$_{1-6}$alkanediylSR$^9$, —NR$^{10}$C(O)C=N(OH)R$^9$ or another Zn-chelating-group wherein R$^7$ and R$^8$ are each independently selected from hydrogen, hydroxy, hydroxyC$_{1-6}$alkyl, and aminoC$_{1-6}$alkyl;

R$^2$ is hydrogen, halo, hydroxy, amino, nitro, C$_{1-6}$alkyl, C$_{1-6}$alkyloxy, trifluoromethyl or di(C$_{1-6}$alkyl)amino;

R$^4$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

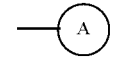

is a radical selected from (a-1), and;
each s is independently 0, 1, 2, 3 or 4; and R$^5$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoly; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;

the central

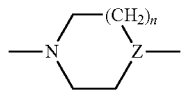

moiety is optionally bridged with an ethylene bridge.

4. A compound as claimed in claim 1 wherein $R^{10}$ is hydrogen; $R^2$ is hydrogen, nitro, $C_{1-6}$alkyloxy, trifluoromethyl, di($C_{1-6}$alkyl)amino, hydroxyamino or naphtalenylsulfonylpyrazinyl; each $R^3$ represents a hydrogen atom; $R^4$ is hydrogen, hydroxy$C_{1-6}$alkyl, aminocarbonyl, hydroxyaminocarbonyl or di($C_{1-6}$alkyl)amino$C_{1-6}$alkyl;

is a radical selected from (a-1), (a-20)and; each s is independently 0, 1, 2 or 5; and each $R^5$ is independently selected from hydrogen; halo; nitro; trihalo$C_{1-6}$alkyl; trihalo$C_{1-6}$alkyloxy; $C_{1-6}$alkyl; $C_{1-6}$alkyloxy; $C_{1-6}$alkylsulfonyl; (aryl)($C_{1-6}$alkyl)amino; arylsulfonyl; aryloxy; aryl$C_{2-6}$alkenediyl; di($C_{1-6}$alky)amino; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; oxazolyl; pyrrolyl; pyrazolyl; pyridinyl; pyridinyl substituted with $C_{1-6}$alkyloxy; quinolinyl; indolyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, hydroxy$C_{1-4}$alkylpiperazinyl$C_{1-4}$alkyl, hydroxy$C_{1-4}$alkyloxy$C_{1-4}$alkylpiperazinyl$C_{1-4}$alkyl, di(hydroxy$C_{1-4}$alkyl)amino$C_{1-4}$alkyl, pyrrolidinyl$C_{1-4}$alkyl, pyrrolidinyl$C_{1-4}$alkyloxy, morpholinyl$C_{1-4}$alkyloxy, morpholinyl$C_{1-4}$alkyl, and $C_{1-4}$alkylpiperazinyl$C_{1-4}$alkyl, or the central

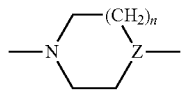

moiety is optionally bridged with a methylene bridge.

5. A compound as claimed in claim 1 wherein $R^{10}$ is hydrogen; $R^2$ is hydrogen, nitro, $C_{1-6}$alkyloxy, trifluoromethyl, di($C_{1-6}$alkyl)amino, hydroxyamino or naphtalenylsulfonylpyrazinyl; each $R^3$ represents a hydrogen atom; $R^4$ is hydrogen, hydroxy$C_{1-6}$alkyl, aminocarbonyl, hydroxyaminocarbonyl or di($C_{1-6}$alkyl)amino$C_{1-6}$alkyl;

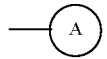

is a radical selected from (a-1), (a-20), and (a-21) each s is independently 0, 1, 2 or 5; and each $R^5$ is independently selected from hydrogen; halo; nitro; trihalo$C_{1-6}$alkyl; trihalo$C_{1-6}$alkyloxy; $C_{1-6}$alkyl; $C_{1-6}$alkyloxy; $C_{1-6}$alkylsulfonyl; (aryl)($C_{1-6}$alkyl)amino; arylsulfonyl; aryloxy; aryl$C_{2-6}$alkenediyl; di($C_{1-6}$alky)amino; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; oxazolyl; pyrrolyl; pyrazolyl; pyridinyl; pyridinyl substituted with $C_{1-6}$alkyloxy; quinolinyl; indolyl; phenyl; phenyl substituted with one, two or three substituents independently selected from halo, amino, $C_{1-6}$alkyl, $C_{1-6}$alkyloxy, hydroxy$C_{1-4}$alkyl, trifluoromethyl, trifluoromethyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino , di($C_{1-4}$alkyl)amino$C_{1-4}$alkyl($C_{1-4}$alkyl)amino$C_{1-4}$alkyl, hydroxy$C_{1-4}$alkylpiperazinyl$C_{1-4}$alkyl, hydroxy$C_{1-4}$alkyloxy$C_{1-4}$ alkylpiperazinyl$C_{1-4}$alkyl, di(hydroxy$C_{1-4}$alkyl)amino$C_{1-4}$alkyl, pyrrolidinyl$C_{1-4}$alkyl, pyrrolidinyl$C_{1-4}$alkyloxy, morpholinyl$C_{1-4}$alkyloxy, morpholinyl$C_{1-4}$alkyl, and $C_{1-4}$alkylpiperazinyl$C_{1-4}$alkyl, or the central

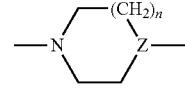

moiety is optionally bridged with a methylene bridge.

6. A compound as claimed in claim 1, wherein $R^1$ is —C(O)NH(OH); $R^2$ is hydrogen; each $R^3$ represents a hydrogen atom; $R^4$ is hydrogen;

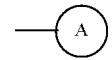

is a radical selected from (a-1) and (a-20); each s is independently 0 or 1; and each $R^5$ is independently selected from hydrogen; thiophenyl; thiophenyl substituted with di($C_{1-6}$alkyl)amino$C_{1-6}$alkyl, or $C_{1-6}$alkylpiperazinyl$C_{1-6}$alkyl; furanyl; phenyl; phenyl substituted with one substituents independently selected from di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl($C_{1-4}$alkyl)amino$C_{1-4}$alkyl, pyrrolidinyl$C_{1-4}$alkyl, pyrrolidinyl$C_{1-4}$alkyloxy and $C_{1-4}$alkylpiperazinyl$C_{1-4}$alkyl.

7. A compound according to claim 1, which is No. 142

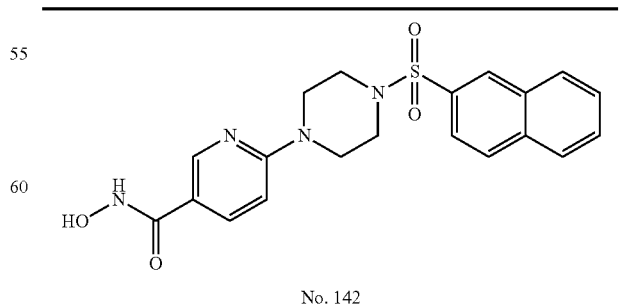

No. 142

8. A pharmaceutical composition comprising pharmaceutically acceptable carriers and as an active ingredient a therapeutically effective amount of a compound as claimed in claim 1.

9. A combination of an anti-cancer agent and a HDAC inhibitor as claimed claim 1.

* * * * *